(12) United States Patent
Bao et al.

(10) Patent No.: US 7,297,494 B2
(45) Date of Patent: Nov. 20, 2007

(54) ACTIVATABLE PROBES AND METHODS FOR IN VIVO GENE DETECTION

(75) Inventors: Gang Bao, Mableton, GA (US); Nitin Nitin, Atlanta, GA (US)

(73) Assignee: Georgia Tech Research Corporation, Atlanta, GA (US)

( * ) Notice: Subject to any disclaimer, the term of this patent is extended or adjusted under 35 U.S.C. 154(b) by 358 days.

(21) Appl. No.: 11/041,103

(22) Filed: Jan. 21, 2005

(65) Prior Publication Data

US 2005/0287548 A1    Dec. 29, 2005

Related U.S. Application Data

(63) Continuation-in-part of application No. 10/179,730, filed on Jun. 25, 2002, now Pat. No. 7,081,336.

(60) Provisional application No. 60/538,382, filed on Jan. 21, 2004, provisional application No. 60/538,381, filed on Jan. 21, 2004, provisional application No. 60/303,258, filed on Jul. 3, 2001, provisional application No. 60/300,672, filed on Jun. 25, 2001.

(51) Int. Cl.
*C12Q 1/68* (2006.01)
*C12N 15/11* (2006.01)
*C07H 21/02* (2006.01)
*C07H 21/04* (2006.01)

(52) U.S. Cl. .................. 435/6; 536/23.1; 536/24.3

(58) Field of Classification Search ............ None
See application file for complete search history.

(56) References Cited

U.S. PATENT DOCUMENTS

| 4,996,143 | A | 2/1991 | Heller et al. ............ 435/6 |
|---|---|---|---|
| 5,459,243 | A | 10/1995 | Acevedo et al. ............ 534/565 |
| 5,538,848 | A | 7/1996 | Livak et al. ............ 435/6 |
| 5,866,336 | A | 2/1999 | Nazarenko et al. ............ 435/6 |
| 5,876,930 | A | 3/1999 | Livak et al. ............ 435/6 |
| 5,891,016 | A | 4/1999 | Utsui et al. ............ 600/181 |
| 5,925,517 | A | 7/1999 | Tyagi et al. ............ 435/6 |
| 6,037,130 | A | 3/2000 | Tyagi et al. ............ 435/6 |
| 6,103,476 | A | 8/2000 | Tyagi et al. ............ 435/6 |
| 6,117,635 | A | 9/2000 | Nazarenko et al. ............ 435/6 |
| 6,150,097 | A | 11/2000 | Tyagi et al. ............ 435/6 |
| 6,177,555 | B1 | 1/2001 | Jayasena et al. ............ 536/23.1 |
| 6,228,592 | B1 | 5/2001 | Tsuji et al. ............ 435/6 |
| 6,248,518 | B1 | 6/2001 | Parkhurst et al. ............ 435/6 |
| 6,485,901 | B1 | 11/2002 | Gildea et al. ............ 435/5 |
| 6,528,267 | B1 | 3/2003 | Coull et al. ............ 435/6 |
| 6,607,889 | B1 | 8/2003 | Coull et al. ............ 435/6 |
| 6,649,349 | B2 | 11/2003 | Gildea et al. ............ 435/6 |
| 6,815,164 | B2 | 11/2004 | Kurn ............ 435/6 |
| 6,821,727 | B1 | 11/2004 | Livak et al. ............ 435/6 |
| 6,835,542 | B2 | 12/2004 | Becker et al. ............ 435/6 |
| 2004/0023248 | A1 | 2/2004 | O'Malley ............ 435/6 |
| 2004/0158051 | A1 | 8/2004 | Ozkan et al. ............ 536/23.1 |
| 2005/0003386 | A1 | 1/2005 | Bazan et al. ............ 435/6 |

FOREIGN PATENT DOCUMENTS

| EP | 0070685 | 1/1983 |
|---|---|---|
| WO | WO99/49293 | 9/1999 |
| WO | WO 03/000933 | 1/2003 |
| WO | WO 03/005013 | 1/2003 |
| WO | WO 2004/083902 | 9/2004 |

*Primary Examiner*—James Martinell
(74) *Attorney, Agent, or Firm*—Todd Deveau; Thomas, Kayden, Horstemeyer & Risley, LLP

(57) ABSTRACT

Probes for detecting a target polynucleotide are provided. One aspect provides a molecular beacon probe set wherein the donor molecular beacon comprises a quantum dot and an acceptor molecular beacon comprises at least one reporter. The probes optionally comprise a protein transduction domain, targeting signal, or a combination thereof. Methods for detecting target polynucleotides using the disclosed probes are also provided.

20 Claims, 19 Drawing Sheets
(7 of 19 Drawing Sheet(s) Filed in Color)

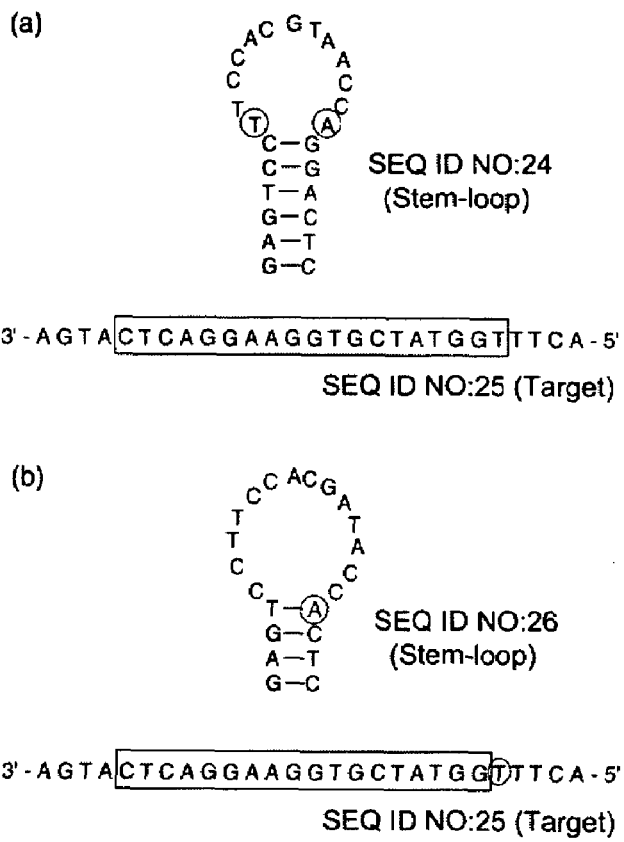
Figure 12 (a)-(b)
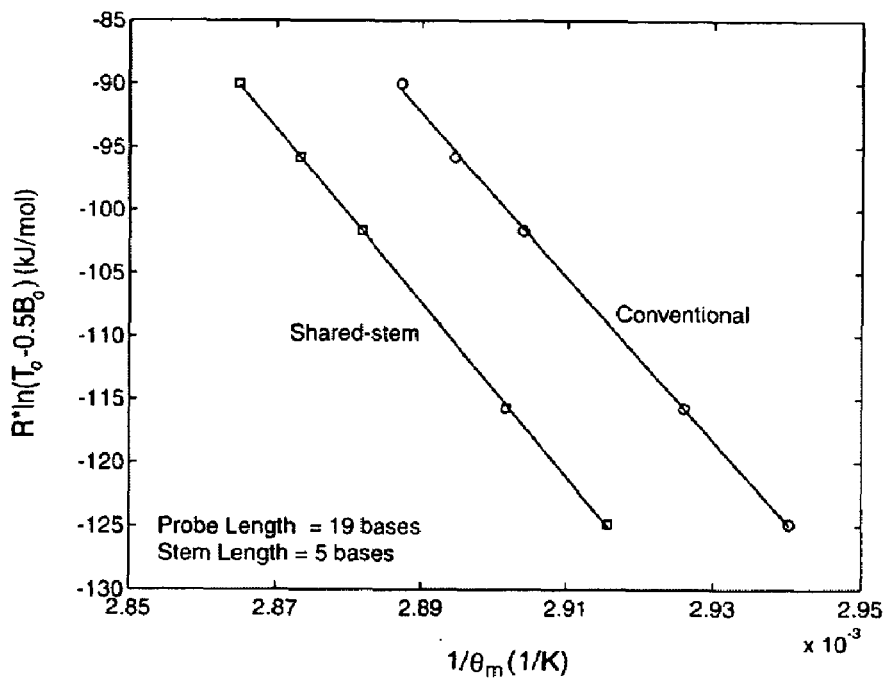
Figure 13

Figure 22 A-C

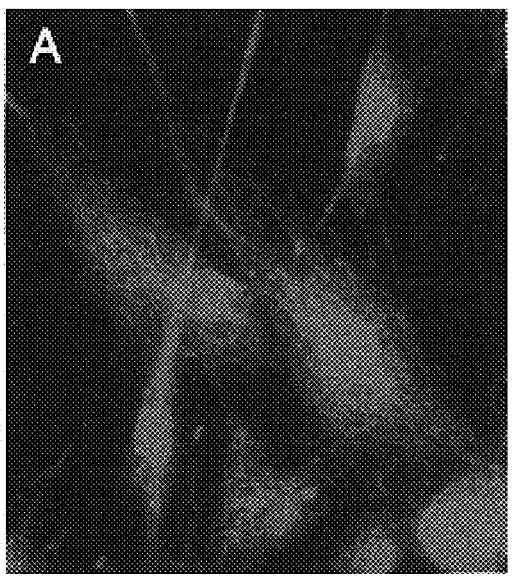
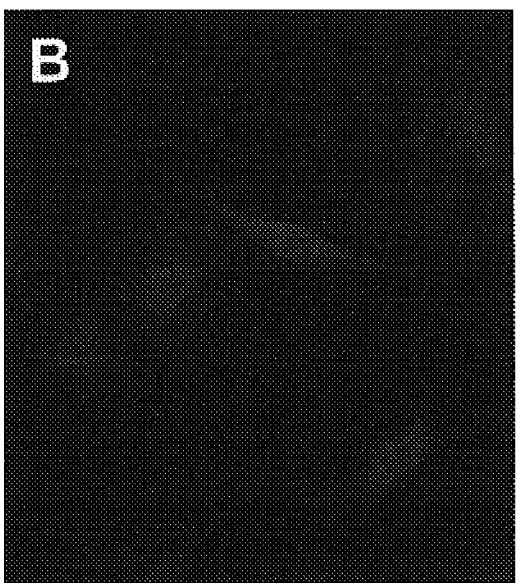
Figure 26

ID="1" />
ACTIVATABLE PROBES AND METHODS FOR IN VIVO GENE DETECTION

CROSS REFERENCE TO RELATED APPLICATIONS

This application is a continuation-in-part of U.S. Utility patent application Ser. No. 10/179,730 filed on Jun. 25, 2002, now U.S. Pat. No. 7,081,336 which claims the priority benefit of U.S. Provisional Patent Application Ser. No. 60/300,672 filed Jun. 25, 2001 and U.S. Provisional Patent Application Ser. No. 60/303,258 filed Jul. 3, 2001, and further claims the priority benefit of U.S. Provisional Patent Application Ser. No. 60/538,381 filed Jan. 21, 2004, and U.S. Provisional Patent Application Ser. No. 60/538,382 filed Jan. 21, 2004, the entire contents of each application is hereby incorporated by reference in their entireties

STATEMENT REGARDING FEDERAL SUPPORT OR DEVELOPMENT

This work was supported in part by Grant No. BSE-0222211 awarded by the National Science Foundation. Accordingly, the U.S. government may have certain rights in the claimed subject matter.

BACKGROUND

1. Technical Field

This application relates generally to the detection of target polynucleotides, such as mRNA. More specifically, the present disclosure relates to a dual molecular beacons approach that uses energy transfer.

2. Related Art

The ability to monitor and quantify the level of gene expression in living cells in real time can provide important information concerning the production, temporal and spatial processing, localization, and transport of specific mRNA in different conditions. This new type of information could potentially revolutionize biological studies and may also have applications in medical diagnostics and therapeutics. Technologies currently available for analysis and quantification of gene expression such as real-time PCR, Northern blotting, expressed sequence tag (EST), serial analysis of gene expression (SAGE) and DNA microarrays are powerful tools for in vitro studies; however, they are not capable of quantifying gene expression in living cells. There is a clear need to develop molecular probes that can recognize target mRNA in living cells with high specificity and instantaneously convert such recognition into a measurable signal with a high signal-to-background ratio.

Molecular beacons are a class of fluorescence-quenched nucleic acid probes that can be used in a quantitative fashion; these probes fluoresce upon target recognition (i.e., hybridization) with potential signal enhancement of >200 under ideal conditions. Structurally, they are dual-labeled oligonucleotides with a reporter fluorophore at one end and a dark quencher at the opposite end. They are designed to have a target-specific probe sequence positioned centrally between two short self-complementary segments which, in the absence of target, anneal to form a stem-loop hairpin structure that brings the fluorophore in close proximity with the quencher. In this configuration the molecular beacon is in the "dark" state. The hairpin opens upon hybridization with a complementary target, physically separating the fluorophore and quencher. In this configuration the molecular beacon is in the "bright" state. Transition between dark and bright states allows for differentiation between bound and unbound probes and transduces target recognition into a fluorescence signal.

Linear fluorescent probes, as are used in fluorescence in-situ hybridization (FISH), are "bright" in both the bound and unbound state. To detect positive signal after hybridization, unbound probe must be removed by washing, which prevents the application of this method to gene detection in living cells. In theory, molecular beacons do not require a washing step and so should be directly usable in living cells. However, interaction between molecular beacons and certain intracellular factors can cause fluorescence in the absence of target hybridization and lead to false-positive signals. Using conventional molecular-beacon-based methods, the fluorescent signal that results from target hybridization cannot be distinguished from any other event that spatially separates reporter from quencher, such as probe degradation by intracellular nucleases or interaction with DNA binding proteins that unwind the hairpin stem structure Two linear oligonucleotide probes labeled respectively with donor and acceptor fluorophores have been used in FRET-based studies of DNA hybridization, DNA secondary structure and RNA synthesis, however, the sensitivity of intracellular gene detection using such probes suffers from strong background signal due to unbound probes and cell autofluorescence.

The unique target recognition and signal transduction capabilities of molecular beacons have led to their application in many biochemical and biological assays including quantitative PCR, protein-DNA interactions, multiplex genetic analysis, and the detection of mRNA in living cells. However, false-positive signals due to protein-beacon interaction and nuclease-induced beacon degradation significantly limit the sensitivity of the in vivo applications. The thermodynamic and kinetic properties of molecular beacons are dependent on its structure and sequence in complex ways. Moreover, the signal-to-background ratio in target detection is dependent not only on design (length and sequence of the stem and probe) but also on the quality of oligonucleotide synthesis and purification and the assay conditions employed.

SUMMARY

The present disclosure provides compositions and methods for the detection of a target polynucleotide. One aspect, among others, provides a probe set comprising a donor polymer comprising a first polynucleotide binding domain complementary to a first region of a target polynucleotide. The polynucleotide binding domain is flanked by first and second stem regions which hybridize in the absence of the target polynucleotide to form a stem-loop structure. In some aspects, the stem regions or a portion of at least one stem region is also a portion of the polynucleotide binding domain. The donor polymer also comprises at least one quantum dot. Typically, at least one end of the donor polymer comprises at least one quantum dot. In some aspects, the donor polymer comprises one quantum dot at one end and another moiety (including but not limited to, metals, biomolecules, organic and inorganic moieties) on the other end.

The probe set further comprises an acceptor polymer comprising a second polynucleotide binding domain complementary to a second region of the target polynucleotide flanked by first and second stem regions which hybridize in the absence of the target polynucleotide to form a stem-loop structure. As noted above, the stem regions or a portion of the stem regions can be a portion of the polynucleotide binding domain. The acceptor polymer also comprises at least one reporter on at least one end of the acceptor polymer. In some aspects, the acceptor polymer has at least one reporter on both ends of the acceptor polymer. Energy transfer occurs between the donor and the at least one reporter when the donor polymer and the acceptor polymer hybridize to the target polynucleotide and the quantum dot is exposed to an exciting amount of energy. Representative donor and acceptor polymers include, but are not limited to molecular beacons.

Thus, another embodiment provides molecular beacon probes comprising fluorescent or luminescent energy transfer moieties. The molecular beacons contain polynucleotide binding domains that enable the molecular beacons to hybridize sufficiently near each other on a target polynucleotide, e.g. mRNA, for energy transfer to occur and a detectable signal to be generated.

Other aspects provide probes comprising at least one protein transduction domain (PTD), at least one targeting signal, fragments thereof, or combinations thereof, operably linked to the probe. PTDs and targeting signals enable the probes to be non-invasively delivered to specific intracellular regions.

Still another aspect provides methods for using the disclosed probes to detect in vivo gene expression. In some aspects, the expression of more than one gene can be detected in vivo. Generally, the disclosed probes are delivered to at least one living cell, and the quantum dot is exposed to an exciting amount of energy. The presence of a target polynucleotide is correlated with a detectable signal produced by the reporter in response to energy transfer from the quantum dot donor. The amount of detectable signal can also be used to quantitate the levels of target nucleotide in the cell.

BRIEF DESCRIPTION OF THE FIGURES

The patent or application file contains at least one drawing executed in color. Copies of this patent or patent application publication with color drawing(s) will be provided by the Office upon request and payment of the necessary fee.

FIG. 11a shows Conventional molecular beacons have stem sequences that are independent of the target sequence. FIG. 11b shows shared-stem molecular beacons are designed such that one arm of the stem participates in both hairpin formation and target hybridization.

FIGS. 12a and 12b show examples of the design constraint of shared-stem molecular beacons with certain stem/probe combinations. FIG. 12a shows the design of a molecular beacon with a probe length of 19 bases and a stem length of 6 bases inadvertently resulted in additional bases participating in stem formation (circles). FIG. 12a shows the design of a molecular beacon with a probe length of 18 bases and a stem length of 4 bases inadvertently resulted in an additional base participating in target hybridization (circle).

FIG. 13 shows a comparison of the milting temperature of shared-stem and conventional molecular beacons as determined by the initial concentrations of probe and target. By fitting the data with a straight line, changes in enthalpy (slope of the fitted line) and entropy (y-intercept) characterizing the phase transition between bound-to-target and stem-loop conformations of a molecular beacon were obtained.

FIG. 17a shows melting curves for conventional and shared-stem molecular beacons in the presence of wild-type (solid line) and mutant (dashed line) target. FIG. 17b shows the difference in the fraction of conventional or shared-stem molecular beacons bound to wild-type and mutant targets.

FIGS. 26A-C are fluorescence micrographs showing fluorescence in situ hybridization (FISH) studies. (a) Detection of K-ras mRNA in fixed HDF cells using fluorescently labeled linear probes. Note the filamentous localization pattern near the cell peripheral region. (b) A negative control study of the FISH assay using fluorescently labeled linear Poly-A probes resulted in very low background

DETAILED DESCRIPTION

Figure 1:
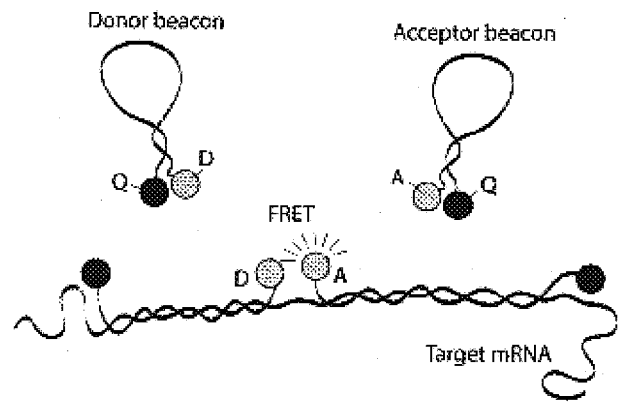
FIG. 1 shows hybridization of the donor and acceptor molecular beacons to adjacent regions on the same mRNA target results in FRET. By detecting FRET, fluorescence signals due to probe/target binding can be distinguished from that due to beacon degradation and non-specific interactions. In the figure, letters Q, D and A represent respectively quencher, donor dye and acceptor dye molecules.

The present disclosure may be understood more readily by reference to the following detailed description of the multiple embodiments of the disclosure and the Examples included therein. Before the present probes, probe sets, compositions, and methods are disclosed and described, it is to be understood that this disclosure is not limited to any specific probes, polynucleotide probes, nucleic acid probes, specific polynucleotide targets, specific nucleic acid targets, specific cell types, specific conditions, or specific methods, etc., as such may, of course, vary, and the numerous modifications and variations therein will be apparent to those skilled in the art. It is also to be understood that the terminology used herein is for the purpose of describing particular embodiments only and is not intended to be limiting. As used in the specification and in the claims, "a" or "an" can mean one or more, depending upon the context in which it is used. Thus, for example, reference to "a nucleic acid probe" can mean that one or more than one nucleic acid probe can be utilized.

Definitions

In describing and claiming the disclosed subject matter, the following terminology will be used in accordance with the definitions set forth below, unless indicated otherwise.

"Localization Signal", "Localization Sequence", "Localization Domain", "Targeting Signal", "Targeting Sequence" or "Targeting Domain" are used interchangeably and refer to a signal that directs a molecule to a specific cell, tissue, organelle, or intracellular region. The signal can be polynucleotide, polypeptide, or carbohydrate moiety or can be an organic or inorganic compound sufficient to direct an attached molecule to a desired location. Exemplary organelle localization signals include nuclear localization signals known in the art and other organelle localization signals known in the art and described in Emanuelson et al., Predicting Subcellular Localization of Proteins Based on Their N-terminal Amino Acid Sequence. *Journal of Molecular Biology.* 300(4):1005-16, 2000 Jul. 21, and in Cline and Henry, Import and Routing of Nucleus-encoded Chloroplast Proteins. *Annual Review of Cell & Developmental Biology.* 12:1-26, 1996, the disclosures of which are incorporated herein by reference in their entirety. In some embodiments the organelle localization signals include signals having or conferring a net charge, for example a positive charge. Positively charged signals can be used to target negatively charged organelles such as the mitochondria. Negatively charged signals can be used to target positively charged organelles or regions.

"Protein Transduction Domain" or PTD refers to a polypeptide, polynucleotide, carbohydrate, or organic or inorganic compounds that facilitates traversing a lipid bilayer, micelle, cell membrane, organelle membrane, or vesicle membrane. A PTD attached to another molecule facilitates the molecule traversing membranes, for example going from extracellular space to intracellular space, or cytosol to within an organelle. Exemplary PTDs include but are not limited to HIV TAT YGRKKRRQRRR (SEQ ID NO. 38) or RKKRRQRRR (SEQ ID NO. 39); 11 Arginine residues, or positively charged polypeptides or polynucleotides having 8-15 residues, preferably 9-11 residues.

As used herein, the term "polynucleotide" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. The terms "nucleic acid," "nucleic acid sequence," or "oligonucleotide" also encompass a polynucleotide as defined above.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

The term "molecular beacon" generally means labeled, for example dual-labeled polynucleotide probes comprising a polynucleotide binding domain and stem regions. The stem regions hybridize in the absence of a target polynucleotide and form a stem-loop structure. In particular, the term molecular beacon includes hairpin polynucleotide probes labeled with a quantum dot that form a stem-loop structure in the absence of a target polynucleotide.

Probes

One embodiment of disclosure provides probes, in particular a set of probes for detecting the presence of absence of at least one target polynucleotide. An exemplary probe set comprises at least two probes. The first probe is a donor polymer comprising a first polynucleotide binding domain complementary to a first region of a target polynucleotide. The polynucleotide binding domain is flanked by first and second stem regions which hybridize in the absence of the target polynucleotide to form a stem-loop structure. The donor polymer also includes at least one quantum dot. Typically the quantum dot is attached to one end of the probe and serves as a donor during energy transfer. In other embodiments, the donor polymer comprises quantum dots attached to opposite ends of the donor polymer.

The second probe is an acceptor polymer comprising a second polynucleotide binding domain complementary to a second region of the target polynucleotide flanked by first and second stem regions which hybridize in the absence of the target polynucleotide to form a stem-loop structure. The acceptor polymer also comprises at least one reporter or label, and optionally, at least one quencher. One embodiment provides an acceptor probe comprising a reporter that does not emit a detectable signal when exposed to an exciting amount of energy for donor excitation. Another embodiment provides an acceptor probe comprising a reporter that emits a detectable signal when exposed to energy transferred from the donor. Still another embodiment provides an acceptor probe comprising at least one quencher so that in the absence of a target polynucleotide the reporter is quenched. Yet another embodiment provides an acceptor polymer comprising at least one reporter attached to both ends of the polymer.

Energy transfer occurs between the donor of the donor polymer and the at least one reporter of the acceptor polymer when the donor polymer and the acceptor polymer hybridize to the target polynucleotide and the quantum dot is exposed to an exciting amount of energy. An exciting amount of energy refers to an amount of energy that results in the emission of energy by the quantum dot. The emissions of the quantum dot excite the reporter which generates a detectable signal. The polynucleotide binding domains of the donor and acceptor polymers are designed so that the two probes hybridize to the target polynucleotide and the donor of the donor polymer and the reporter of the acceptor polymer are positioned to permit energy transfer between the donor and the reporter.

Labeling of the probes can be accomplished, for example, during oligonucleotide synthesis, by adding amino-modifier dC and amino-modifier dT in place of a 2'-deoxycytidine and thymidine base, respectively. In certain cases, fluorescently labeled nucleotides can be directly incorporated into the polymer chain-at desired places. After deprotection, the primary amine on the C6 analogues can be separated from the oligonucleotide by a spacer arm with a total of about 1-10 atoms, which can then be labeled with fluorophores. Alternatively, customized internal Cy3 labeling of oligonucleotides can be performed at specific companies (e.g., Glen Research). The length of the modified oligonucleotide on the acceptor probe can be adjusted so the self-quenching of the reporter, for example Cy3, is minimized.

Another embodiment of the present disclosure provides donor and acceptor polymer probes that can non-invasively report the presence or absence of a target polynucleotide either in vivo or in vitro. Non-invasive delivery refers to delivery without significant physical damage to a cell or tissue using for example, a mechanical device such as needle or other mechanical or physical means such as poration that may cause significant cellular or tissue damage. Embodiments of the disclosure provide polymer probes modified with a protein transduction domain (or cell penetrating peptide) to facilitate translocation of the probe from the extracellular space to intracellular space. The polymer probes can translocate to any region of the interior of a cell including the interior of membrane bound organelles such as the nucleus, mitochondrion, or chloroplast. It will be appreciated by those of skill in the art that any membrane organelle is included within the scope of the disclosure. It will be further appreciated that any cell having a membrane or cell wall is within the scope of this disclosure including, but not limited to animal cells such as human cells, and plant cells. Microbial cells and bacterial cells are also within the scope of this disclosure.

Another embodiment provides polymer probes that can be delivered into biological cells, tissues and animals using, for example, microinjection, electroporation, toxin-based delivery methods (for example, using streptolysin O), and transfection agents (including liposome-based and dendrimer-based transfection).

Other embodiments provide polymer probes that are further modified to include targeting signals such as intracellular targeting signals, organelle targeting signals, cellular targeting signals, tissue targeting signals, or organ targeting signals. Generally, such targeting signals are known in the art. Targeting signals include, but are not limited to, amino acid or nucleic acid sequences, as well as lipids or carbohydrates that target the probe to a specific cell, tissue, organ or intracellular region of a cell. Such targeting can be accomplished through receptor:ligand interactions or by using a targeting signal that modifies the polarity, hydrophobicity, hydrophilicity, or any combination thereof, of the disclosed probes. Thus, the targeting signal can confer a positive or negative charge to the probe as needed. Exemplary targeting signals include, but are not limited to, growth factors, growth factor receptors, antibodies or fragments thereof specific for extracellular epitopes, carbohydrates, lipids, peptides, nucleic acids, nuclear localization signals, mitochondria localization signals, chloroplast localization signals, polar or non-polar small molecules, co-factors and vitamins.

It will be appreciated by those of skill in the art that the disclosed probes can include a PTD, a targeting signal, or a combination thereof. The PTD, the targeting signal, or both can be releaseably linked to the probe, for example through cleavable bonds, so that the probe is released from the PTD or targeting signal when the probe arrives at a desired location. In one aspect, the PTD is cleaved when the probe enters the cytosol and the targeting signal remains linked to the probe. In another aspect, the targeting signal is removed from the probe when the probe reaches the desired location.

The disclosed probes include, but are not limited to, labeled oligonucleotides or polynucleotides such as molecular beacons. Some molecular beacons are labeled with a reporter and a quencher, for example the acceptor polymer can be labeled with a reporter and a quencher so that the reporter is quenched in the absence of a target polynucleotide. As used herein, molecular beacons also include polynucleotides labeled with a quantum dot. Generally, molecular beacons include a sequence that is complementary to a target polynucleotide (target recognition sequence or polynucleotide binding domain). The degree of complementarity is sufficient to enable sequence specific interactions between the probe and the target polynucleotide. Some embodiments can detect single base differences or single nucleotide polymorphisms in a target polynucleotide. The disclosed probes may have target recognition sequences or polynucleotide binding domains 7-140 nucleotides, but it will be appreciated that the target recognition sequence can be of any length that permits sequence specific association with the target polynucleotide. In some embodiments, the sequences flanking the target recognition sequences form a stem hybrid, or "stem duplex" 3-25 nucleotides in length. Modified nucleotides and modified nucleotide linkages may be used to produce the disclosed probes and are described more fully below. Such modifications are known in the art and include modifications to increase resistance to the enzymatic degradation. In non-limiting embodiments, labile phosphodiester or phosphoester linkages may be replaced with more stable linkages, such as phosphorothioate or thioester linkages. For example the disclosed probes may include, for example, peptide nucleic acid ("PNA") linkages. The disclosed compositions and target polynucleotides can be DNA, RNA including rRNA, nuclear RNA, mRNA, cDNA, genomic DNA, or combinations thereof.

Quantum Dots

Another embodiment provides dual FRET hairpin probes with quantum dots as the donor. In some embodiments, signal intensity is increased and photobleaching is overcome by using quantum dot based probes. Quantum dots are semiconductor nanocrystals about 1 to about 20 nm in size. In comparison with organic dyes and fluorescent proteins, quantum dots represent a new class of fluorescent labels with unique advantages. For example, the fluorescence emission spectra of quantum dots can be continuously tuned by changing the particle size, and a single wavelength (typically in the blue or UV spectrum) can be used for simultaneous excitation of all different-sized quantum dots. Surface-passivated quantum dots are highly stable against photobleaching and have narrow, symmetric emission peaks (25-30 nm wide at half maximum intensity). Quantum dots also have high quantum yield: it has been estimated that CdSe quantum dots are about 20 times brighter and 100 times more stable than single rhodamine-6G molecules The quantum dots of the present disclosure include a number of types of quantum dots such as, but not limited to, semiconductor, metal, and metal oxide nanoparticles (e.g., gold, silver, copper, titanium, nickel, platinum, palladium, oxides thereof (e.g., $Cr_2O_3$, $CO_3O_4$, NiO, MnO, $CoFe_2O_4$, and $MnFeO_4$), and alloys thereof), metalloid and metalloid oxide nanoparticles, the lanthanide series metal nanoparticles, and combinations thereof. In particular, semiconductor quantum dots are described in more detail below and in U.S. Pat. No. 6,468,808 and International Patent Application WO 03/003015, which are incorporated herein by reference.

Suitable quantum dots include, but are not limited to, luminescent semiconductor quantum dots. In general, quantum dots include a core and a cap, however, uncapped quantum dots can be used as well. The "core" is a nanometer-sized semiconductor. While any core of the IIA-VIA, IIIA-VA or IVA-IVA, IVA-VIA semiconductors can be used in the context of the present disclosure, the core must be such that, upon combination with a cap, a luminescent quantum dot results. A IIA-VIA semiconductor is a compound that contains at least one element from Group IIB and at least one element from Group VIA of the periodic table, and so on. The core can include two or more elements. In one embodiment, the core is a IIA-VIA, IIIA-VA or IVA-IVA semiconductor that ranges in size from about 1 nm to about 20 nm. In another embodiment, the core is more preferably a IIA-VIA semiconductor and ranges in size from about 2 nm to about 10 nm. For example, the core can be CdS, CdSe, CdTe, ZnSe, ZnS, PbS, PbSe or an alloy.

The "cap" is a semiconductor that differs from the semiconductor of the core and binds to the core, thereby forming a surface layer on the core. The cap can be such that, upon combination with a given semiconductor core a luminescent quantum dot results. The cap should passivate the core by having a higher band gap than the core. In one embodiment, the cap is a IIA-VIA semiconductor of high band gap. For example, the cap can be ZnS or CdS. Combinations of the core and cap can include, but are not limited to, the cap is ZnS when the core is CdSe or CdS, and the cap is CdS when the core is CdSe. Other exemplary quantum does include, but are not limited to, CdS, ZnSe, CdSe, CdTe, $CdSe_xTe_{1-x}$, InAs, InP, PbTe, PbSe, PbS, HgS, HgSe, HgTe, CdHgTe, and GaAs.

The wavelength emitted (i.e., color) by the quantum dots can be selected according to the physical properties of the quantum dots, such as the size and the material of the nanocrystal. Quantum dots are known to emit light from about 300 nanometers (nm) to 1700 nm (e.g., UV, near IR, and IR). The colors of the quantum dots include, but are not limited to, red, blue, green, and combinations thereof. The color or the fluorescence emission wavelength can be tuned continuously. The wavelength band of light emitted by the quantum dot is determined by either the size of the core or the size of the core and cap, depending on the materials which make up the core and cap. The emission wavelength band can be tuned by varying the composition and the size of the QD and/or adding one or more caps around the core in the form of concentric shells.

The intensity of the color of the quantum dots can be controlled. For each color, the use of 10 intensity levels (0, 1, 2, . . . 9) gives 9 unique codes ($10^1-1$), because level "0" cannot be differentiated from the background. The number of codes increase exponentially for each intensity and each color used. For example, a three color and 10 intensity scheme yields 999 ($10^3-1$) codes, while a six color and 10 intensity scheme has a theoretical coding capacity of about 1 million ($10^6-1$). In general, n intensity levels with m colors generate ($n^m-1$) unique codes. Use of the intensity of the quantum dots has applications in quantum dots including a plurality of different types of quantum dots having different intensity levels and also in quantum dots including a plurality of different types of quantum dots having different intensity levels that are included in a porous material. The quantum dots are capable of absorbing energy from, for example, an electromagnetic radiation source (of either broad or narrow bandwidth), and are capable of emitting detectable electromagnetic radiation at a narrow wavelength band when excited. The quantum dots can emit radiation within a narrow wavelength band (FWHM, full width at half maximum) of about 40 nm or less, thus permitting the simultaneous use of a plurality of differently colored quantum dots with little or no spectral overlap.

The synthesis of quantum dots is well known and is described in U.S. Pat. Nos. 5,906,670; 5,888,885; 5,229,320; 5,482,890; 6,468,808; 6,306,736; 6,225,198, etc., International Patent Application WO 03/003015, (all of which are incorporated herein by reference) and in many research articles. The wavelengths emitted by quantum dots and other physical and chemical characteristics have been described in U.S. Pat. No. 6,468,808 and International Patent Application WO 03/003015 and will not be described in any further detail. In addition, methods of preparation of quantum dots are described in U.S. Pat. No. 6,468,808 and International Patent Application WO 03/003015 and will not be described any further detail.

The hydrophobic protection structure can include a capping ligand and/or a block copolymer. In particular, the hydrophobic protection layer includes the capping ligand and the block copolymer, where the capping ligand and the block copolymer interact with one another to form the hydrophobic protection structure. As such, the capping ligand and the block copolymer are selected to form an appropriate hydrophobic protection structure. For example, the block copolymer and the quantum dot can interact through interactions such as, but not limited to, hydrophobic interactions, hydrophilic interactions, pi-stacking, etc., depending on the surface coating of the quantum dot and the molecular structure of polymers.

Figure 20A:
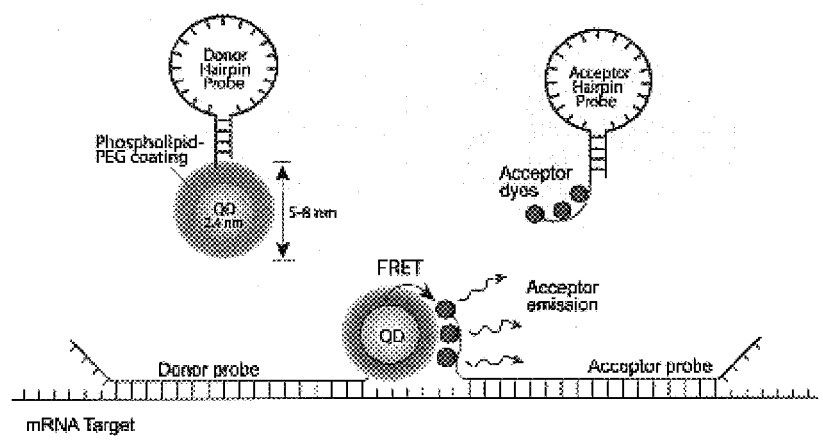
FIGS. 20a and 20b show an exemplary embodiment of the disclosed probes and the excitation and emission spectra of an exemplary quantum dot and reporter.
Figure 20B:
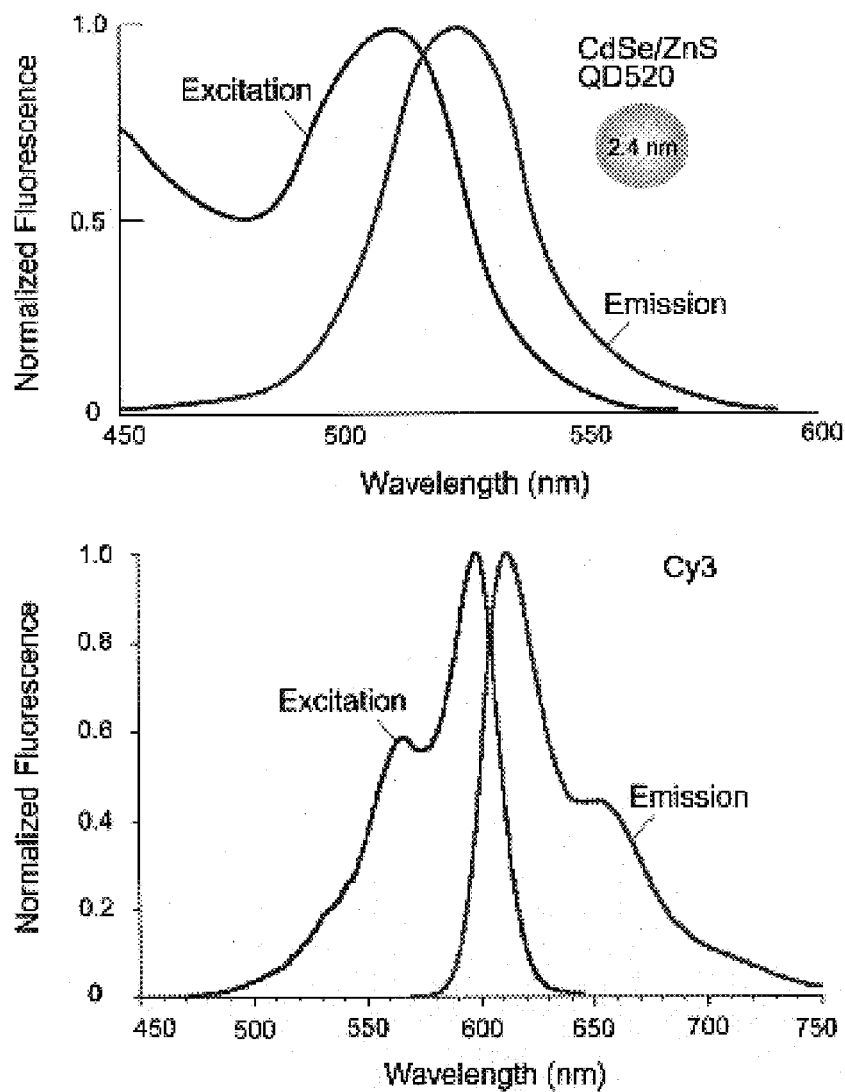

As illustrated in FIG. 20a, an exemplary donor hairpin probe is conjugated to the surface of a quantum dot (QD), which is optionally coated with phospholipid-PEG. The acceptor stem-loop hairpin probe is labeled with at least one, typically 2-3 reporters or acceptor dyes attached to one arm of the stem. Hybridization of both donor and acceptor probes to adjacent regions of the same target polynucleotide, for example mRNA, will bring the acceptor dyes in close proximity of the quantum dot, resulting in FRET and fluorescence emission characteristic of the acceptor dye when the quantum dot is exposed to an exciting amount of energy, for example excited with a wavelength less than about 450 nm. A suitable quantum dot includes, but is not limited to CdSe/ZnS quantum dot (Evident Technologies) as a donor, which has a broad excitation spectrum (FIG. 20b), and Cy3 as the acceptor. Generally, the quantum dot has a diameter of about 2.4 nm. As shown in FIG. 20b, Cy3 has some overlap between its excitation spectrum (maximum at 548 nm) and the emission spectrum of the QD (with an emission peak at 520 nm). When a FRET assay is performed with 400 nm excitation and 570 nm emission detection, there is no direct excitation of Cy3, and very low signal of the QD (FIG. 20B). Therefore, no quenching is necessary for the QD and Cy3 dye. It will be appreciated that other QD and organic dye pairs can be used to achieve the maximum signal-to-background ratio based on their excitation and emission spectra.

Another embodiment provides a donor polymer probe wherein the quantum dot is encapsulated, for exarriple in a polymer, lipid, phospholipid, or a phospholipid monomethoxy PEG micelle. The hydrophobic core of a DSPE-PEG micelle provides a cavity to encapsulate individual QDs, while the dense PEG polymer layer on the outer surface facilitates conjugation of the hairpin probe. Many functionalized PEG-lipid derivatives, such as DSPE-PEG-maleimide and DSPE-PEG-amine, are commercially available (Avanti Polar Lipid). In some embodiments, the disclosed probes have one QD.

In one embodiment, the organic soluble quantum dots may be coated with amphiphilic polymers such as octylamine-modified polyacrylic acid, which can be further cross linked to increase the stability of coatings or chemically modified to introduce functional groups for conjugation of biopolymer probes. Further these coatings may have functional groups for conjugation of linker proteins such as streptavidin, which may provide further possibilities to chemically conjugate other moieties to the probe.

In another embodiment, the amphiphilic polymers may be biological polymers such as peptides which may provide water-solubility and functionalization to quantum dots. These peptides may contain modified amino acids for various functions such as bioconjugation.

In another embodiment, the coatings may be of the type of DHLA (Lipoic Acid) or Mercaptoacetic Acid-coated in which the Thiol group of the coatings form a bond with the capping layer (e.g., ZnS) of the quantum dots. In such bi-functional coatings, one part of the molecule forms a bond with the quantum dot surface and other functional molecule provides the chemistry for bioconjugation of probes.

In still another embodiment, silica based coatings such as silanes may be used to produce water-soluble quantum dots. These silanes are chemically linked to the surface of the quantum dot. Further, these coatings may be modified with molecules such as PEG to provide increased water solubility.

Methods of Detection

Probes and probes pairs of the present disclosure can be used to detect, localize, or quantify a target polynucleotide in a cell, in particular a living cell, tissue, or organ. Representative cells include plant and animal cells. Target polynucleotides can be any polymer of nucleotides, DNA, RNA or combinations thereof, genomic, mRNA, nuclear RNA, enzymatic RNA, enzymatic DNA, or ribosomal RNA. Embodiments of the disclosed methods provide real-time visualization of specific endogenous mRNA expression in vivo.

One embodiment of the disclosure provides a method of detecting at least one target polynucleotide using the disclosed probes and probe sets. An exemplary method of detecting a target polynucleotide comprises delivering at least one probe, probe set, or molecular beacon pair to the interior of a cell or organelle. The at least one probe set or molecular beacon pair comprises a donor molecular beacon and an acceptor molecular beacon. The donor molecular beacon comprises a quantum dot and forms a stem-loop structure in the absence of a target polynucleotide. The acceptor molecular beacon comprises at least one reporter and forms a stem-loop structure in the absence of the target polynucleotide. The acceptor molecular beacon optionally includes at least one quencher opposite the reporter so that the reporter is quenched in the absence of the target polynucleotide. The method further comprises exposing the quantum dot to an exciting amount of energy so that energy transfer occurs between the quantum dot of the donor molecular beacon and the reporter of the acceptor molecular beacon when the donor molecular beacon and the acceptor molecular beacon hybridize to the target polynucleotide. The energy transfer enables the reporter to produce a detectable signal. The detectable signal can indicate the presence or location of the target polynucleotide in cell as well as the amount of target polynucleotide in the cell.

Another embodiment provides a method for sorting living cells that express a target polynucleotide or a predetermined level of a target polynucleotide. In this embodiment, a plurality of cells are loaded with the disclosed probes or probe sets. The cells are exposed to an exciting amount of radiation sufficient to allow energy transfer to occur between the donor of the donor probe and the reporter of the acceptor probe when the donor and acceptor probes hybridize to the target polynucleotide. Cells having a detectable signal from the reporter can be selected and separated from cells that do not have a detectable signal from the reporter. Separating the cells can be performed using automated devices which include, but are not limted to fluorescence-activated cell sorters. Representative cells include, but are not limited to eukaryotic cells, animal cells, human cells, stem cells, germ cells, pluripotent cells, totipotent cells, undifferentiated cells, endodermal cells, mesenchymal cells, ectodermal cells, brain cells, skin cells, heart cells, bone marrow cells, blood cells, lymphocytes, adipose cells, smooth muscle cells, muscle cells, osteoclasts, osteoblasts, macrophage, T-cells, helper T-cells, among others.

The presence of the detectable signal in the cells is indicative of the expression of the target polynucleotide by the cell. The expression of the target polynucleotide can also be correlated to the presence or predisposition to a pathology including, but not limted to cancer, viral infection, genetic disease, Alzheimer's Disease, muscular dystrophy, diabetes, obesity, heart disease, atherosclerosis, inflammatory pathologies, autoimmune diseases, among others.

In other embodiments, a detectable signal is indicative of a point mutation, deletion or insertion in the target polynucleotide relative to a control polynucleotide. Exemplary target polynucleotides include, but are not limited to polynucleotides encoding an oncogene, transgene, signal transduction protein, growth factor, viral protein, K-ras, survivin, p53, p16, DPC4, or BRCA2.

In some embodiments, in vivo or in vitro detection of more than one target polynucleotide (multiplexing) is accomplished by using at least two probe sets specific for different target polynucleotides. In one embodiment, the reporter for the acceptor probe specific for a first target polynucleotide provides a different detectable signal than the reporter for the acceptor probe specific for the second target polynucleotide. For example, one reporter can have a detectable signal at one wavelength, and the other reporter can have a detectable signal at a different wavelength. The presence of a detectable signal from either reporter or the combined detectable signal of both reporters is indicative of the presence and optionally the location of the respective target polynucleotides. The movement of target polynucleotides over a period of time can also be tracked and visualized using the disclosed probes and probe sets.

Other embodiments provide methods for detecting at least one target polynucleotide in vitro, for example in an array, solution, test tube, gel, matrix, or the like. The disclosed probes can be fixed or attached to a solid support. Alternatively, the target polynucleotide can be fixed or attached to a solid support. The disclosed probes can be combined in vitro with a sample suspected of containing a target polynucleotide. The combination is exposed to an exciting amount of energy. A detectable signal observed from the reporter indicates the presence of the target polynucleotide in the sample.

It will be appreciated by those of skill in the art that the disclosed probes can be used with single- or multiple-photon microscopy, time-resolved fluorescence microscopy or fluorescence endoscopy, among others.

One embodiment provides a method for detecting cells expressing a target polynucleotide including contacting a cell suspected of expressing the target polynucleotide with the disclosed probes or probe pairs which are individually operably linked to a protein transduction domain, The probes include a region complementary to the target polynucleotide. The probes can be added to a cell culture of immortalized cells, primary culture cells, transfected cells, or administered to a organism or tissue. Preferred tissues are those tissues with optical characteristics that enable the detection of the probes or it may involve the use of endoscopic instruments in combination with appropriate optical instrumentation for excitation and detection of electromagnetic emission in vivo. Preferred organisms include humans and zebra fish. When used with tissues, near-infrared labels are preferred.

Once the cell is contacted with the probe, the PTD on the probe facilitates translocation of cell membranes including, but not limited to, lipid bilayers, micelles, vesicles, and organelles such as the nucleus, mitochondria or chloroplast. The PTD enables the probe to travel from extracellular space to intracellular space including the interior of organelles. The probes can be irradiated with an exciting amount of electromagnetic radiation. An exciting amount of radiation is that amount of radiation sufficient to enable the probe to emit electromagnet radiation. The electromagnetic energy emitted by the probe indicates that probe has bound its complement and that the cell expresses the target polynucleotide.

Another embodiment provides a method for sorting cells expressing a target polynucleotide. A plurality of cells suspected of expressing the target polynucleotide is contacted with at least one probe or at least one probe pair, for example a quantum dot probe, optionally, operably linked to a protein transduction domain, wherein the protein transduction domain facilitates translocation of the at least one probe to at least one of the plurality of cells' interior. The probe includes a region complementary to the target polynucleotide. The plurality of cells are irradiated with an exciting amount of electromagnetic energy and electromagnetic energy emitted in response to the exciting amount of electromagnetic radiation by the molecular beacon in the interior of at least of the plurality of cells can be detected. Cells emitting a detectable amount of electromagnetic radiation can then be separated from cells, which are not emitting a detectable amount of electromagnetic radiation. Methods for separating cells are known in the art, for example, by using a fluorescence-activated cell sorter, which are commercially available.

Another embodiment provides a method for detecting a target polynucleotide in a host. This embodiment includes administering to the host the disclosed probes which are optionally, operably linked to a protein transduction domain, and optionally linked to a targeting signal. Generally, the probes are in the form of a pharmaceutical composition. The probes are irradiated with an exciting amount of electromagnetic radiation, and the electromagnetic radiation emitted by the probes in response to the exciting amount of electromagnetic radiation is detected. The detected electromagnetic radiation can be correlated with the presence, location, and quantity of the target polynucleotide in the host, cell, or tissue.

Still another embodiment provides an approach to study the transport of RNA in living cells and model organisms such as oocytes using the disclosed probes which are optionally, operably linked to a protein transduction domain as well as a targeting signal such as a nuclear localization signal (NLS) whenever necessary. For these studies, the disclosed probes may be delivered specifically to the nuclear compartment, where they hybridize with the target RNA molecules which may be subsequently transported to the cytoplasm. This real time imaging of RNA transport may be used to gain a better understanding of RNA biology and developmental biology. Further, the disclosed probes may be linked to a targeting sequence such as NLS and modified using a caged fluorophore. In the native state the modified probe does not emit much signal. Using controlled excitation in the nuclear compartment, the caged molecule may be released, emitting a signal that can be imaged for studying transport of RNA molecules from nucleus to cytoplasm.

Another embodiment provides an approach in which co-localization of RNA with subcellular organelles and the dynamics of RNA or DNA molecules interacting with proteins and can be studied. For this approach, the disclosed probes, optionally, operably linked to a protein transduction domain optionally linked to a targeting signal is used in conjugation with fusion protein of interest (GFP-protein) or any fluorescently labeled protein (fluorescent labeled antibody targeted protein) or subcellular organelle. The molecular beacons target the nucleic acid molecules of interest (RNA or DNA) and, upon hybridization with the target, provide electromagnetic emission in particular wavelength range, while the fusion protein or any fluorescently labeled protein or organelle provides the non-overlapping wavelength upon excitation. This allows one to study the RNA-protein interactions and its dynamics in living cells.

Yet another embodiment provides a method for identifying compounds that interfere with the expression of a target polynucleotide, for example a nucleic acid suspected to be involved with a pathological condition, for example cancer or other disease states. The method includes contacting a living cell or a plurality of living cells with a compound suspected of modulating the expression of a gene, for example a small organic molecule or antisense drug, contacting the cell with a probe having a region complementary to a transcript of the gene, irradiating the probe or the cell with an exciting amount of electromagnetic radiation, and detecting the emission of electromagnetic radiation from the probe, wherein detectable emission from the probe is indicative of expression or the location of the gene. The cell can be a primary culture, immortalized cell, or transfected cell. Typically, a cell is transfected with a gene of interest and the probe is specific for transcripts of the gene of interest. A test compound can be selected based on its ability to decrease the expression of a gene or increase the expression of a gene when compared to a control sample. A control sample includes a cell contacted with the probe in the absence of the test compound. Decreased expression of a gene is indicated by little to no detectable emissions from the probe; whereas, increased gene expression is indicated by detectable emissions from the probe which are greater from cells treated with the test compound compared to cells not treated with the test compound. This screening method is adaptable to high-throughput screening and imaging, for example using a fluorescence activated cell sorter, cell arrays, tissue arrays, or other microfluidic devices, which allow for high throughput detection and imaging. Combinatorial libraries can be used with this method to identify compounds that modulate gene expression in vivo.

Another embodiment provides a method for determining the effectiveness of a therapeutic, for example a therapeutic that modulates gene expression of a host or suspected of modulating gene expression. The disclosed probes can be used to obtain in vivo gene expression data from a individual or cell specific gene expression data of an individual or host. Such data can be used to determine whether the therapeutic is effective in the individual based on the level of specific gene expression in a host. One embodiment provides a method including the steps of administering a therapeutic to a host, obtaining cells from the host, contacting the cells with a probe operably linked to a PTD and optionally to a targeting signal, wherein the probe includes a target recognition sequence complementary to a predetermined target polynucleotide, irradiating the cells with an exciting amount of radiation, and detecting electromagnetic emission from the cells in response to the exciting amount of radiation, and correlating the amount of detectable electromagnetic emission from the cells with amount of target polynucleotide in the cells. A therapeutic includes compounds, molecules, drugs or combinations thereof, administered to a host to treat, alleviated, mitigate; a pathology of the host or a symptom of a pathology.

Alternatively, one or more cells from a host can be contacted in vitro with an agent, for example a therapeutic agent, suspected of modulating expression of a target polynucleotide. Typically, the cells can be incubated for a period of time to allow the therapeutic agent to have a biological effect. The cells can then be contacted with the disclosed probes operably linked to a protein transduction domain, wherein the probes include a target recognition sequence complementary to the target polynucleotide. The cells containing the probes are irradiated with an exciting amount of radiation and electromagnetic emission from the cells emitted in response to the exciting mount of radiation can be detected. Emission from the cells exposed to the therapeutic agent and containing the probes can be compared with emissions from a control sample of cells containing the probes but which were not exposed to the therapeutic agent. A difference in emission between the cells exposed to the therapeutic agent and containing the probes compared with emissions from a control sample of cells containing the probes but which were not exposed to the therapeutic agent indicates that the therapeutic agent modulates expression of the target polynucleotide in the host. It will be appreciated by one of skill in the art that more than one probe specific for more than one target polynucleotide can be used to establish a profile of gene expression modulation by a particular agent or compound for an individual host. Such data can provide information to a medical practitioner to assist in determining course of treatment and use of specific medicines personalized to one individual or host. Typically, the agent or compound will be an agent believed to exert a therapeutic effect, i.e., treat or alleviate a pathology or symptom of a pathology.

Split Protein Probes

Figure 21:
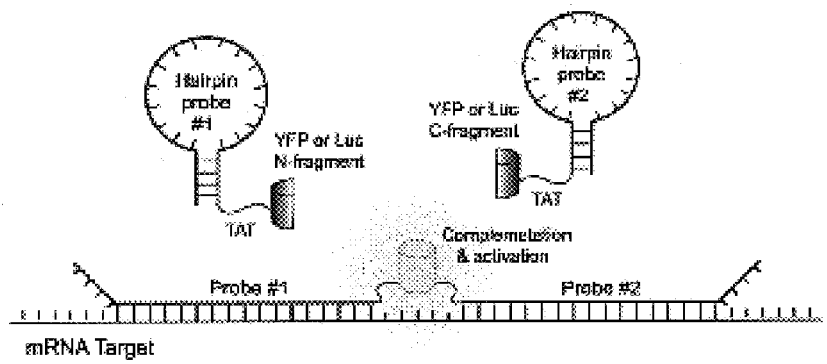
FIG. 21 shows an exemplary embodiment of a split protein probe.

FIG. 21 shows another exemplary embodiment of the disclosure. This embodiment provides activatable hairpin probe pairs comprising at least two polynucleotide stem-loop hairpins wherein each is conjugated with an N-terminal or C-terminal fragment of a reporter protein so that when both probes hybridize to adjacent regions of the same mRNA target, the two protein fragments reconstitute the fluorophore and generate a fluorescent signal upon excitation. Since each individual protein fragment is not fluorescent, no background signal is generated even if the hairpin probe is degraded by nucleases or opens nonspecifically due to nucleic acid binding proteins.

In one embodiment an exemplary set of dual-hairpin probes comprise fragments of yellow fluorescent protein variant, Venus. An exemplary molecular probes can contain complementary sequence in antisense orientation to the GAPDH mRNA: probe #1, 5'-GAGTCCTTCCACGATAC-CGACTC-3' (SEQ ID NO. 40); probe #2, 5'-CCACAT-GATGGCATGGACTGTGG-3' (SEQ ID NO. 41). Oligonucleotide-peptide conjugates containing a Cysteine with a free N-terminal can be prepared using published procedure of fragment coupling of pre-synthesized short peptides (such as CysGlyGly) to the 2'-position of a selected nucleotide through a stable amide linkage. Venus can be spliced into two halves (amino acids 1-154 and amino acids 155-238) that do not self-associate. Each fragment can be fused to an 11 amino acid TAT-delivery peptide at its C-terminus or at its N-terminus. The peptide can be linked to a hairpin probe through the thiol group. Expressed protein ligation can be used for conjugation between the fragments and oligonucleotide probes. This procedure has been used in the synthesis of a variety of modified proteins including covalent conjugates of proteins and polyamide nucleic acids (PNA). In the first step, the TAT peptide-linked N-terminal Venus fragment, fused to an intein and a chitin binding domain (CBD), is expressed in E. coli. This latter domain allows the affinity purification of the intein-fused fragment using a chitin matrix. Liberation from the column is achieved by mercaptoethansulfonic acid (MESNA), which produces a C-terminal thioester of the TAT peptide fused N-fragment of Venus. The peptide is then conjugated to hairpin probe #1 containing the N-terminal Cysteine. Hairpin probe #2 is conjugated with the TAT peptide-fused C-terminal fragment of Venus in a similar fashion.

It will be appreciated that other fluorescent proteins can be used with the disclosed probes. For example, luciferase protein fragments can be used to reconstitute the luciferase when both donor and acceptor probes are hybridized to the same target polynucleotide, resulting a bioluminescence signal.

Modified Nucleotide Linkages

Some embodiments provide probes including a plurality of nucleic acids or oligonucleotides containing modified backbones or non-natural internucleoside linkages. Exemplary modified backbones include those that retain a phosphorus atom in the backbone and those that do not have a phosphorus atom in the backbone.

Representative modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages are a 3' to 3', 5' to 5' or 2' to 2' linkage. Some oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050.

Some oligonucleotide backbones do not include a phosphorus atom therein and have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439.

In still other embodiments provide probes containing oligonucleotide mimetics in which both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al. (1991) Science 254:1497-1500.

Some embodiments provide probes having oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240.

In other embodiments, the probes may comprise modified oligonucleotides containing one or more substituted sugar moieties. Other modified oligonucleotides comprise one of the following at the 2' position: OH; F; O—, S—, or N-alkyl; O—, S—, or N-alkenyl; O—, S—, or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3]_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of the probe and other substituents having similar properties. Another modification includes 2'-methoxyethoxy (2'-O—$CH_2CH_2OCH_3$, also known as 2'-O-(2-methoxyethyl) or 2'-MOE) (Martin et al. (1995) Helv. Chim. Acta, 78, 486-504) i.e., an alkoxyalkoxy group. A further preferred modification includes 2'-dimethylaminooxyethoxy, i.e., a $O(CH_2)_2ON(CH_3)_2$ group, also known as 2'-DMAOE, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—$N(CH_3)_2$.

Other modifications include 2'-methoxy (2'-O—$CH_3$), 2'-aminopropoxy (2'-$OCH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. An exemplary 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, and each of which is herein incorporated by reference in its entirety.

A further modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in U.S. Pat. No. 6,268,490 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U) Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2 (3H)-one), phenothiazine cytidine (1H-pyrimido[5,4-b][1,4]benzothiazin-2 (3H)-one), G-clamps such as a substituted phenoxazine cytidine (e.g., 9-(2-aminoethoxy)-H-pyrimido [5,4-b][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases may be particularly useful for increasing the binding affinity of the oligomeric compounds of the disclosure. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2.degree. C. (Sanghvi, Y. S., Crooke, S. T. and Lebleu, B., eds., Antisense Research and Applications, CRC Press, Boca Raton, 1993. pp 276-278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121; 5,596,091; 5,614,617; 5,645,985; 5,830,653; 5,763, 588; 6,005,096; and 5,681,941, and each of which is herein incorporated by reference.

Fluorescence Energy Transfer

Some embodiments provide compositions that contain a reporter moiety whose reporting ability changes depending on whether the probe is bound to its complement or target polynucleotide. For example, some probes are designed to take advantage of quenching by energy transfer, for example fluorescence resonance energy transfer (FRET) or LRET (luminescence energy transfer) to detect and report binding to target molecules. Other embodiments do not include quenchers. In embodiments that do not include quenchers, the reporting ability changes depending on whether a donor probe hybridizes near the acceptor probe on the target polynucleotide. FRET is a highly distance-dependent interaction between a fluorescent reporter dye and a donor or quencher. Energy is transferred from one molecule (the donor) to the other (the reporter or the quencher). Additional examples of reporting abilities may also include the use of interchelating dyes conjugated to nucleic acid probes, such that there is significant increase/decrease in signal upon binding to target polynucleotide. Further examples may include the use of reporters which change the polarization state of emission energy upon binding to target polynucleotide.

As noted above, some embodiments of the disclosed probes include a pair of labels. Other embodiments provide probes that are labeled with a single label, for example a quantum dot or a reporter. The single labeled probes are designed to work together so that the donor on one probe transfers energy to the reporter on a second probe. Representative pairs of labels include, but are not limited to, at least one donor/quencher pair, for example a dye pair, or a dye and a non-dye quencher. In some embodiments, the pair of labels typically includes a fluorescent donor dye and a quencher for the donor fluorophore. In one embodiment, the labels are linked to a sequence or structure in the probe which does not hybridize directly to the target sequence.

The disclosed probes include any nucleic acid sequence or structure which can be labeled such that the presence of its complement or target polynucleotide indicates the presence of the target sequence. In one embodiment, the probe moiety is labeled with a donor or a reporter or a donor/quencher dye pair such that donor fluorescence is quenched prior to the sequence specific binding of the probe to the target polynucleotide, and such that quenching of donor fluorescence is reduced as an indication of the presence of the target. The disclosed probes may have a secondary structure such as a stem-loop (or hairpin) as described in U.S. Pat. No. 5,925,517 or a G-quartet as described in U.S. Pat. No. 5,691,145, or a random-coil (stem-less) structure. The secondary structure is labeled such that the donor and quencher are in close proximity when the secondary structure is folded, resulting in quenching of donor fluorescence. In the presence of a target, the secondary structure is unfolded in a target-dependent reaction so that the distance between the donor and quencher is increased. This decreases quenching and produces an increase in donor fluorescence which can be detected as an indication of the presence of the target sequence.

For efficient FRET quenching to take place the fluorophore and quencher molecules are typically less than about 100 Å apart. In some embodiments, the absorption spectrum of the quencher overlaps with the emission spectrum of the fluorophore. Many donor/quencher dye pairs known in the art are useful in some embodiments of the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others.

For energy transfer quenching mechanisms donor/quencher pairs can be selected so that the emission wavelengths of the donor fluorophore overlap the excitation wavelengths of the quencher or reporter, i.e., there must be sufficient spectral overlap between the two dyes to allow efficient energy transfer, charge transfer or fluorescence quenching. P-(dimethyl aminophenylazo) benzoic acid (DABCYL) is a non-fluorescent quencher dye which effectively quenches fluorescence from an adjacent fluorophore, e.g., fluorescein or 5-(2'-aminoethyl) aminonaphthalene (EDANS).

Any dye pair which produces fluorescence quenching in the disclosed probes are suitable for use in the disclosed methods, regardless of the mechanism by which quenching occurs. Terminal and internal labeling methods are also known in the art and may be routinely used to link the donor and quencher dyes at their respective sites in the probe.

Protein Transduction Domains

As noted above, certain embodiments of the present disclosure also include probes operably linked to a protein transduction domain. Several small regions (9-16 amino acids) of proteins called protein transduction domains (PTDs) or cell penetrating peptides (CPPs) that confer the ability to traverse biological membranes efficiently. Without wishing to be bound by any one theory, it is believed that some PTDs are able to cross a cell membrane in a receptor-independent mechanism (Kabouridis, P. (2003) Trends in Biotechnology 21(11):498-503). Although several of PTDs have been documented, the two most commonly employed PTDs are derived from TAT protein of HIV (Frankel and Pabo (1988) Cell 55(6):1189-93) and Antennapedia transcription factor from *Drosophila*, whose PTD is known as Penetratin (Derossi et al. (1994) J Biol. Chem. 271(30): 18188-93).

The Antennapedia homeodomain is 68 amino acid residues long and contains four alpha helices. Penetratin is an active domain of this protein which consists of a 16 amino acid sequence derived from the third helix of Antennapedia. (Fenton et al. (1998) J Immunol Methods 212(1):41-8). TAT protein consists of 86 amino acids and is involved in the replication of HIV-1. The TAT PTD consists of an 11 amino acid sequence domain (residues 47 to 57; YGRKKRRQRRR (SEQ ID NO. 38) of the parent protein that appears to be critical for uptake (Vives et al. (1997) J Biol. Chem. 272 (25):16010-7). Additionally, the basic domain Tat(49-57) or RKKRRQRRR (SEQ ID NO. 39) (Wender et al. (2000) Proc Natl Acad Sci USA. 97(24):13003-8) has been shown to be a PTD. In the current literature TAT has been favored for fusion to proteins of interest for cellular import. Several modifications to TAT, including substitutions of Glutatmine to Alanine, i.e., Q to A, have demonstrated an increase in cellular uptake anywhere from 90% (Wender et al. (2000) Proc Natl Acad Sci USA. 97(24):13003-8) to up to 33 fold in mammalian cells. (Ho et al. (2001) Cancer Res. 61(2): 474-7) The most efficient uptake of modified proteins was revealed by mutagenesis experiments of TAT-PTD, showing that an 11 arginine stretch was several orders of magnitude more efficient as an intracellular delivery vehicle. Thus, some embodiments include PTDs that are cationic or amphipathic. Additionally exemplary PTDs include but are not limited to poly-Arg-RRRRRRR (SEQ ID NO. 42); PTD-5-RRQRRTSKLMKR (SEQ ID NO. 43); Transportan GWTLNSAGYLLGKINLKALMLAKKIL (SEQ ID NO. 44); KALA-WEAKLAKALAKALAKHLAKALAKALKCEA (SEQ ID NO. 45); DAATATRGRSMSRPTERPRAPARSASRPRRPVE (SEQ ID NO. 46), and RQIKIWFQNRRMKWKK (SEQ ID NO. 47).

The disclosed probes can have the protein transduction domain linked directly or indirectly to the polynucleotide. One embodiment provides a probe having a modified monomer, such as a nucleotide, to facilitate linking chemistries. The monomer can be modified with a reactive group such as an amine, carbonyl, carboxyl, and thiol or have a biotin group attached to the nucleotide. Such modified monomers are known in the art, and are commercially available and include modified nucleotides such as dT (Link Technologies, Scotland, UK). The protein transduction domain can be directly linked using conventional linking chemistry to the modified nucleotide or can be indirectly linked to the amine modified nucleotide using a linker or spacer group. The linker group can be linked to the modified nucleotide at one end, and linked to the PTD on the other end.

In another embodiment, the protein transduction domain is operably linked to the probe using a streptavidin-biotin linkage. The probe includes a modified monomer, for example biotin-dT, in the region of the probe that is not complementary to the target polynucleotide, for example to the quencher arm of the stem. The linkage can be through a carbon linker. Protein transduction domains can be modified to include a biotin moiety. The modified PTD and the modified probe can then be linked through a streptavidin molecule.

In another embodiment, a thiol-maleimide linkage is used to link the PTD to the probe. In one aspect, the non-complementary region of the probe, for example, the stem region, in particular the stem region linked to a quencher, is modified by adding a thiol group to a monomer of the probe. The thiol group can react with a maleimide group placed at the C terminus of the PTD or targeting signal to form a linkage, in particular a direct and stable linkage.

Another embodiment incorporates a cleavable disulfide bridge in which the PTD or targeting signal is modified by adding a cysteine residue at the C terminus which forms a disulfide bridge with the thiol-modified probe. This disulfide bridge design allows the PTD or targeting signal to be cleaved from the probe by the reducing environment of the cytoplasm.

Another embodiment allows for combined synthesis of the delivery peptide sequence along with the probe, for example, in the case of a PNA probe, where both the delivery peptide and the nucleic acid probe sequence can be generated using a single peptide. Further the linkage between the delivery peptide and the nucleic acid probe can be tailored to allow for specific cleavage using reducing disulfide bridge or using enzymatic cleavage sites in the linkage.

Another embodiment allows for indirect linkage of the probe with delivery peptide, e.g., the delivery vehicle itself may be dendrimer-based or lipid-based such as liposomes/polymeric or any combination of the above, in which nucleic acid probes are packaged inside the delivery vehicle, with delivery peptides attached to the surface of such construct. The attached delivery peptides (single or multiple types) may allow efficient delivery of the probes to a specific organ, tissue, cell type or subcellular compartment.

Linkers

The disclosed probes can be linked to a protein transduction domain or targeting signal via a linker or spacer. The linker can be one or more monomer units including atoms, amino acids, nucleic acids, sugars, or natural or synthetic polymer monomers. Generally, the linker is composed of monomers that are substantially inert or do not otherwise chemically react once coupled to the probe. Representative linkers include alkyl linkers of 1 to 12 carbons, typically about 6 carbons. The alkyl groups of the linker can be substituted, for example with alkyl or aryl groups, heterocycles, halogens, and the like. The number of monomers of the linker can vary, however, the linker should have enough monomers to prevent the protein transduction domain or targeting signal from sterically interfering with the binding of the probe to its target polynucleotide. Typically, the linker is modified to link the protein transduction domain or target signal via conventional linking chemistry.

The linkers can be linked with or contain cleavable bonds, for example photo cleavable, thermally cleavable, or enzymatically cleavable bonds. Such bonds are known in the art. Upon entry into the cell, the cleavable bond can be cleaved. The cleavage of the bond can result in the separation of the PTD or targeting signal or both from the probe.

Linking Chemistry

Of the various linking chemistries that can be used to link molecules with other molecules or reagents, the most common are amine, carbonyl, carboxyl, and thiol. It will be appreciated by those of skill in the art, that any linking chemistry may be utilized. Indirect crosslinking of the amines in one molecule to the thiols in a second molecule is the predominant method for forming a heteroconjugate. If the probe, the linker, or the protein transduction domain does not already contain one or more thiol groups, the thiol groups can be introduce using a thiolation procedure.

Thiol groups (also called mercaptans or sulfhydryls) are present in cysteine residues of proteins. Thiols can also be generated by selectively reducing cystine disulfides with reagents such as dithiothreitol (DTT) or -mercaptoethanol. Removal of DTT or -mercaptoethanol is sometimes accompanied by air oxidation of the thiols back to the disulfides. Reformation of the disulfide bond can be avoided by using the reducing agent tris-(2-carboxyethyl)phosphine (TCEP), which does not contain thiols. TCEP is generally impermeable to cell membranes and to the hydrophobic protein core, permitting its use for the selective reduction of disulfides that have aqueous exposure. The pH-insensitive and less polar phosphine derivative tris-(2-cyanoethyl)phosphine may yield greater reactivity with buried disulfides.

Several methods are available for introducing thiols into molecules, including the reduction of intrinsic disulfides, as well as the conversion of amine, aldehyde or carboxylic acid groups to thiol groups. Disulfide crosslinks, for example of cystines in proteins, can be reduced to cysteine residues by dithiothreitol, tris-(2-carboxyethyl)phosphine or tris-(2-cyanoethyl)phosphine.

Amines can be indirectly thiolated by reaction with succinimidyl 3-(2-pyridyldithio)propionate, followed by reduction of the 3-(2-pyridyidithio)propionyl conjugate with DTT or TCEP. Alternatively, amines can be indirectly thiolated by reaction with succinimidyl acetylthioacetate, followed by removal of the acetyl group with 50 mM hydroxylamine or hydrazine at near-neutral pH.

Thiols can also be incorporated at carboxylic acid groups by an EDAC-mediated reaction with cystamine, followed by reduction of the disulfide with DTT or TCEP. Tryptophan residues in thiol-free proteins can be oxidized to mercaptotryptophan residues, which can then be modified by iodoacetamides or maleimides.

Thiol-reactive functional groups are primarily alkylating reagents, including iodoacetamides, maleimides, benzylic halides and bromomethylketones. Arylating reagents such as NBD halides react with thiols or amines by a similar substitution of the aromatic halide. Reaction of any of these functional groups with thiols usually proceeds rapidly at or below room temperature in the physiological pH range (pH 6.5-8.0) to yield chemically stable thioethers.

Thiols also react with many of the amine-reactive reagents described in including isothiocyanates and succinimidyl esters. Although the thiol-isothiocyanate product (a dithiocarbamate) can react with an adjacent amine to yield a thiourea, the dithiocarbamate is more likely to react with water, consuming the reactive reagent without forming a covalent adduct.

Iodoacetamides readily react with all thiols, including those found in peptides, proteins and thiolated polynucleotides, to form thioethers. Iodoacetamides can sometimes react with methionine residues. They may also react with histidine or tyrosine, but generally only if free thiols are absent. Although iodoacetamides can react with the free base form of amines, most aliphatic amines, except the amino group at a protein's N-terminus, are protonated and thus relatively unreactive below pH 8. In addition, iodoacetamides react with thiolated oligonucleotide primers, as well as with thiophosphates and thiouridine residues present in certain nucleic acids, but usually not with the common nucleotides.

Iodoacetamides are intrinsically unstable in light, especially in solution; reactions should therefore be carried out under subdued light. Adding cysteine, glutathione or mercaptosuccinic acid to the reaction mixture will quench the reaction of thiol-reactive probes, forming highly water-soluble adducts that are easily removed by dialysis or gel filtration. Although the thioether bond formed when an iodoacetamide reacts with a protein thiol is very stable, during amino acid hydrolysis the bioconjugate loses its fluorophore to yield S-carboxymethylcysteine.

Maleimides are excellent reagents for thiol-selective modification, quantitation and analysis. The reaction involves addition of the thiol across the double bond of the maleimide to yield a thioether. Maleimides apparently do not react with methionine, histidine or tyrosine. Reaction of maleimides with amines usually requires a higher pH than reaction of maleimides with thiols. Hydrolysis of maleimides to a mixture of isomeric nonreactive maleamic acids can compete significantly with thiol modification, particularly above pH 8. Furthermore, maleimide adducts can hydrolyze or they can ring-open by nucleophilic reaction with an adjacent amine to yield crosslinked products. This latter reaction can potentially be enhanced by raising the pH above 9 after conjugation.

For example, a disulfide-containing linker or spacer, including but not limited to an alkyl linker or spacer of about 1 to about 12 carbon atoms, is photo- or thermally coupled to the target nucleobase or polynucleotide using conventional chemistry, for example azide chemistry. The disulfide bond is reduced, yielding a free thiol. A covalent bond is formed between the reagent thiol and a thiol-reactive linker, hapten, fluorochrome, sugar, affinity ligand, or other molecule.

The linking of two molecules can be achieved using heterobifunctional crosslinkers. Representative heterobifunctional crosslinkers include, but are not limited to, p-maleimidophenyl isocyanate; succinimidyl acetylthioacetate; succinimidyl-trans-4(maleimidylmeythyl)-cyclohexane-1carboxylate (SMCC); succinimidyl acetylthioacetate (SATA); succinimidyl 3-(2-pyridyldithio)propionate (SPDP); N-((2-pyridyldithio)ethyl)-4-azidosalicylamide (PEAS; AET); 4-azido-2,3,5,6-tetrafluorobenzoic acid, succinimidyl ester (ATFB, SE); 4-azido-2,3,5,6-tetrafluorobenzoic acid, STP ester, sodium salt (ATFB, STP ester); 4-azido-2,3,5,6-tetrafluorobenzyl amine, hydrochloride; benzophenone-4-isothiocyanate; benzophenone-4-maleimide; 4-benzoylbenzoic acid, succinimidyl ester. The heterobifunctional crosslinkers can be photoreactive, amine and/or thiol reactive, or aldehyde/ketone reactive, or a combination thereof.

Targeting Signals

The disclosed probes can also include targeting signals or domains that target the probe to a specific cell, tissue or organ as well as specific intracellular locations or organelles. Such target signals are known in the art. For example, nuclear targeting signals can be found in the Nuclear Localization Signal Database at http://cubic.bioc.columbia.edu/db/NLSdb/ which is incorporated by reference herein in its entirety.

Representative nuclear localization signals include, but are not limited to, SV 40 T antigen or a fragment thereof, such as PKKKRKV (SEQ ID NO. 48). The NLS can be simple cationic sequences of about 4 to about 8 amino acids, or can be bipartite having two interdependent positively charged clusters separated by a mutation resistant linker region of about 10-12 amino acids. Additional representative NLS include but are not limited to GKKRSKV (SEQ ID NO. 49); KSRKRKL (SEQ ID NO. 50); KRPMTKKAGQAKKKKLDK (SEQ ID NO. 51); RKKRKTEEESPLKDKAKKSK (SEQ ID NO. 52); KDCVMNKHHRNRCQYCRLQR (SEQ ID NO. 53); PMKRVKLD (SEQ ID NO. 54); and KKYENWIKRSPRKRGRPRK (SEQ ID NO. 55).

The targeting signal can also target the probe to the mitochondria which are also known in the art. Representative mitochondrial targeting signals include, but are not limited to include the mitochondrial localization signal of subunit VIII of human cytochrome oxidase, the yeast cytochrome c oxidase subunit IV presequence and the aminoterminal leader peptide of the rat ornithine-transcarbamylase.

The identification of the specific sequences necessary for translocation of a linked probe into a chloroplast or mitochondria can be determined using predictive software known to those skilled in the art, including the tools located at http://www.mips.biochem.mpg.de/cqi-bin/proi/medgen/mitofilter.

Targeting signals can also include vitamins such as folate to target the probes to cells having a high number of folate receptors, including but not limited to, cancer cells. Asialoglycoprotein receptor ligands can also be linked to the disclosed probes to target them to the liver. For example, N-acetylgalactosamine containing peptides, asialoorosomucoid, and galactoside-containing cluster ligands can be used.

Targeting sequences can also be synthetic small molecules/ligands with high affinity for specific compartments in addition to specific localizing sequences, e.g. mitochondria can be targeted using amphiphilic synthetic molecules.

Dual Labeled Probes

One embodiment provides a composition for the detection of a target polynucleotide comprising, a first nucleic acid probe that hybridizes to a first nucleic acid target sequence on the target polynucleotide, forms a stem-loop structure when not bound to the first nucleic acid target sequence, and incorporates a energy transfer donor moiety. This embodiment of the disclosure further provides a second nucleic acid probe that hybridizes to a second nucleic acid target sequence on the target polynucleotide, forms a stem-loop structure when not bound to the second nucleic acid target sequence, and incorporates a energy transfer acceptor moiety. The disclosure provides that the first nucleic acid target sequence and the second nucleic acid target sequence are separated by a number of nucleotides on the target polynucleotide such that a energy transfer signal from interaction between the donor moiety of the first nucleic acid probe and the acceptor moiety of the second nucleic acid probe can be detected to determine hybridization of both the first nucleic acid probe and the second nucleic acid probe to the target polynucleotide. Preferably, the energy transfer signal is a florescent or luminescent signal.

In an alternative embodiment, the disclosure provides a first nucleic acid probe that hybridizes to a first nucleic acid target sequence on the target polynucleotide, and incorporates a luminescence energy transfer lanthanide chelate donor moiety; and second nucleic acid probe that hybridizes to a second nucleic acid target sequence on the target polynucleotide, and incorporates an organic energy transfer acceptor moiety, wherein the first nucleic acid target sequence and the second nucleic acid target sequence are separated by a number of nucleotides on the target polynucleotide such that a luminescence energy transfer signal from interaction between the lanthanide chelate donor moiety of the first nucleic acid probe and the acceptor moiety of the second nucleic acid probe can be detected to determine hybridization of both the first nucleic acid probe and the second nucleic acid probe to the target polynucleotide. In certain embodiments of this disclosure, the first nucleic acid probe or second nucleic acid probe is linear or randomly coiled when not hybridized to the first or second nucleic acid target sequences, respectively. In other embodiments of this disclosure, the first nucleic acid probe or second nucleic acid probe forms a stem-loop structure when not hybridized to the first or second nucleic acid target sequences, respectively.

In certain one embodiment of the disclosure, the first nucleic acid probe further incorporates a quencher moiety, such that an interaction between the donor moiety of the first nucleic acid probe and the quencher moiety can be detected to differentiate between the first nucleic acid probe in the stem-loop (or random-coil) structure and non-stem-loop (or non-random-coil) structure. Similarly, in other embodiments, the second nucleic acid probe further incorporates a quencher moiety, such that an interaction between the acceptor moiety of the second nucleic acid probe and the quencher moiety can be detected to differentiate between the second nucleic acid probe in the stem-loop (or random-coil) structure and non-stem-loop (or non-random-coil) structure. In embodiments utilizing a quencher moiety on a nucleic acid probe, the disclosure provides that the quencher moiety can be selected from, for example, dabcyl quencher, black hole quencher or Iowa Black quencher or other moieties well-known in the art to change the energy transfer wavelength emission of an unquenched donor or acceptor moiety.

In certain other embodiments, the first nucleic acid probe further incorporates a energy transfer moiety pair, such that a energy transfer signal from interaction between the donor moiety and the acceptor moiety on the first nucleic acid probe can be detected to differentiate between the first nucleic acid probe in the stem-loop structure and non-stem-loop structure. Similarly, other embodiments provide that the second nucleic acid probe further incorporates a energy transfer moiety pair, such that a energy transfer signal from interaction between the donor moiety and the acceptor moiety on the second nucleic acid probe can be detected to differentiate between the second nucleic acid probe in the stem-loop structure and non-stem-loop structure.

In various embodiments, the first nucleic acid target and the second nucleic acid target are separated by 1 to 20 nucleotides, or separated by 2, 3, 4, 5, 6, 7, 8, 9, 10, 11, 12, 13, 14, or 15 nucleotides. As discussed below, the preferred number of separating nucleotides will vary depending upon the energy transfer source used, and can be routinely determined by one of skill in the art in view of the present disclosure.

In one embodiment, the resonance energy signals are due to fluorescence resonance energy transfer (FRET) or luminescence resonance energy transfer (LRET). In embodiments wherein the energy transfer signal is due to fluorescence energy transfer, the donor moiety can be for example a 6-Fam fluorophore. In embodiments wherein the energy transfer signal is due to fluorescence energy transfer, the acceptor moieties can be Cy-3, ROX or Texas Red. Additional examples of FRET donor and acceptor moieties useful in the present disclosure are provided below.

In other embodiments, the energy transfer signal is due to luminescence energy transfer (LRET) and the donor moiety is a lanthanide chelate. In some one embodiment where the resonance energy signal is due to LRET, the donor moiety can be Europium or Terbium. Furthermore, in some embodiments where the resonance energy signal is due to LRET, the donor moiety can be a lanthanide chelate such as DTPA-cytosine, DTPA-cs124, BCPDA, BHHCT, Isocyanato-EDTA, Quantum Dye, or W1024 and the acceptor moiety can be Cy-3, ROX or Texas Red. In some embodiments, due to the range of effective energy transfer of the lanthanide chelate, multiple acceptor moieties may be employed. The donor moiety can be a lanthanide chelate and the acceptor moiety can be a phycobiliprotein. In certain embodiments, the phycobiliprotein is Red Phycoerythrin (RPE), Blue Phycoerythrin (BPE), or Allophycocyanin (APC). Additional examples of LRET donor and acceptor moieties useful in the present disclosure are provided below.

In certain embodiments, the disclosure provides that the first or second nucleic acid probes each comprise from 5 to 50 nucleotides, 10 to 40 nucleotides, or 15, 16, 17, 18, 19, 20, 21, 22, 23, 24, 25, 26, 27, 28, 29 or 30 nucleotides. In other one embodiment, the nucleic acid probes comprise a 2'-O-methyl nucleotide backbone, among many alternative or synthetic nucleotides, described below. The disclosure further provides that one end of the first and/or the second nucleic acid probes participates in both stem-loop formation and hybridization to the target polynucleotide. Such embodiments are referred to herein as a shared-stem molecular beacon, or probe, herein, and are described in more detail below, particularly in Example 2.

In additional embodiments, the disclosure provides methods for detecting a target polynucleotide, comprising combining the composition described herein with a sample suspected of containing a target polynucleotide, and detecting hybridization by differential energy transfer signal to determine the presence or absence, and/or the expression level of the target polynucleotide in the sample in vitro or in vivo. In some one embodiment, the methods can be performed in vivo. Therefore, in a preferred embodiment of this method, the sample contains a living cell. The disclosure provides that the methods may be performed with samples comprising cell lysates, tissue extracts, living tissues and cells that are taken out of the body, or that remain in situ.

The methods of the present disclosure further include detection of changes in the levels of expression of a nucleic acid target, or in RNA transcript, such that alterations of gene expression can be monitored as a result of the dose-dependent cellular response to external stimuli, such as drug molecules, hormones, growth factors, temperature, shear flow, or microgravity, for example. The disclosure further provides that the compositions can be used to visualize, i.e., through fluorescence or luminescence, the location and relative amount of gene expression in tissues and cells.

In diagnostic or prognostic detection methods the target polynucleotide can comprise a genetic point mutation, deletion, or insertion relative to a naturally occurring or control nucleic acid. Such screening methods can permit the detection of the target polynucleotide indicating the presence of a genetically associated disease, such as certain cancers, in the sample. There are many well-known examples of genetic mutations already in the art that are indicative of a disease state. The methods include the detection of nucleic acids comprising K-ras, survivin, p53, p16, DPC4, or BRCA2. Furthermore, the methods can be used to detect the amount of a target polynucleotide being produced by an organism for purposes other than diagnosis or prognosis of a disease or condition. Energy transfer detections of the present disclosure can be performed with the assistance of single- or multiple-photon microscopy, time-resolved fluorescence microscopy or fluorescence endoscopy, as detailed below.

The disclosure further provides kits for the detection of a target polynucleotide comprising the nucleic acid probe compositions described herein, necessary reagents and instructions for practicing the methods of detection. Such alternative compositions, methods and kits therefor are described in more detail by way of the examples, and still others will be apparent to one of skill in the art in view of the present disclosure.

Figure 11:
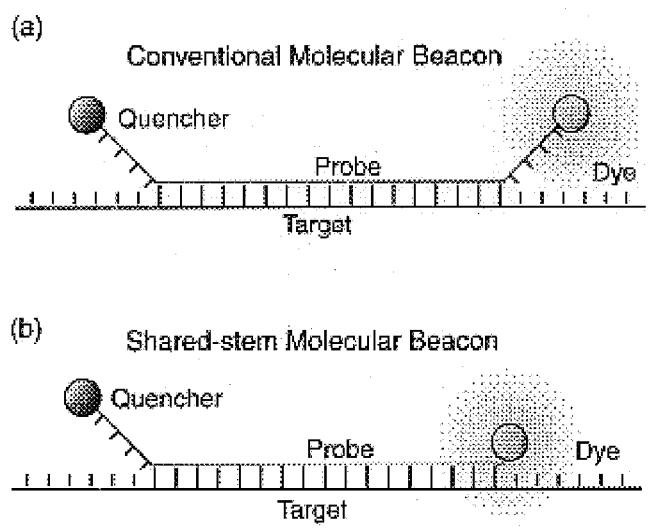
FIGS. 11a and 11b shows alternative molecular beacon designs.

One embodiment of the present disclosure provides compositions and methods that measure a energy transfer, for example, a fluorescent signal due to FRET or LRET as a result of direct interaction between two molecular beacons when hybridized to the same target polynucleotide of interest. This method can dramatically reduce false-positive signals in gene detection and quantification in living cells. As shown in FIG. 1 and alternatively in FIG. 11, this approach utilizes a pair of molecular beacons, one with a donor fluorophore and a second with an acceptor fluorophore. Probe sequences are chosen such that the molecular beacons hybridize adjacent to each other on a single nucleic acid target in a way that positions their respective fluorophores in optimal configuration for FRET (Mergny et al., 1994; Sixou et al. 1994). Emission from the acceptor fluorophore serves as a positive signal in the FRET based detection assay.

If acceptor and donor fluorophores are well matched, excitation of the donor can be achieved at a wavelength that has little or no capacity to excite the acceptor; excitation of the acceptor will therefore only occur if both molecular beacons are hybridized to the same target polynucleotide and FRET occurs. Molecular beacons that are degraded or open due to protein interactions will result in the presence of unquenched fluorophore, however, fluorescence emitted from these species is different in character from the signal obtained from donor/acceptor FRET pair, making background and true positive signal more readily differentiated. Thus, by detecting FRET instead of direct single-molecule fluorescence, nucleic acid probe/target binding events can be distinguished from false-positives.

In contrast to prior labeling of two linear oligonucleotide probes with donor and acceptor fluorophores, the stem-loop hairpin structure of molecular beacons offers further reduction in background fluorescence as well as enhanced specificity, which is helpful particularly when detection of allelic variants or point mutations is desired.

Further benefit from another embodiment of the dual energy transfer molecular beacons and method of the present disclosure can be achieved by employing an oligonucleotide probe with a lanthanide chelate as the donor and a molecular beacon with a traditional organic fluorophore as the acceptor (reporter) moiety. In contrast to organic fluorophores that have a fluorescence lifetime of ~10 ns, lanthanide chelates can have emission lifetimes greater than 1 ms. The mechanism that is responsible for the long lifetime emission of lanthanide chelates is complex and involves energy transfer from the triplet state of the aromatic ligand. Specifically, upon excitation the ligand is excited to its singlet state and then undergoes an intersystem transition to its triplet state, whereas the energy is either quenched by water molecules or transferred to the lanthanide ion. Fluorescence is then emitted from the lanthanide ion as it returns to the ground state (Lemmetyinen et al., 2000). Since such fluorescence emission does not result from a singlet-to-singlet transition, the use of lanthanide chelates as a donor results in luminescent energy transfer (LRET). Therefore, by using pulse excitation and time-gating techniques, it is possible to selectively record emission after the background fluorescence from organic dyes, scattering, and autofluorescence has decayed. The only signals remaining in this long-time domain are the emission from the lanthanide chelate and from acceptor fluorophores that have participated in LRET. In this case the narrow emission peaks of a lanthanide chelate render the background fluorescence close to zero at certain wavelengths, leading to extremely large signal-to-background ratio. The donor probe in a LRET pair can be a simple linear probe, i.e., neither quencher nor hairpin structure are necessary.

Furthermore, the disclosure provides a design variant for molecular beacons where one arm of the stem participates in both hairpin formation and target hybridization, referred to herein as "shared-stem" molecular beacons. In contrast, conventional molecular beacons are designed such that the loop sequence is complementary to the target while the stem sequences are self-complementary but unrelated to the target sequence. This new design offers certain advantages over conventional molecular beacon design, especially in two-probe fluorescence energy transfer, for example fluorescence resonance energy transfer (FRET) assays. The disclosure provides the thermodynamic and kinetic properties of both shared-stem and conventional molecular beacons and makes a systematic comparison between them. In particular, the present description quantifies the changes in enthalpy and entropy upon the formation of probe/target duplexes as determined by the probe and stem lengths. Further provided herein is a study of the melting behavior, specificity, and hybridization on-rate depend on the stem length of molecular beacons, such that one of skill in the art may make and use a variety of embodiments to suit the specific purposes of each situation.

The nucleic acid probes of the disclosure utilize the principle of energy transfer between a donor moiety and an acceptor moiety. In a preferred embodiment, the energy transfer is fluorescence energy transfer, for example fluorescence resonance energy transfer (FRET), in which the first and second probes are labeled with donor and acceptor moieties, respectively, wherein the donor moiety is a fluorophore and the acceptor moiety may be a fluorophore, such that fluorescent energy emitted by the donor moiety is absorbed by the acceptor moiety when both probes are hybridized to the first and second target sequences respectively on the same nucleic acid subject. In one embodiment of the present disclosure, the acceptor moiety is a fluorophore that releases the energy absorbed from the donor at a different wavelength; the emissions of the acceptor may then be measured to assess the progress of the hybridization reaction.

In a preferred embodiment, the probe is a hairpin stem-loop structure (often referred to in the art as a molecular beacon) that contains either a donor or acceptor moiety and optionally a quencher moiety, such that the quencher moiety reduces the fluorescence of the donor or acceptor when the probe is in the stem-loop structure (i.e., not hybridized). When the probe is hybridized to the target polynucleotide in this embodiment, its conformation changes, eliminating the quenching effect, and the resulting fluorescence of the donor or acceptor moiety may be detected. In certain cases, the probe has a random-coil (stem-les) structure.

In an alternative embodiment, the present disclosure provides a nucleic acid probe that forms a hairpin stem-loop (or a random-coil) structure in which energy transfer will decrease when the probe is hybridized with the target polynucleotide. In such an embodiment, the quencher moiety on the first probe is replaced with a reciprocating moiety to form a energy transfer moiety pair, and the differential in energy transfer is detectable between the hairpin stem-loop structure and a non-stem-loop structure. Alternatively, the quencher moiety on the second probe is replaced with a reciprocating moiety to form a energy transfer moiety pair, and the differential in energy transfer is detectable between the hairpin stem-loop structure and a non-stem-loop structure. In such embodiments of the present disclosure, a third energy transfer moiety pair forms by the dual probes, a donor moiety on the first probe, and an acceptor moiety on the second probe, such that the energy transfer signal due to the interaction of donor and acceptor may be measured to assess the progress of the hybridization reaction of both probes on the target polynucleotide.

One aspect of the disclosure pertains to nucleic acids sufficient for use as hybridization probes for the identification of a target polynucleotide (e.g., DNA or mRNA). As used herein, the term "nucleic acid" is intended to include DNA molecules (e.g., cDNA or genomic DNA) and RNA molecules (e.g., mRNA) and analogs of the DNA or RNA generated using nucleotide analogs. As referred to herein, nucleic acids that are "complementary" can be perfectly or imperfectly complementary, as long as the desired property resulting from the complementarity is not lost, e.g., ability to hybridize.

The nucleic acids of the present disclosure may be substantially isolated or alternatively unpurified. An "isolated" or "purified" nucleic acid is one that is substantially separated from other nucleic acid molecules that are present in the natural source of the nucleic acid. Preferably, an "isolated" nucleic acid is substantially free of sequences that naturally flank the nucleic acid (i.e., sequences located at the 5' and 3' ends of the nucleic acid) in the genomic DNA of the organism from which the nucleic acid is derived. Moreover, an "isolated" nucleic acid molecule can be substantially free of other cellular material, or culture medium when produced by recombinant techniques, or chemical precursors or other chemicals when chemically synthesized. (see, Sambrook et al. 2001, *Molecular Cloning: A Laboratory Manual.* 3rd, ed., *Cold Spring Harbor Laboratory*, Cold Spring Harbor Laboratory Press, Cold Spring Harbor, N.Y.).

The probe typically comprises substantially purified nucleic acid. The nucleic acid probe typically comprises a region of nucleotide sequence that hybridizes to at least about 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 consecutive nucleotides of a target polynucleotide. The target polynucleotide can be a sense strand of one of the target polynucleotide sequences, an anti-sense sequence, or naturally occurring mutants thereof. Preferably, the nucleic acid target is an mRNA.

Probes based on the nucleotide sequences can be used to detect or amplify transcripts or genomic sequences encoding the same or homologous proteins. In other embodiments, the probe further comprises a label group attached thereto, e.g., the label group can be a radioisotope, an enzyme, or an enzyme co-factor. Such probes can be used as a part of a genomic marker test kit for identifying cells which express a particular protein, such as by measuring a level of the protein-encoding nucleic acid in a sample of cells, e.g., detecting the target polynucleotide mRNA levels or determining whether the gene encoding the mRNA has been mutated or deleted.

In an additional preferred embodiment, an isolated nucleic acid molecule of the disclosure comprises a nucleic acid probe sequence that hybridizes, e.g., hybridizes under stringent conditions, to a target nucleotide sequence of interest. These hybridization conditions include washing with a solution having a salt concentration of about 0.02 molar at pH 7 at about 60° C. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 65%, more preferably at least about 70%, and even more preferably at least about 75% or more homologous to each other typically remain hybridized to each other. Such stringent conditions are known to those skilled in the art and can be found in *Current Protocols in Molecular Biology*, John Wiley & Sons, N.Y. (1989) 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1% SDS at 50-65° C. As used herein, a "naturally-occurring" nucleic acid molecule refers to an RNA or DNA molecule having a nucleotide sequence that occurs in nature (e.g., encodes a natural protein).

Nucleic acid probes of the disclosure may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (1988, Nucl. Acids Res. 16:3209), methylphosphonate oligonucleotides can be prepared by use of controlled pore glass polymer supports (Sarin et al., 1988, Proc. Natl. Acad. Sci. U.S.A. 85:7448-7451), etc.

Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining oligonucleotide that has been separated on an acrylamide gel, or by measuring the optical density at 260 nm in a spectrophotometer.

Nucleic acid probes of the disclosure may be labeled with donor and acceptor moieties during chemical synthesis or the label may be attached after synthesis by methods known in the art. In a specific embodiment, the following donor and acceptor pairs are used: a luminescent lanthanide chelate, e.g., terbium chelate or lanthanide chelate, is used as the donor, and an organic dye such as fluorescein, rhodamine or CY-5, is used as the acceptor. Preferably, terbium is used as a donor and fluorescein or rhodamine as an acceptor, or europium is used as a donor and CY-5 as an acceptor. In another specific embodiment, the donor is fluorescent, e.g. fluorescein, rhodamine or CY-5, and the acceptor is luminescent, e.g. a lanthanide chelate. In yet another embodiment, the energy donor is luminescent, e.g., a lanthanide chelate, and the energy acceptor may be non-fluorescent.

In another specific embodiment, the donor moiety is a fluorophore. In another specific embodiment, both donor and acceptor moieties are fluorophores. Suitable moieties that can be selected as donor or acceptors in FRET pairs are set below:

4-acetamido-4'-isothiocyanatostilbene-2,2'disulfonic Acid
Acridine and Derivatives:
acridine
   acridine isothiocyanate
5-(2'-aminoethyl)aminonaphthalene-1-sulfonic acid (EDANS)
4-amino-N-[3-vinylsulfonyl)phenyl]naphthalimide-3,5disulfonate(LuciferYellow VS)
N-(4-anilino-1-naphthyl)maleimide
Anthranilamide
Brilliant Yellow Coumarin and Derivatives:
coumarin
7-amino-4-methylcoumarin (AMC, Coumarin 120)
7-amino-4-trifluoromethylcoumarin (Coumarin 151)
cyanosine
4'-6-diaminidino-2-phenylindole (DAPI)
5',5"-dibromopyrogallol-sulfonephthalein (Bromopyrogallol Red)
7-diethylamino-3-(4'-isothiocyanatophenyl)-4-methylcoumarin diethylenetriamine pentaacetate
4-(4'-diisothiocyanatodihydro-stilbene-2,2'-disulfonic acid
4,4'-diisothiocyanatostilbene-2,2'-disulfonic acid
5-[dimethylamino]naphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)

Eosin and Derivatives:
eosin
eosin isothiocyanate

Erythrosin and Derivatives:
erythrosin B
erythrosin isothiocyanate
ethidium

Fluorescein and Derivatives:
5-carboxyfluorescein (FAM)
5-(4,6-dichlorotriazin-2-yl)aminofluorescein (DTAF)
2'7'-dimethoxy-4'5'-dichloro-6-carboxyfluorescein (JOE)
fluorescein
fluorescein isothiocyanate
QFITC (XRITC)
fluorescamine
IR144
IR1446
Malachite Green isothiocyanate
4-methylumbelliferone
ortho cresolphthalein
nitrotyrosine
pararosaniline
Phenol Red
B-phycoerythrin
o-phthaldialdehyde Pyrene and Derivatives:
pyrene
pyrene butyrate
succinimidyl 1-pyrene butyrate
Reactive Red 4 (Cibacron® Brilliant Red 3B-A)

Rhodamine and Derivatives:
6-carboxy-X-rhodamine (ROX)
6-carboxyrhodamine (R6G)
lissamine rhodamine B sulfonyl chloride
rhodamine (Rhod)
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
terbium chelate derivatives One of ordinary skill in the art can easily determine, using art-known techniques of spectrophotometry, which fluorophores will make suitable donor-acceptor FRET pairs. For example, FAM (which has an emission maximum of 525 nm) is a suitable donor for TAMRA, ROX, and R6G (all of which have an excitation maximum of 514 nm) in a FRET pair. Probes are preferably modified during synthesis, such that a modified T-base is introduced into a designated position by the use of Amino-Modifier C6 dT (Glen Research), and a primary amino group is incorporated on the modified T-base, as described by Ju et al. (1995, Proc. Natl. Acad. Sci. USA 92:4347-4351). These modifications may be used for subsequent incorporation of fluorescent dyes into designated positions of the nucleic acid probes of the present disclosure.

The optimal distance between the donor and acceptor moieties will be that distance wherein the emissions of the donor moiety are maximally absorbed by the acceptor moiety. This optimal distance varies with the specific moieties used, and may be easily determined by one of ordinary skill in the art using well-known techniques. For energy transfer in which it is desired that the acceptor moiety be a fluorophore that emits energy to be detected, the donor and acceptor fluorophores are preferably separated when hybridized to target polynucleotide by a distance of up to 30 nucleotides, more preferably from 1-20 nucleotides, and still more preferably from 2 to 10 nucleotides and more preferably separated by 3, 4, 5, 6, 7, 8 and 9 nucleotides. For energy transfer wherein it is desired that the acceptor moiety quench the emissions of the donor, the donor and acceptor moieties are preferably separated by a distance of less than 10, 9, 8, 7, 6, 5, 4, 3, 2, or 1 nucleotide (e.g., on the opposite strand, complementary nucleotides of a duplex structure), although a 5 nucleotide distance (one helical turn) is also advantageous for use.

In yet another embodiment, the nucleic acid probes of the disclosure may be further labeled with any other art-known detectable marker, including radioactive labels such as $^{32}P$, $^{35}S$, $^{3}H$, and the like, or with enzymatic markers that produce detectable signals when a particular chemical reaction is conducted, such as alkaline phosphatase or horseradish peroxidase. Such enzymatic markers are preferably heat stable, so as to survive the denaturing steps of the amplification process. Nucleic acid probes may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. Nucleic acid probes may be supplementally labeled during chemical synthesis or the supplemental label may be attached after synthesis by methods known in the art.

The nucleic acid probes of the disclosure have use in nucleic acid detection, or amplification reactions as primers, or in the case of triamplification, blocking oligonucleotides, to detect or measure a nucleic acid product of the amplification, thereby detecting or measuring a target polynucleotide in a sample that is complementary to a 3' primer sequence. Accordingly, the nucleic acid probes of the disclosure can be used in methods of diagnosis, wherein a sequence is complementary to a sequence (e.g., genomic) of an infectious disease agent, e.g. of human disease including but not limited to viruses, bacteria, parasites, and fungi, thereby diagnosing the presence of the infectious agent in a sample of nucleic acid from a patient. The target polynucleotide can be genomic or cDNA or mRNA or synthetic, human or animal, or of a microorganism, etc.

In one embodiment the disclosure provides a useful screening tool for drug discovery where a rapid specific and sensitive assay can detect in vivo changes in the expression, suppression, mutation, or interaction of polynucleotides of interest, either at a steady state or in response to the administration of drug candidates. In another embodiment that can be used in the diagnosis or prognosis of a pathology, syndrome, disease or disorder. The target polynucleotide can be a naturally occurring, wild type, or genomic DNA, RNA or cDNA sequence, the mutation or alteration of which can indicate the presence or predisposition of a pathology, disease or disorder. Generally, a healthy organism expresses a target polynucleotide having a first sequence. An organism having a pathology or predisposition of a pathology typically expresses a variation of the target polynucleotide. The variation of the target polynucleotide includes deletions, mutations, substitutions, transpositions, insertions, inversions, single-nucleotide polymorphisms, and combinations thereof. In some instances, an organism having a pathology or predisposition of a pathology may not express a target polynucleotide, express reduced levels of the target polynucleotide, or express excessive levels of the target polynucleotide compared to levels of the target polynucleotide expressed by a healthy organism. Alternatively, the target polynucleotide can be a mutated or altered sequence. In one embodiment, an amplification reaction can be repeated for a same sample with different sets of probes that amplify, respectively, the naturally occurring sequence or the mutated version. By way of example, the mutation can be an insertion, substitution, and/or deletion of one or more nucleotides, or a translocation.

Pharmaceutical Compositions

Pharmaceutical compositions and dosage forms of the disclosure comprise a pharmaceutically acceptable salt of disclosed or a pharmaceutically acceptable polymorph, solvate, hydrate, dehydrate, co-crystal, anhydrous, or amorphous form thereof. Specific salts of disclosed compounds include, but are not limited to, sodium, lithium, potassium salts, and hydrates thereof.

Pharmaceutical compositions and unit dosage forms of the disclosure typically also comprise one or more pharmaceutically acceptable excipients or diluents. Advantages provided by specific compounds of the disclosure, such as, but not limited to, increased solubility and/or enhanced flow, purity, or stability (e.g., hygroscopicity) characteristics can make them better suited for pharmaceutical formulation and/or administration to patients than the prior art.

Pharmaceutical unit dosage forms of the compounds of this disclosure are suitable for oral, mucosal (e.g., nasal, sublingual, vaginal, buccal, or rectal), parenteral (e.g., intramuscular, subcutaneous, intravenous, intraarterial, or bolus injection), topical, or transdermal administration to a patient. Examples of dosage forms include, but are not limited to: tablets; caplets; capsules, such as hard gelatin capsules and soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions or water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The composition, shape, and type of dosage forms of the compositions of the disclosure will typically vary depending on their use. For example, a dosage form used in the detection of nucleic acids involved in a disease or disorder but expressed at a low level may contain larger amounts of the probe, for example the disclosed compounds or combinations thereof, than a dosage form used to detect nucleic acids that are overexpressed in a disease or disorder. Similarly, a parenteral dosage form may contain smaller amounts of the probe than an oral dosage form used to detect the same disease or disorder. These and other ways in which specific dosage forms encompassed by this disclosure will vary from one another will be readily apparent to those skilled in the art. See, e.g., Remington's Pharmaceutical Sciences, 18th ed., Mack Publishing, Easton, Pa. (1990).

Typical pharmaceutical compositions and dosage forms comprise one or more excipients. Suitable excipients are well known to those skilled in the art of pharmacy or pharmaceutics, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets or capsules may contain excipients not suited for use in parenteral dosage forms. The suitability of a particular excipient may also depend on the specific active ingredients in the dosage form. For example, the decomposition of some active ingredients can be accelerated by some excipients such as lactose, or when exposed to water. Active ingredients that comprise primary or secondary amines are particularly susceptible to such accelerated decomposition.

The disclosure further encompasses pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers. In addition, pharmaceutical compositions or dosage forms of the disclosure may contain one or more solubility modulators, such as sodium chloride, sodium sulfate, sodium or potassium phosphate or organic acids. A specific solubility modulator is tartaric acid.

Like the amounts and types of excipients, the amounts and specific type of active ingredient in a dosage form may differ depending on factors such as, but not limited to, the route by which it is to be administered to patients. However, typical dosage forms of the compounds of the disclosure comprise a pharmaceutically acceptable salt, or a pharmaceutically acceptable polymorph, solvate, hydrate, dehydrate, co-crystal, anhydrous, or amorphous form thereof, in an amount sufficient to detect the target polynucleotide and include a range of from about 10 mg to about 1000 mg, preferably in an amount of from about 25 mg to about 750 mg, and more preferably in an amount of from 50 mg to 500 mg.

Additionally, the compounds and/or compositions can be delivered using lipid- or polymer-based nanoparticles. For example, the nanoparticles can be designed to improve the pharmacological and therapeutic properties of drugs administered parenterally (Allen, T. M., Cullis, P. R. Drug delivery systems: entering the mainstream. Science. 303(5665):1818-22 (2004)).

Parenteral Dosage Forms

Parenteral dosage forms can be administered to patients by various routes, including, but not limited to, subcutaneous, intravenous (including bolus injection), intramuscular, and intraarterial. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, administration DUROS®-type dosage forms, and dose-dumping.

Suitable vehicles that can be used to provide parenteral dosage forms of the disclosure are well known to those skilled in the art. Examples include, without limitation: sterile water; Water for Injection USP; saline solution; glucose solution; aqueous vehicles such as but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate.

Compounds that alter or modify the solubility of a pharmaceutically acceptable salt of a disclosed composition herein can also be incorporated into the parenteral dosage forms of the disclosure, including conventional and controlled-release parenteral dosage forms.

Topical, Transdermal and Mucosal Dosage Forms

Topical dosage forms of the disclosure include, but are not limited to, creams, lotions, ointments, gels, shampoos, sprays, aerosols, solutions, emulsions, and other forms know to one of skill in the art. See, e.g., Remington's Pharmaceutical Sciences, 18th ed., Mack Publishing, Easton, Pa. (1990); and Introduction to Pharmaceutical Dosage Forms, 4th ed., Lea & Febiger, Philadelphia, Pa. (1985). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as freon), or in a squeeze bottle. Moisturizers or humectants can also be added to pharmaceutical compositions and dosage forms if desired. Examples of such additional ingredients are well known in the art. See, e.g., Remington's Pharmaceutical Sciences, 18th Ed., Mack Publishing, Easton, Pa. (1990).

Transdermal and mucosal dosage forms of the compositions of the disclosure include, but are not limited to, ophthalmic solutions, patches, sprays, aerosols, creams, lotions, suppositories, ointments, gels, solutions, emulsions, suspensions, or other forms known to one of skill in the art. See, e.g., Remington's Pharmaceutical Sciences, 18th Ed., Mack Publishing, Easton, Pa. (1990); and Introduction to Pharmaceutical Dosage Forms, 4th Ed., Lea & Febiger, Philadelphia, Pa. (1985). Dosage forms suitable for treating mucosal tissues within the oral cavity can be formulated as mouthwashes, as oral gels, or as buccal patches. Additional transdermal dosage forms include "reservoir type" or "matrix type" patches, which can be applied to the skin and worn for a specific period of time to permit the penetration of a desired amount of active ingredient.

Examples of transdermal dosage forms and methods of administration that can be used to administer the active ingredient(s) of the disclosure include, but are not limited to, those disclosed in U.S. Pat. Nos. 4,624,665; 4,655,767; 4,687,481; 4,797,284; 4,810,499; 4,834,978; 4,877,618; 4,880,633; 4,917,895; 4,927,687; 4,956,171; 5,035,894; 5,091,186; 5,163,899; 5,232,702; 5,234,690; 5,273,755; 5,273,756; 5,308,625; 5,356,632; 5,358,715; 5,372,579; 5,421,816; 5,466;465; 5,494,680; 5,505,958; 5,554,381; 5,560,922; 5,585,111; 5,656,285; 5,667,798; 5,698,217; 5,741,511; 5,747,783; 5,770,219; 5,814,599; 5,817,332; 5,833,647; 5,879,322; and 5,906,830, each of which are incorporated herein by reference in their entirety.

Suitable excipients (e.g., carriers and diluents) and other materials that can be used to provide transdermal and mucosal dosage forms encompassed by this disclosure are well known to those skilled in the pharmaceutical arts, and depend on the particular tissue or organ to which a given pharmaceutical composition or dosage form will be applied. With that fact in mind, typical excipients include, but are not limited to water, acetone, ethanol, ethylene glycol, propylene glycol, butane-1,3-diol, isopropyl myristate, isopropyl palmitate, mineral oil, and mixtures thereof, to form dosage forms that are non-toxic and pharmaceutically acceptable.

Depending on the specific tissue to be treated, additional components may be used prior to, in conjunction with, or subsequent to treatment with pharmaceutically acceptable salts of the disclosed compositions. For example, penetration enhancers can be used to assist in delivering the active ingredients to or across the tissue. Suitable penetration enhancers include, but are not limited to: acetone; various alcohols such as ethanol, oleyl, an tetrahydrofuryl; alkyl sulfoxides such as dimethyl sulfoxide; dimethyl acetamide; dimethyl formamide; polyethylene glycol; pyrrolidones such as polyvinylpyrrolidone; Kollidon grades (Povidone, Polyvidone); urea; and various water-soluble or insoluble sugar esters such as TWEEN 80 (polysorbate 80) and SPAN 60 (sorbitan monostearate).

The pH of a pharmaceutical composition or dosage form, or of the tissue to which the pharmaceutical composition or dosage form is applied, may also be adjusted to improve delivery of the active ingredient(s). Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of the active ingredient(s) so as to improve delivery. In this regard, stearates can serve as a lipid vehicle for the formulation, as an emulsifying agent or surfactant, and as a delivery-enhancing or penetration-enhancing agent. Different hydrates, dehydrates, co-crystals, solvates, polymorphs, anhydrous, or amorphous forms of the pharmaceutically acceptable salt of a disclosed composition can be used to further adjust the properties of the resulting composition.

EXAMPLES
Example 1

Dual Nucleic Acid Probes

Oligonucleotide Synthesis. Oligonucleotide probes and targets were synthesized using standard phosphoramidite utes. The oligonucleotides were additionally purified by IE-HPLC using a Source™ column (Amersham Pharmacia Biotech, Piscataway, N.J.) and eluted with a linear 0% to 50% 1 M LiCl gradient in 0.1 M Tris pH 8.0 over 40 minutes. Unmodified (target) oligonucleotides were purified using polyacrylamide gel electrophoresis. All oligonucleotides were synthesized at Integrated DNA Technologies, Inc. (Coralville, Iowa).

Figure 2:
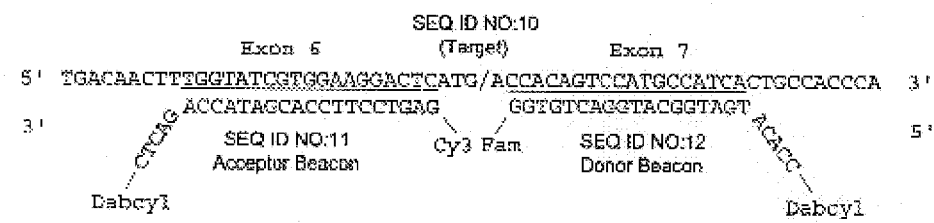
FIG. 2 shows a schematic of the assay system with 4-base spacing between donor and acceptor molecular beacons when hybridized to the synthetic target. In this example both beacons have a probe length of 19 bases and a stem length of 5 bases. The underscores indicate the 38-base sequence of the target complementary to the beacons. Note that for each beacon one arm of the stem is part of the probe sequence so that the movement of the dye molecules is restricted after hybridization.

Probe and Target Design. All oligonucleotide probes were designed to be complementary in antisense orientation to the human GAPDH gene, as illustrated in FIG. 2. Specifically, a dabcyl quencher was attached to the 5'-end and a 6-Fam fluorophore was attached to the 3'-end of donor molecular beacons; a dabcyl quencher was attached to the 3'-end and either a Cyanine 3 (Cy3), 6-carboxyrhodamine (ROX), or Texas Red fluorophore was attached to the 5'-end of acceptor molecular beacons. The stem sequence was designed to participate in both hairpin formation and target hybridization (Tsourkas et al., 2002b). This beacon design was chosen to help fix the relative distance between the donor and acceptor fluorophores and improve energy transfer efficiency. Both the donor and acceptor beacons were designed with a probe length of 18 bases and a stem length of 5 bases. The probe length is defined as the portion of the molecular beacon that is complementary to the target. The synthetic wild-type GAPDH target has 4-base gap between the donor dye and the acceptor dye. Gap spacing was adjusted to 3, 5, and 6 bases by either removing a guanine residue or adding 1 or 2 thymine residues, as shown in Table 1.

TABLE 1

Design of Probes and Target Oligonucleotides

| Name | Sequence (5'-3') | | Note |
|---|---|---|---|
| Fam donor-MB[1] | Dabcyl-ccacaTGATGGCATGGACTGTGG-Fam | SEQ ID NO:1 | Probe 18/Stem 5 |
| Tb donor probe | TGATGGCATGGACTGTGG-DTPA-cs124-(Tb) | SEQ ID NO:2 | Probe 18/Stem 0 |
| Cy3 acceptor-MB | Cy3-GAGTCCTTCCACGATACCgactc-Dabcyl | SEQ ID NO:3 | Probe 18/Stem 5 |
| ROX acceptor-MB | ROX-GAGTCCTTCCACGATACCgactc-Dabcyl | SEQ ID NO:4 | Probe 18/Stem 5 |
| Texas Red acceptor-MB | Texas Red-GAGTCCTTCCACGATACCgactc-Dabcyl | SEQ ID NO:5 | Probe 18/Stem 5 |
| Target[2] n − 1 | ACTTTGGTATCGTGGAAGGACTCATACCACAGTCCATGCCATCA CTGCC | SEQ ID NO:6 | 3 base gap |
| Target n (WT) | ACTTTGGTATCGTGGAAGGACTCATGACCACAGTCCATGCCATCA CTGCC | SEQ ID NO:7 | 4 base gap |
| Target n + 1 | ACTTTGGTATCGTGGAAGGACTCATTGACCACAGTCCATGCCATCA CTGCC | SEQ ID NO:8 | 5 base gap |
| Target n + 2 | ACTTTGGTATCGTGGAAGGACTCATTTGACCACAGTCCATGCCATCA CTGCC | SEQ ID NO:9 | 6 base gap |

[1]MB = Molecular Beacon. Lower case = bases added to create stem domains. Upper case = probe-target hybridizing domains. Upper case bold = bases participating in both stem formation and target binding
[2]Underscore = 18 base sequence complementary to MB target binding domains. n = 4 bases the wild-type gap size chemistry on an Applied Biosystems model 394 automated DNA synthesizer (Foster City, Calif.). Molecular beacons were purified using dual reverse phase (RP) plus ion-exchange (IE) high performance liquid chromatography (HPLC) on a Waters Model 600E HPLC system (Millipore Corp., Milford, Mass.). For RP-HPLC purification, oligonucleotides were loaded on a Hamilton PRP-1 column and eluted with a linear 5% to 50% acetonitrile gradient in 0.1 M triethyl-ammonium acetate (TEM) pH 7.2 over 40 min- Lanthanide Chelate Synthesis. A linear oligonucleotide with a probe length of 18 bases was labeled at its 3'-end with a diethylenetriaminepentaacetic acid (DTPA) chelate covalently joined to a sensitizer, cs124 (Cooper and Sammes, 2000). As demonstrated in Table 1, the sequence of this linear probe was identical to the probe domain of the donor molecular beacons specific for exon 7 of the human GAPDH gene.

The lanthanide chelate was prepared by first dissolving DTPA (500 mg, 1.4 μmole) in 30 mL of DMF and 1 mL of triethylamine. Cs124 (240 mg, 1.4 μmole), dissolved in 4 mL of DMF, was then added dropwise and mixed for 30 minutes. To this mixture, 5 mL (75 μmole) of ethylenediamine (EDA) was added and stirred at room temperature for two hours. The mixture was then stored in the refrigerator overnight. A slightly off-white precipitate had formed and was centrifuged down further. The DMF supernatant was removed and the pellet was washed with isopropanol several times and then with ether resulting in a fine white powder, which was dried under a vacuum for 2 hours. The powder was resuspended in water and RP-HPLC purified using a Hamilton PRP-1 column. The sample was eluted with a linear 0% to 30% acetonitrile gradient in 0.1 M TEAA pH 7.2 over 20 minutes at a flow rate of 10 mL/min. The first peak was collected, and the DTPA-cs124 product was dried and reconstituted to a concentration of 15 mM in 0.1 M Borate Buffer, pH 8.5.

Disuccinimidyl suberate (1.84 mg, 5 μmoles; Pierce Chemical) was dissolved in 100 μL of DMSO and added to 0.1 μmoles of oligonucleotides with a 3'-amine, dissolved in 100 uL of DMSO. The mixture was incubated at 40° C. for 2 hours. The oligonucleotides were then acetone precipitated and reconstituted in 100 μl of 0.1 M sodium borate pH 8.5. 50 uL of 1.5 mM DTPA-cs124-EDA product in borate buffer was added to the oligonucleotide solution and mixed overnight. Oligonucleotide-DTPA-cs124-EDA conjugates were purified using reversed-phase (RP)HPLC. The oligonucleotides were loaded on a PRP-1 column and eluted with a linear 5% to 50% acetonitrile gradient in 0.1 M TEM pH 7.2 over 40 minutes. The collected peak was lyophilized and reconstituted in dH$_2$O at 5 μM. TbCl$_3$ (Terbium) dissolved in PBS was then added to the sample at a 10:1 molar ratio and incubated at room temperature for 30 minutes. The Europium chelates were synthesized following the same protocol.

Hybridization and Detection Assays. Hybridization experiments were conducted with 50 pmoles of donor beacon, 50 pmoles of acceptor beacon and 50 pmoles of complementary target in a total volume of 100 μL (0.5 μM). All experiments were conducted at 37° C. in HB buffer containing 10 mM KCl, 5 mM MgCl$_2$, and 10 mM Tris-HCl, pH 7.5, which was supplemented with 1% Bovine Albumin Serum to block non-specific interactions with the microplate. The samples were mixed and allowed to equilibrate at 37° C. for 20 minutes before performing fluorometry. A Safire microplate fluorometer (Tecan, Zurich, Switzerland) was used to excite the donor beacons and detect resulting emission (500 nm to 650 nm) in FRET measurements. The excitation wavelength was varied from 395 nm to 495 nm to determine the wavelength that resulted in the maximal FRET between the donor and acceptor molecules. In a two-photon experimental set-up, the excitation spectra of Fam- and Cy3-labeled linear oligonucleotides were obtained. A tunable laser was adjusted to excite the samples at wavelengths ranging from 700 nm to 875 nm. The fluorescence emission between 505 nm and 555 nm was detected from the Fam sample and the emission between 590 and 650 nm was detected from the Cy3 sample using ultra-sensitive, low noise avalanche photodiodes.

For LRET measurements, the Terbium and Europium donor probes were excited at a wavelength of 325 nm, and the emission was recorded from 500 nm to 650 nm for assays with Terbium donors, and from 550 nm to 750 nm for assays involving Europium donors. The emission detection had a lag time of 50 μs with an integration time of 1 ms. The maximal excitation and emission wavelengths of the organic and lanthanide dyes used in this study are summarized in Table 2.

TABLE 2

Maximal Excitation and Emission Wavelengths of Organic and Lanthanide Dyes

| Dye Molecule | Excitation (nm) | Emission (nm) | Extinction Coefficient ($M^{-1} \cdot cm^{-1}$) | Note |
|---|---|---|---|---|
| 6-Fam | 494 | 518 | 83,000 | Donor |
| Terbium Chelate | 300-340 | 546 | 10,000-35,000 | Donor |
| Europium Chelate | 300-340 | 620 | 10,000-35,000 | Donor |
| Cy3 | 552 | 570 | 150,000 | Acceptor |
| Rox | 585 | 605 | 82,000 | Acceptor |
| Taxes Red | 583 | 603 | 116,000 | Acceptor |

FRET of Organic Dye Pairs. A series of solution-phase assays were conducted to determine whether the signal generated by a pair of molecular beacons hybridized to the same target oligonucleotide can be differentiated from the signal due to false-positive events. For organic dye pairs, the same donor beacon (i.e., a molecular beacon with a fluorescent donor dye) was tested with three acceptor (reporter) beacons for the magnitudes of background signal and positive (FRET) signal. Here, "background" is defined as fluorescence detected from one or both beacons in the absence of target or from either beacon alone in the presence of target. Thus background represents any fluorescence emission detected in the absence of a FRET event due to the simultaneous hybridization of the donor and acceptor beacons to the same target. If fluorescence excitation is limited to wavelengths $\lambda_e$ optimal for the donor fluorophore and signal detection is limited to wavelengths $\lambda_d$ optimal for the acceptor (reporter) fluorophore, fluorescent signal should be low unless both beacons hybridize to the same target and FRET occurs. However, since fluorescence from organic fluorophores occurs over a broad range of wavelengths, it is possible for fluorescence emission from the donor at $\lambda_d$ and from the acceptor due to direct excitation at $\lambda_e$ to contribute to background. "Positive signal" is defined as FRET-induced fluorescence detected when both beacons are bound to the same target, again restricting excitation to wavelengths $\lambda_e$ and limiting detection to wavelengths $\lambda_d$.

As illustrated in Table 1, the donor molecular beacon was labeled with 6-Fam on the 3'-end, and the acceptor molecular beacons were labeled with Cy3, ROX, or Texas Red on the 5'-end. Sequences of donor and acceptor molecular beacons were chosen to be complementary to adjacent sites within exon 6 and exon 7 of the human GAPDH gene and were positioned with a four base separation between donor and acceptor fluorophores when wild-type target was used. Four types of assays were performed with each donor/acceptor beacon pair: (1) both donor and acceptor beacons in the absence of target, with a typical emission spectrum (i.e., fluorescence intensity as a function of wavelength) shown as curve a in FIG. 3 (spectrum a); (2) donor beacon only in the presence of target, with a typical emission spectrum shown as curve b in FIG. 3 (spectrum b); (3) acceptor beacon only in the presence of target, with a typical emission spectrum shown as curve c in FIG. 3 (spectrum c); and (4) both donor and acceptor beacons in the presence of target, with a typical emission spectrum shown as curve d in FIG. 3 (spectrum d). Assays (2) and (3) simulate the limiting false positive scenario where most of the molecular beacons open as a result of nuclease degradation, denaturation, or non-specific protein interactions (which hereafter will collectively be referred to as 'degraded' beacons).

Figure 3:
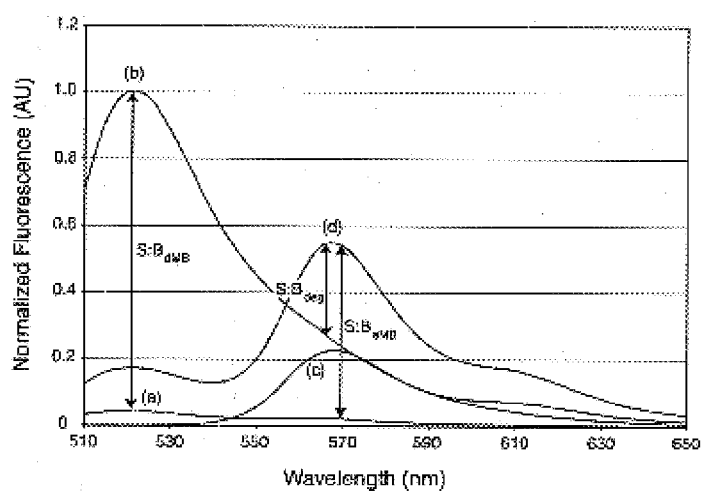
FIG. 3 shows typical emission spectra of dual FRET molecular beacons. Three signal-to-background ratios are defined: $S:B_{dMB}$ represents the enhancement in fluorescence of a conventional molecular beacon in the presence of target. $S:B_{aMB}$ indicates the increase in fluorescence resulting from the sensitized emission of the acceptor. $S:N_{deg}$ is the ratio of the signal from sensitized emission of the acceptor to the false-positive signal.
Figure 4A:
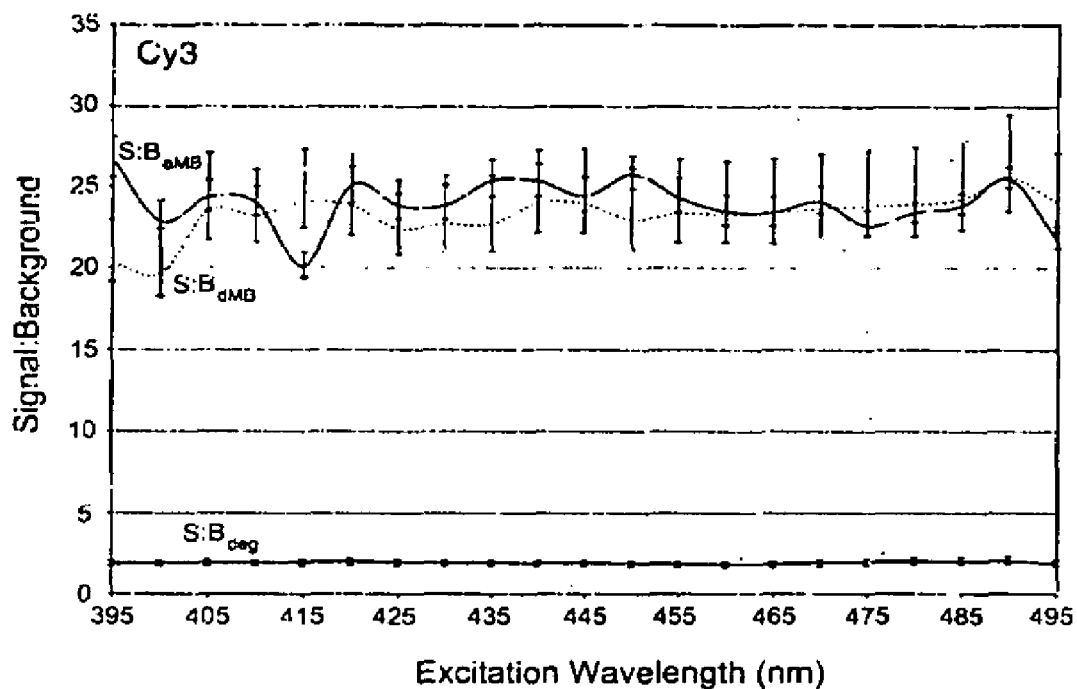
FIGS. 4a-4c show signal-to-noise ratios for dual FRET molecular beacons with (4a) a Fam-Cy3 FRET pair, (4b) a Fam-ROX FRET pair and (4c) a Fam-Texas Red FRET pair. The error bars display the minimum and maximum ratios calculated for dual FRET molecular beacons separated by 3, 4, 5, or 6 bases.

To illustrate the advantages of using duel FRET molecular beacons and to compare the performance of different acceptor molecular beacons, several signal-to-background ratios were calculated. As illustrated in FIG. 3, the first is $S:B_{dMB}$, the ratio of the peak fluorescence intensity of emission spectrum b defined above for donor molecular beacons (dMB) to that of emission spectrum a at the same wavelength. Although spectrum a was generated with both the donor and acceptor beacons in solution, the fluorescence signal is largely due to the donor beacons, for the emission of the acceptor beacons at the corresponding wavelength is almost zero, as can be seen from curve c in FIG. 3. Thus, $S:B_{dMB}$ represents the signal-to-background ratio of the conventional single molecular beacon assay. The second is $S:B_{aMB}$, the ratio of the peak fluorescence intensity of emission spectrum d of the acceptor molecular beacon (aMB) due to FRET to that of emission spectrum a at the same wavelength. Clearly, $S:B_{aMB}$ represents the signal-to-background ratio of the dual FRET molecular beacons assay without degraded beacons. The third one, $S:B_{deg}$, is defined as the ratio of the peak fluorescence intensity of emission spectrum d due to FRET to that of emission spectrum b or c at the same wavelength, whichever is higher. $S:B_{deg}$ represents the signal-to-background ratio of the dual FRET molecular beacons assay for the limiting case that most of the donor and acceptor beacons are being degraded. Here, with up to $1\times10^5$ molecular beacons per cell, the probability of having both degraded donor and acceptor beacons at the same spatial location (i.e., within a cylinder of 0.2 μm in diameter and 1 μm in thickness) in a fluorescence imaging assay is small. This is especially true considering that, with chemical modifications of the beacon backbone, only a small fraction (<50%) of the molecular beacons would be degraded in an intracellular environment. It is worth mentioning that all the signal-to-background ratios discussed above change with the donor excitation wavelength. As shown in FIG. 4a, $S:B_{aMB}$ of the FRET assay with Cy3-labeled acceptor beacons was almost identical to $S:B_{dMB}$ of the donor beacon alone over the entire range of excitation wavelengths tested. Neither parameter varied significantly, ranging between 20 and 25, as the excitation wavelength λ was increased. The dual FRET molecular beacons, however, did generate a signal 2 to 3 times stronger compared with that of degraded beacons, i.e., $S:B_{deg}$ has a value of 2-3, while conventional molecular beacons cannot differentiate between signals due to degraded and hybridized probes. Signal enhancement upon molecular beacon/target binding is strongly affected by cation concentration and temperature. In this case, the $S:B_{deg}$ was relatively low since the assay temperature of 37° C. was near the stem melting temperature.

Figure 4B:
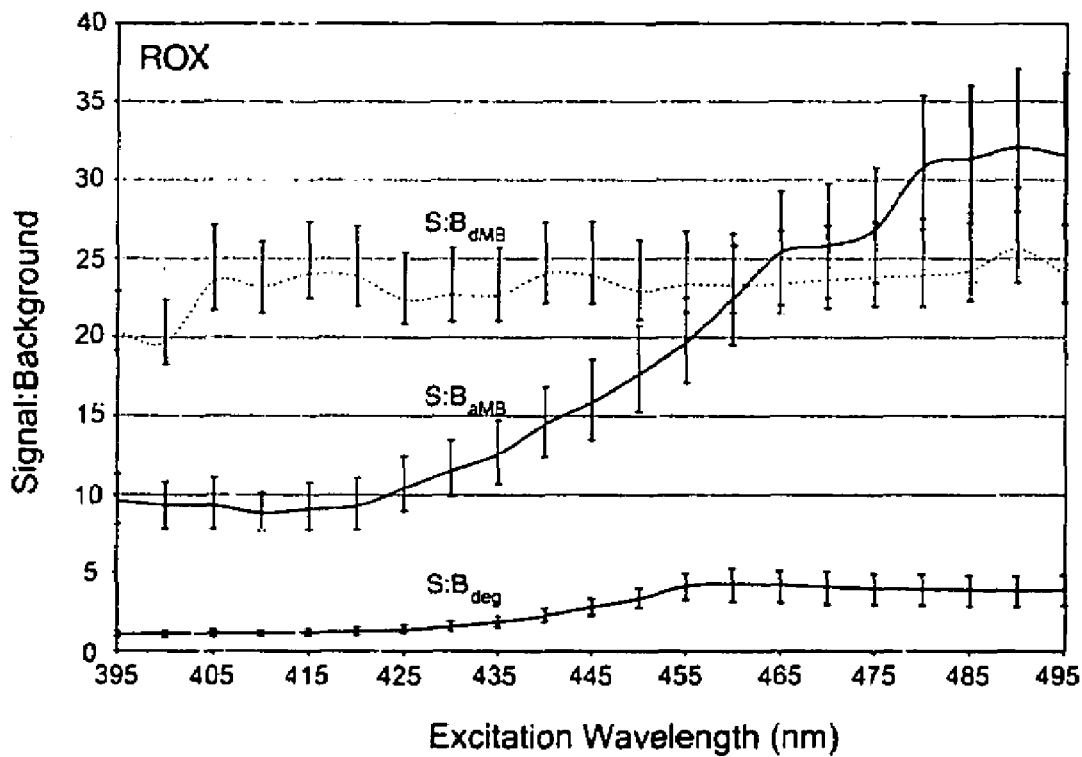
Figure 4C:
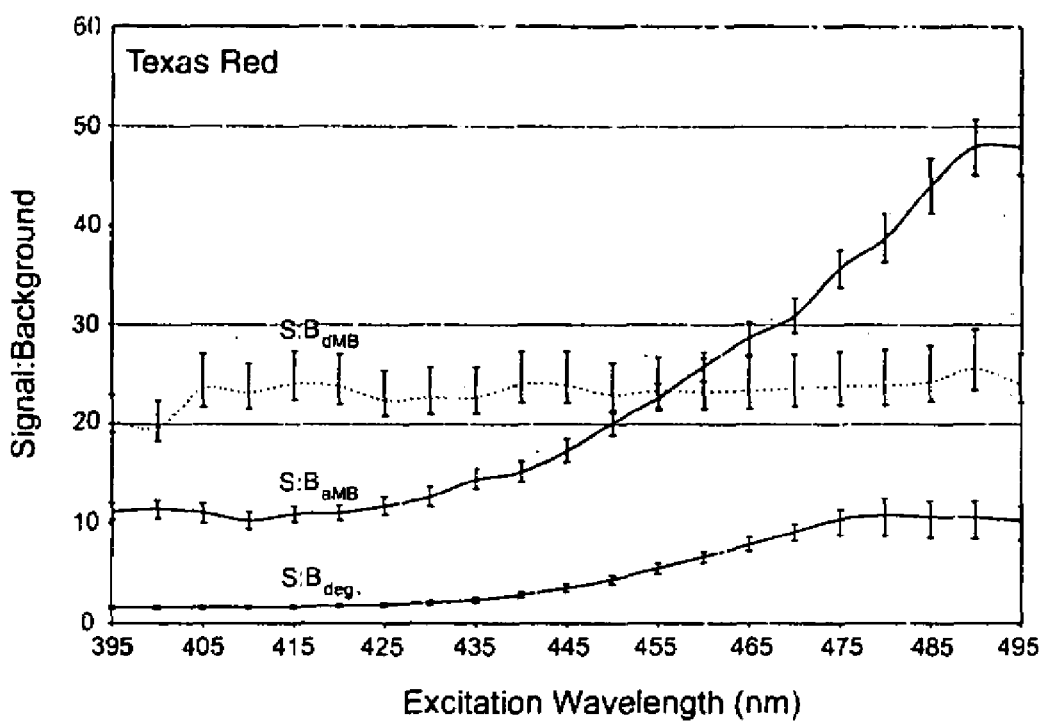
Figure 5:
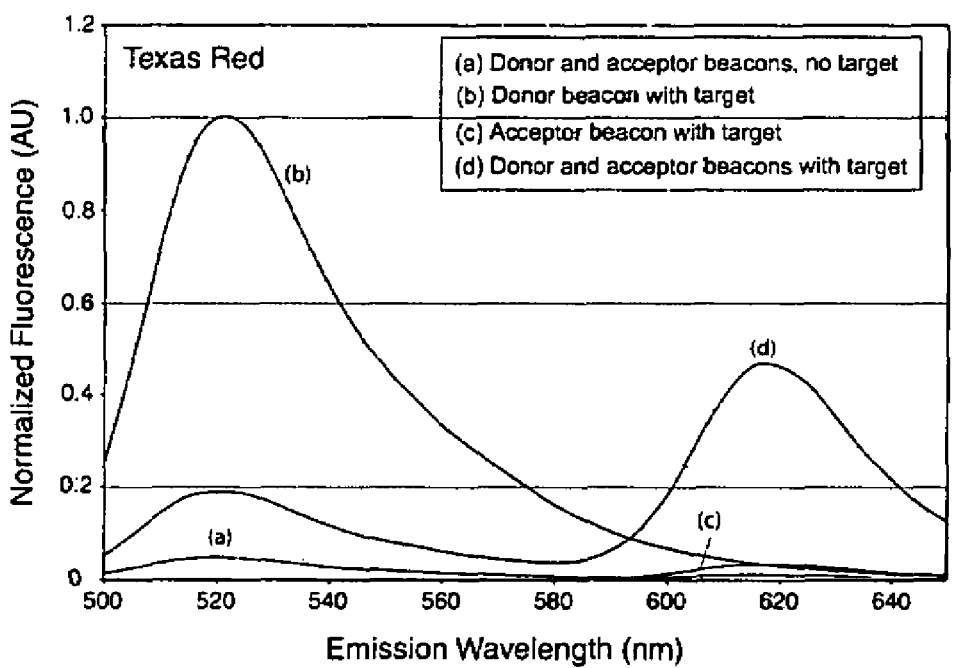
FIG. 5 shows emission spectra for dual FRET molecular beacons with a Fam-Texas Red FRET pair. The samples described in the figure were excited at a wavelength of 475 nm.

When a ROX fluorophore was used as the acceptor dye, $S:B_{aMB}$ was found to be ~10, about half of $S:B_{dMB}$, at low excitation wavelengths λ (e.g., 395 nm to 425 nm), as shown in FIG. 4b. However, when λ was increased, $S:B_{aMB}$ also increased. In fact, when λ became larger than 460 nm, $S:B_{aMB}$ was higher than $S:B_{dMB}$, reaching values above 30. This indicates that the dual FRET molecular beacons with a Fam-ROX FRET pair can perform better than the conventional molecular beacons even in the absence of beacon degradation issues. The value of $S:B_{deg}$ also increased with increasing λ, reaching values close to 5 at λ=455 nm, remaining between 4 and 5 for wavelengths ranging from 455 nm to 495 nm. Acceptor beacons labeled with Texas Red were found to perform the best among the three acceptor dyes considered. Value of $S:B_{aMB}$ increased from 10 to nearly 50 as λ was increased from 395 nm to 495 nm. Moreover, as λ was increased from 455 nm to 475 nm the value of $S:B_{deg}$ increased from ~2 to over 10 and remained around 10 for λ>475 nm, as demonstrated in FIG. 4c. Therefore, the signal generated by binding of both donor and acceptor beacons to a target could be 10 times brighter than false-positive signals. An example of the spectra generated using the Fam-Texas Red FRET pair is given in FIG. 5.

Figure 6:
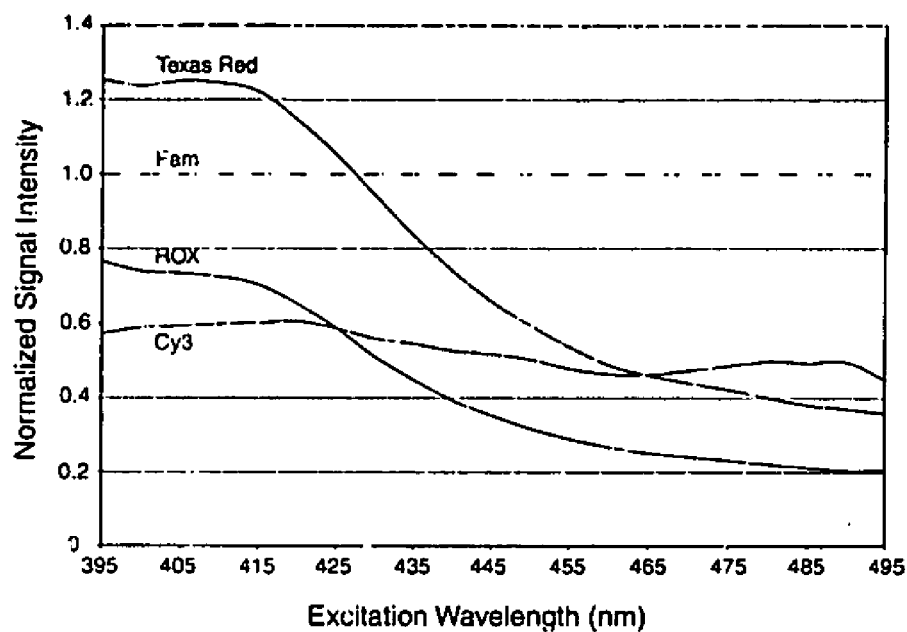
FIG. 6 shows normalized peak emission of the acceptor due to FRET for molecular beacon pairs with a Fam donor and a Cy3, ROX, or Texas Red acceptor. All the intensities were normalized relative to the peak intensity of the Fam-labeled donor beacon bound to target.

Although the performance of dual FRET molecular beacons is better than non-FRET molecular beacons due to increased signal-to-background ratio and the ability to differentiate between bound and degraded molecular beacons, the peak fluorescence intensity of the acceptor beacons was typically lower than that of the Fam-labeled donor beacons, as shown in FIG. 6. Specifically, at wavelengths where optimal FRET signal-to-background ratios were obtained, for Fam-Texas Red FRET pair the peak signal intensity of the acceptor was only about 40% of that emitted by the Fam-donor alone, and only about 25% for the Fam-ROX FRET pair, which may limit ultimate sensitivity.

Figure 7:
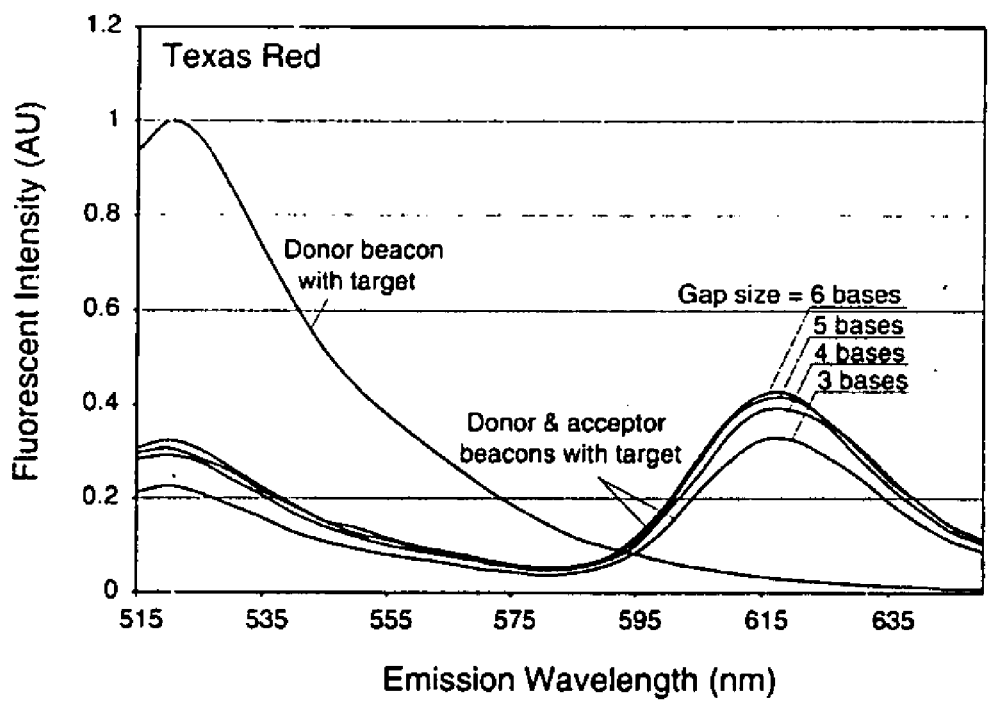
FIG. 7 shows the effect of spacing between donor and acceptor beacons on the fluorescence emission of acceptor dye for dual FRET molecular beacons with a Fam donor and a Texas Red acceptor. Four different targets were tested, separating the donor and acceptor beacons by 3, 4, 5, or 6 bases.

The efficiency E of fluorescence energy transfer between the donor and acceptor fluorophores varies according to $$E=1/(1+R^6/R_0^6) \qquad (1)$$

where R is the distance between donor and acceptor dyes, and $R_0$ is the Förster energy transfer distance or the distance at which E=0.5. For typical fluorophores $R_0$=1~5 nm. Equation (1) implies that the gap (i.e., the number of bases) between the donor and acceptor beacons should be kept small. However, too small a gap size may result in steric interference between fluorophores or might lead to other interaction between donor and acceptor (such as ground state quenching), which is unfavorable. The gap size can influence the relative orientation of the fluorophores, also affecting energy transfer efficiency. A gap size of 8 bases was found to be optimal for energy transfer in the single-stranded random-coil conformation (Ju et al., 1995; Hung et al., 1997). Further, base composition can influence fluorescence efficiency. The combination of a fluorescein dye attached to a guanine base can decrease peak fluorescence intensity by as much as 30% (M. Behike, unpublished observation). To optimize design parameters, hybridization experiments were conducted using targets that separate the donor and acceptor beacons by 3, 4, 5, and 6 bases. The nucleotides closest to the probe-binding region were identical for each target sequences. When the distance between the donor and acceptor beacons was increased from 3 to 6 bases, there was a slight increase in the FRET signal intensity, as demonstrated by the curves displayed in FIG. 7. This trend was found to be the same for all the acceptor fluorophores studied.

LRET of Lanthanide Dyes. Conventional organic dyes used for FRET assays are limited by problems associated with the overlapping of donor/acceptor excitation and emission spectra. To dramatically improve the signal-to-background ratio, the inventor takes advantage of the sharp emission peaks and the long lifetime of a lanthanide chelate (Li and Selvin, 1997; Cooper and Sammes, 2000). Specifically, a lanthanide donor is substituted for the Fam donor and modified the detection system to employ time-resolved spectroscopy. The lanthanide donor was a linear oligonucleotide probe labeled at its 3'-end with the Terbium chelate DTPA-cs124 (Table 1). The same series of acceptor molecular beacons were tested as before, including beacons with Cy3, ROX, or Texas Red fluorophores. Note that the use of lanthanide donor allows for shorter wavelength excitation, as demonstrated in Table 2.

Figure 8A:
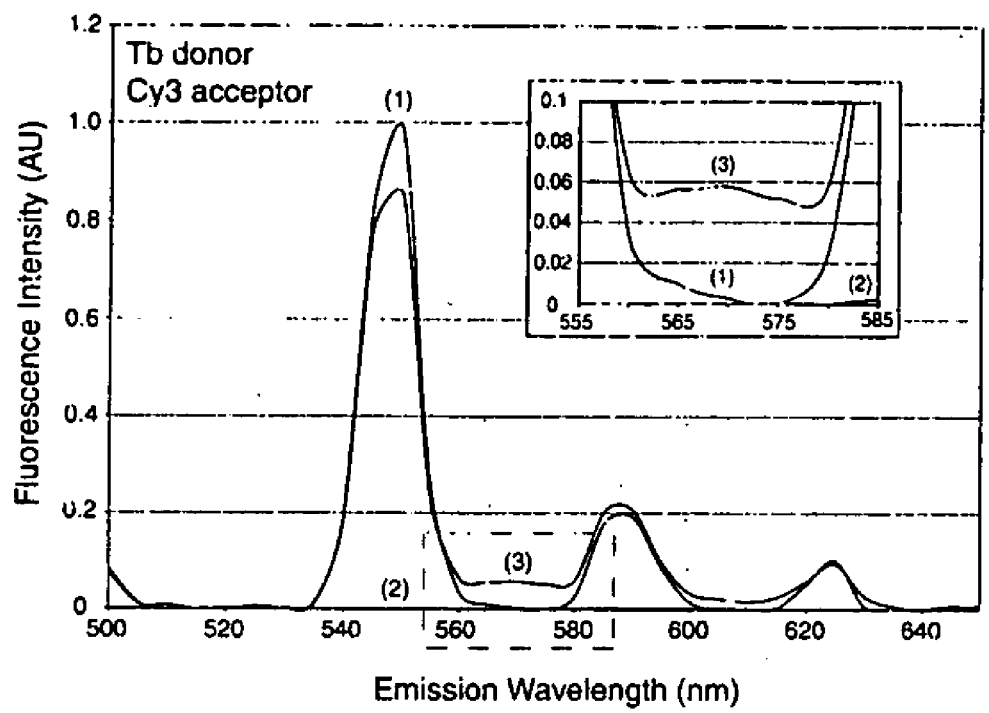
FIGS. 8a and 8b show time resolved emission spectra obtained in a two-probe detection assay using Terbium chelate as a donor and (8a) Cy3 as an acceptor and (8b) ROX as an acceptor. All samples were excited at a wavelength of 325 nm.
Figure 8B:
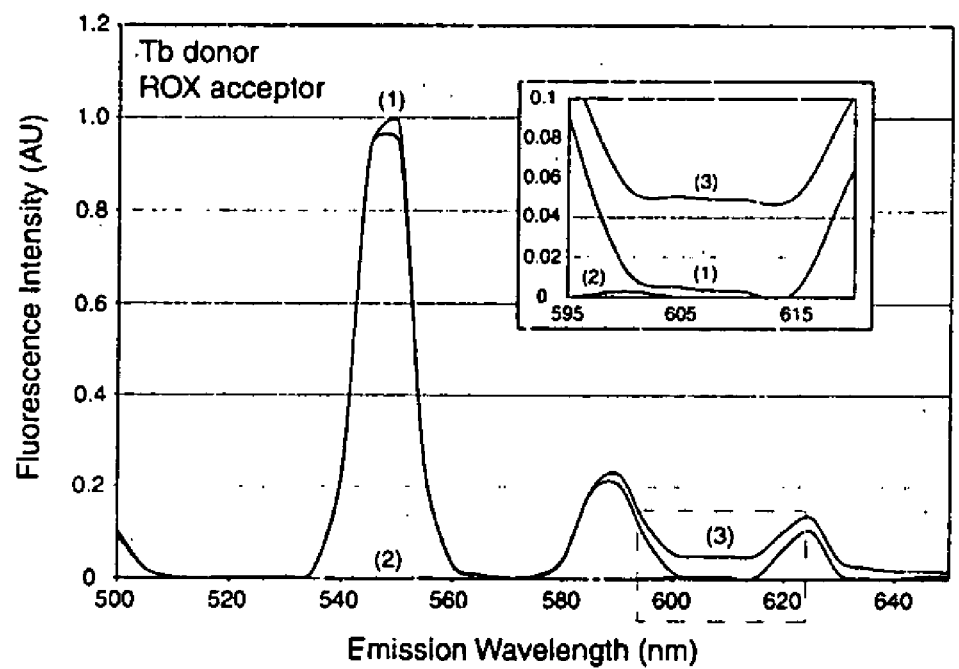

The results of LRET experiments with a lanthanide donor are shown in FIGS. 8a, b. As shown by curve (1) in FIG. 8a, at 325 nm excitation, when the Terbium-chelate labeled donor probes bound to Cy3 labeled acceptor beacons, they exhibited several sharp emission peaks separated by valleys with fluorescence intensity close to zero; while the fluorescence emission from acceptor molecular beacons alone hybridized to targets was extremely low, as shown by curve (2). With binding of both donor probes with Terbium-chelate and acceptor molecular beacons to target, a sensitized emission of the acceptor due to LRET was observed, shown as curve (3). As clearly demonstrated by the insert in FIG. 8a, at emission wavelengths where background from the lanthanide donor was near zero, extremely high signal-to-background ratios were observed. For Cy3-labeled acceptor beacon, the optimal detection wavelength is around 573 nm. Similar features were exhibited in FIG. 8b in which the time resolved emission spectra obtained with 325 nm excitation in a dual LRET probe assay using Terbium chelate as a donor and ROX as an acceptor were displayed. It is again very clear that at certain emission wavelengths the signal-to-background ratio approaches infinity. As seen from the insert of FIG. 8b, for ROX-labeled acceptor beacon, the optimal detection wavelength is around 614 nm. Although the fluorescence emission due to energy transfer was very low, these results nevertheless suggest that there is a significant potential for use of lanthanide donors with dual energy transfer molecular beacons.

To determine the possible detrimental effect of small gap size between donor and acceptor probes on LRET, the spacing between the Terbium-labeled donor probe and the Cy3 or ROX-labeled acceptor beacon was varied from 3 to 9 bases. It was found that the detected fluorescence intensity is not sensitive to the gap spacings tested, i.e., with a spacing of 3, 4, 5, 6 and 9 bases, the signal levels were similar (data not shown), suggesting that the possible detrimental effect was negligible when both probes hybridized to the target with a relatively small gap spacing. Using Equation (1), it is readily shown that, with the gap spacing varying from 3 to 9 bases, the energy transfer efficiency does not change much, since the Förster distance $R_0$ for the Terbium/Cy3 LRET pair is large 6 (0.12 nm) (Selvin, 2002). For example, when R in Equation (1) increases from 1 nm (~3 bases) to 2 nm (~6 bases) and to 3 nm (~9 bases), the energy transfer efficiency E only decreases by 0.12% and 1.37%, respectively.

Figure 9:
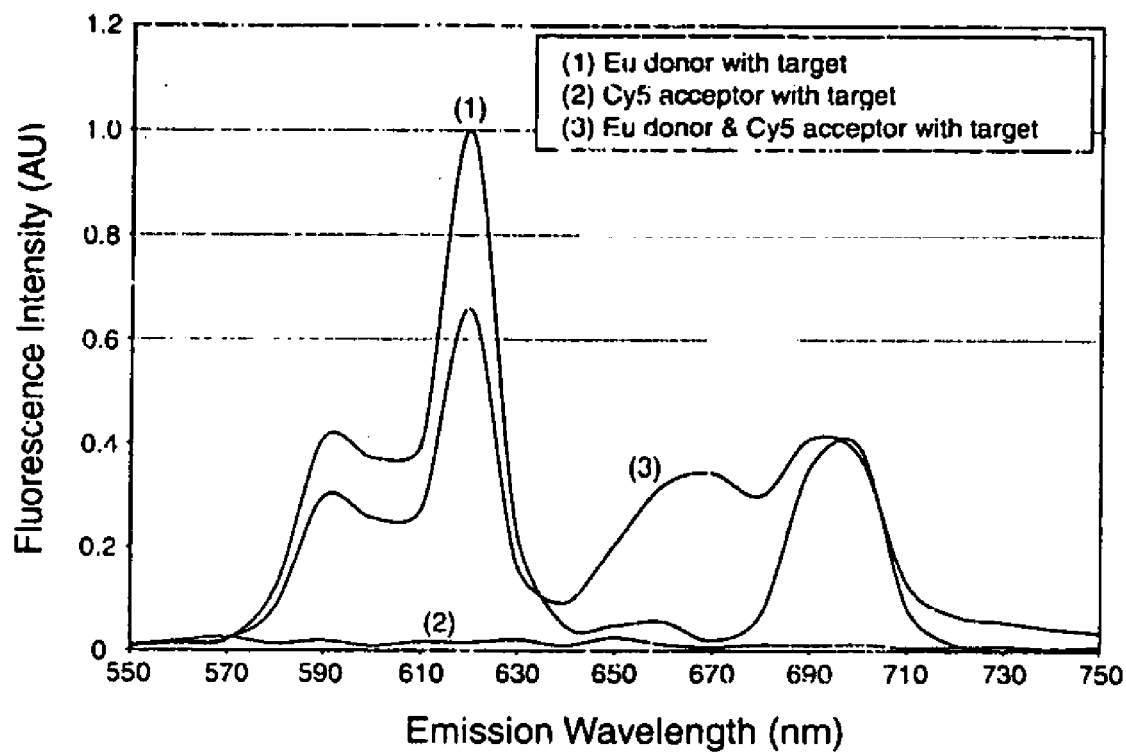
FIG. 9 shows time resolved emission spectra generated by a two-probe detection assay utilizing a Europium-labeled oligonucleotide as a donor probe and a Cy5-labeled oligonucleotide as an acceptor probe.

Due to the narrow emission peaks exhibited by lanthanide dyes, and the use of time-resolved fluorescence detection, it is not necessary to include a quencher molecule in the acceptor molecular beacons, although the stem-loop hairpin structure of the beacon may still be beneficial. However, when the detection of point mutations is not involved, the use of linear LRET pairs of oligonucleotide probes is attractive owing to its potential in reducing cost while having comparable performance. To demonstrate the concept, donor oligonucleotide probes labeled with a Europium chelate at its 3'-end, and acceptor oligonucleotide probes labeled at its 5'-end with a Cy5 fluorophore were synthesized, and in-solution hybridization and time-resolved emission detection assays were performed. The resulting emission spectra are displayed in FIG. 9. Similar to the results obtained using Terbium-chelate donors, at 325 nm excitation, the emission spectrum of Europium donor bound to target showed several peaks within the range of 550 nm to 750 nm, as demonstrated by curve (1). The fluorescence emission of the Cy5-labled acceptor probe due to probe/target hybridization is again almost zero (curve (2)). When both donor and acceptor probes hybridized to the same target, there was a sensitized emission of the acceptor due to LRET, as shown by curve (3). Evidently, at certain wavelengths (such as 670 nm), the background signal due to degraded donor and acceptor probes becomes very low, leading to a high signal-to-background ratio. It was found that with the DTPA-cs124 chelate used in this study, the LRET probe pairs with a Terbium donor performs better than the LRET probe pair with a Europium donor and a Cy5 acceptor.

Although conventional molecular beacons can in theory detect mRNA transcripts in living cells, conditions within the intracellular environment can limit their utility in cellular imaging of gene expression. Specifically, molecular beacons bound to target mRNAs cannot be distinguished from those degraded by nucleases, or destabilized due to interactions with proteins. The disclosure provides a dual molecular beacon method that combines the advantages of molecular beacons with two-probe energy transfer methods. Conventional and time-resolved fluorescence spectroscopy studies indicate that dual FRET molecular beacon pairs are capable of distinguishing between bound and degraded beacons with improved signal to background than previous methods. Moreover, with a lanthanide chelate as the donor dye, the signal-to-background ratio can be extremely high at certain wavelengths.

These features are especially important in the detection and quantification of gene expression in living cells where false-positive signals due to probe degradation and interaction with DNA binding proteins must be distinguished from the 'true' signal that results from probe/target binding. Widespread applications of the dual energy transfer molecular beacon methods will become common in laboratory and clinical studies of gene expression in cell lysates, tissue extracts, living cells, tissues and even animals using single- or multi-photon microscopy, time-resolved fluorescence microscopy, and fluorescence endoscopy. For example, it is plausible to use this methodology for the specific and sensitive detection of the expression of oncogenes and tumor-suppresser genes in living cells, potentially making it a very simple and effective clinical tool for the early detection and diagnosis of malignancy.

When using the dual LRET molecular beacons for gene detection and quantification examples of chelates that can be employed include DTPA-cs124, BCPDA (4,7-bis(chlorosulfophenyl)-1,10-phenanthroline-2,9-dicarboxylic acid) and BHHCT (4,4-bis(1,1,1,2,2,3,3-heptafluoro-4,6-hexanedion-6-yl)-chlorosulfo-o-terphenyl (Evangelista et al., 1988; Lopez et al., 1993; Yuan et al., 1998; Sueda et al., 2000; Cooper and Sammes, 2000).

Figure 10A:
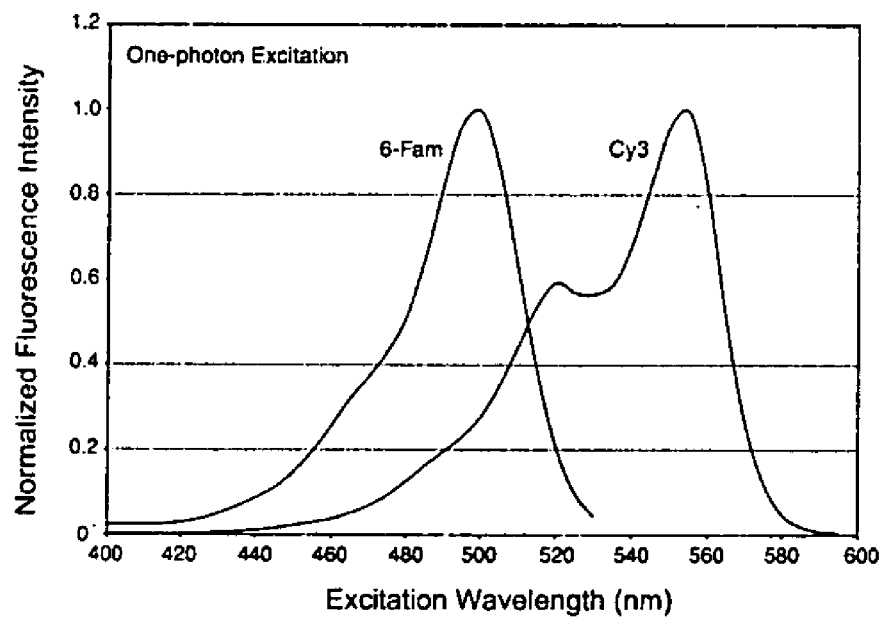
FIGS. 10a and 10b show one-photon (10a) and two-photon (10b) excitation spectra of 6-Fam labeled and Cy3 labeled oligonucleotides.

Another improvement is to use two photon excitation instead of one-photon excitation. So far, all the dual FRET beacon/target hybridization assays performed were based on a one-photon excitation source (Xenon flash lamp). However, because of the overlapping excitation-emission spectrums of the organic donor and acceptor molecules for FRET, it is often difficult to excite the donor without also directly exciting the acceptor For example, as demonstrated in FIG. 10a, the maximum excitation of a donor Fam molecule occurs at ~500 nm, but at the same wavelength an acceptor Cy3 molecule is also excited to 25% of its maximum. Therefore, if an acceptor beacon is degraded by nucleases and the fluorophore is separated from the dabcyl quencher it will be excited, giving a false-positive signal. Ideally, free acceptor fluorophores should be minimally excited by the excitation source and the only ones that are excited would be those due to FRET when both the donor and acceptor beacon are bound to the same target.

Figure 10B:
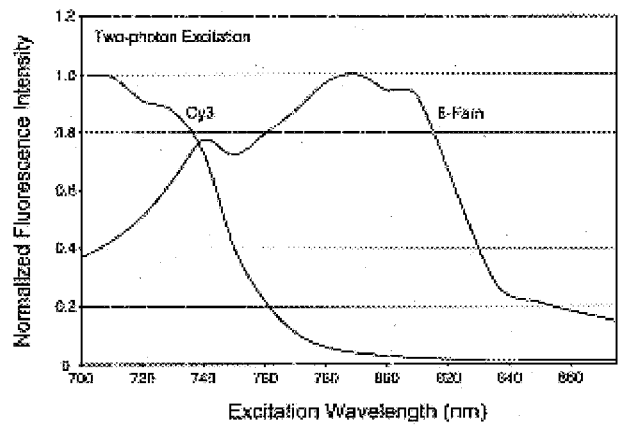

One strategy to minimize the direct excitation of the acceptor fluorophore is to use a two-photon excitation source. Two-photon excitation cross-sections of fluorophores do not necessarily follow the same trends as one-photon excitation spectrums. For example, as shown in FIG. 10b, although the maximum excitation of Cy3 occurs at higher wavelengths than Fam when one-photon excitation is used, with two-photon excitation the Cy3 fluorophore is actually excited at lower wavelengths. Further, when a donor Fam molecule is maximally excited at ~790 nm, the Cy3 acceptor is only excited about 4% of its maximum. This alone is more than a 6-fold reduction in the direct excitation of the Cy3 acceptor compared with one-photon excitation. Two-photon excitation also has the advantage of reduced photo-bleaching, reduced background fluorescence from scattering, and the ability to penetrate deeper into biological tissue than one-photon excitation. Therefore, two-photon excitation is potentially a powerful approach in dual FRET molecular beacon studies.

Example 2

Shared Stem Nucleic Acid Probes

Oligonucleotide Synthesis. Oligonucleotide probes and targets were synthesized using standard phosphoramidite chemistry on an Applied Biosystems model 394 automated DNA synthesizer (Foster City, Calif.). Molecular beacons were purified using a 2-step reverse phase (RP) plus ion-exchange (IE) high performance liquid chromatography (HPLC) on a Waters Model 600E HPLC system (Millipore Corp., Milford, Mass.). For RP-HPLC purification, oligonucleotides were loaded on a Hamilton PRP-1 column and eluted with a linear 5% to 50% acetonitrile gradient in 0.1 M triethyl-ammonium acetate (TEM) pH 7.2 over 40 minutes. The oligonucleotides were additionally purified by IE-HPLC using a Source™ column (Amersham Pharmacia Biotech, Piscataway, N.J.) and eluted with a linear 0% to 50% 1 M LiCl gradient in 0.1 M Tris pH 8.0 over 40 minutes. Unmodified (target) oligonucleotides were purified using polyacrylamide gel electrophoresis. All oligonucleotides were synthesized at Integrated DNA Technologies, Inc. (Coralville, Iowa).

Molecular Beacon Design. Two types of molecular beacons were designed and synthesized; both contain target-specific probe sequence complementary in antisense orientation to exon 6 of the human GAPDH gene, a Cy3 fluorophore at the 5'-end, and a dabcyl quencher at the 3'-end. As illustrated in FIG. 11a, one type follows the conventional design of molecular beacons in that the target-specific probe domain was centrally positioned between two complementary arms that form the stem; the sequence of these arms were independent of the target sequence. Shared-stem molecular beacons, on the other hand, were designed to have one arm of the stem complementary to the target sequence, as shown schematically in FIG. 11b. In both cases, the probe length $L_p$ is defined as the portion of the molecular beacon that is complementary to the target, and the stem length $L_s$ is the number of bases of each complementary arm. All the molecular beacons had $L_p$=19 bases (see Table 3). Conventional molecular beacons were synthesized with $L_s$=4, 5 and 6 bases. The shared-stem molecular beacons were synthesized with $L_s$=4, 5 and 7 bases. As illustrated by FIG. 12a, a 6-base stem may not be synthesized because the shared-stem molecular beacon sequence is constrained, i.e., part of the arm sequence that makes up the 6-base stem is predetermined since the 5'-end of the shared-stem molecular beacon must complement the target sequence and the 3'-stem is created solely to complement the 5'-stem sequence. This inadvertently forces an additional base pairing in the stem. It should be noted that the stem sequence of a shared-stem molecular beacon is not adjustable since one arm of the stem is designed to complement the target. This limitation often precludes the design of certain stem/probe length combinations, as demonstrated in FIG. 12b for a molecular beacon with a probe length of 18 bases and a stem length of 4 bases Five target oligonucleotides were also synthesized, one wild-type and four with mismatches at assorted locations, as shown in Table 3.

TABLE 3

The Design of Probes and Target Oligonucleotides

| Name | Sequence (5'-3') | | Notes |
|---|---|---|---|
| Shared-stem 19/4 | Cy3-GAGTCCTTCCACGATACCActc-Dabcyl | SEQ ID NO:13 | Probe 19/Stem 4 |
| Shared-stem 19/5 | Cy3-GAGTCCTTCCACGATACCAgactc-Dabcyl | SEQ ID NO:14 | Probe 19/Stem 5 |
| Shared-stem 19/7 | Cy3-GAGTCCTTCCACGATACCAggactc-Dabcyl | SEQ ID NO:15 | Probe 19/Stem 7 |
| Conventional 19/4 | Cy3-cctcGAGTCCTTCCACGATACCAgagg-Dabcyl | SEQ ID NO:16 | Probe 19/Stem 4 |
| Conventional 19/5 | Cy3-ctgacGAGTCCTTCCACGATACCAgtcag-Dabcyl | SEQ ID NO:17 | Probe 19/Stem 5 |
| Conventional 19/6 | Cy3-ctgagcGAGTCCTTCCACGATACCAgctca-Dabcyl | SEQ ID NO:18 | Probe 19/Stem 6 |
| Target WT | ACTTTGGTATCGTGGAAGGACTCATGA | SEQ ID NO:19 | Perfect match |
| Target A | ACTTTGGTATCGTGGAAGGAaTCATGA | SEQ ID NO:20 | Single mismatch |
| Target B | ACTTTGGTATCGTaGAAGGACTCATGA | SEQ ID NO:21 | Single mismatch |

TABLE 3-continued

The Design of Probes and Target Oligonucleotides

| Name | Sequence (5'-3') | Notes |
| --- | --- | --- |
| Target C | ACTTTGGTATCGTaGAAGGAaTCATGA | SEQ ID NO:22 Double mismatch |
| Target D | ACTTTGGTATCGTaaAAGGACTCATGA | SEQ ID NO:23 Double mismatch |

[1] Molecular Beacons: Lower case = bases added to create stem domains. Upper case = probe-target hybridizing domains. Upper case bold = bases participating in both stem hairpin and target binding
[2] Targets: Underscore = 19 base sequence complementary to beacons. Lower case bold = mismatch bases in targets Equilibrium Analysis. Molecular beacons in the presence of target were assumed to exist in three phases: 1) as duplex with target, 2) as stem-loop hairpin, and 3) in random coil conformation. Dissociation constants describing the transition between these phases were determined by analyzing the thermal denaturation profile of molecular beacons in the presence and absence of target (Bonnet et al., 1999). Denaturation profiles were obtained by recording the fluorescence intensity of a 50 µL solution containing 200 nM of molecular beacon in the presence of 0 to 20 µM of target at temperatures ranging from 5° C. to 95° C. Specifically, the temperature of the hybridization solution was brought to 95° C. and reduced by 1° C. increments to 5° C. The temperature was then raised with 1° C. increments back to 95° C. to ensure that the solution reached equilibrium and no hysteresis had occurred. The temperature was held at each temperature increment for ten minutes and fluorescence was measured for the final 30 seconds. The fluorescence intensity of each test solution was adjusted to correct for the intrinsic variance of fluorescence over temperature. Each thermal denaturation assay was performed in hybridization buffer containing 10 mM Tris, 50 mM KCl, and 5 mM $MgCl_2$.

The fluorescence intensity data describing the thermal denaturation profile of each molecular beacon and molecular beacon-target duplex was used to determine the respective dissociation constant as described in Bonnet et al. 1999. Specifically, dissociation constants $K_{12}$ characterizing the transition between phase 1 (bound to target) and phase 2 (closed beacon) of molecular beacons were obtained for all beacon-target pairs and for all molecular beacons in the absence of target. Further, the dissociation constants $K_{12}$ were used to determine the changes in enthalpy ($\Delta H_{12}$) and entropy ($\Delta S_{12}$) associated with each beacon-target duplex. The errors calculated for the thermodynamic parameters signify a 95% confidence interval. Molecular Beacon Specificity. The fraction of molecular beacons bound to target, α, was calculated for each molecular beacon-target pair as a function of temperature. All calculations utilized the thermodynamic parameters, enthalpy change $\Delta H_{12}$ and entropy change $\Delta S_{12}$, obtained from the thermal denaturation profiles for each beacon-target duplex $$\frac{\alpha}{(1-\alpha)(\eta-\alpha)\hat{B}_0} = e^{(-\Delta H_{12}/R\theta)+(\Delta S_{12}/R)} \quad (2)$$

where θ is the temperature in Kelvin, R is the gas constant, $\eta=T_0/B_0$, $\hat{B}_0=B_0/c_0$, $T_0$ and $B_0$ are respectively initial concentration of target and beacons, and $c_0$ is the unit concentration 1M (Ratilainen et al., 1998). The value of α was calculated for each molecular beacon-target pair as a function of temperature for samples containing $B_0$=200 nM of molecular beacon and $T_0$=400 nM of target. The melting temperature $\theta_m$ is defined as the temperature at which half of the molecular beacons are bound to target, i.e., α=0.5.

Kinetic Analysis. A SPEX fluorolog-2 spectrofluorometer with an SFA-20 rapid kinetics stopped-flow accessory and a temperature/trigger module (SFA-12) was used to measure molecular beacon-target binding kinetics. Specifically, the fluorescence intensity emitted from a rapidly mixed solution containing 250 nM molecular beacons and 2.5 µM targets was recorded over time for each molecular beacon-target pair. The hybridization reaction was assumed to obey the second order reaction kinetics $$B + T \underset{k_2}{\overset{k_1}{\rightleftarrows}} D, \quad \frac{d[D]}{dt} = k_1[B][T] - k_2[D] \quad (3)$$

where [B], [T] and [D] are the concentrations of unbound molecular beacon, unbound target, and molecular beacon-target duplex, respectively; $k_1$ is the on-rate and $k_2$ the off-rate of molecular beacon-target hybridization. The exact solution of Equation 3 gives $$1 - \frac{[D(t)]}{[D_{eq}]} = e^{-\Delta k_1 t}\left[1 - \lambda \frac{[D(t)]}{[D_{eq}]}\right] \quad (4)$$

where 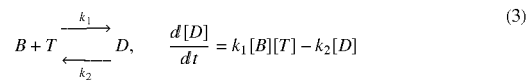, $[D_{eq}]=(B_0+T_0+K_{12}-\Delta)/2$, $\lambda=[D_{eq}]^2/B_0/T_0$, and $K_{12}=k_2/k_1$ is the dissociation constant discussed above. Since the concentration of molecular beacon-target duplex is unknown at any given time, it was assumed that $(F(t)-F_o)/(F_{eq}-F_o)=[D(t)]/[D_{eq}]$ where F(t) is the fluorescence intensity at time t, $F_o$ is the initial fluorescence intensity, and $F_{eq}$ is the fluorescence intensity as t→∞. In order to obtain the on-rate $k_1$ based on the fluorescence measurement, two different curve-fitting schemes were used. The first utilized a least-square method by fitting a straight line to a logarithmic form of Equation 4, $$\frac{1}{\Delta}\ln\left(1 - \frac{\{F(t)-F_o\}}{\{F_{eq}-F_o\}}\right) = \frac{1}{\Delta}\ln\left(1 - \lambda\frac{\{F(t)-F_o\}}{\{F_{eq}-F_o\}}\right) - k_1 t \quad (5)$$

with a slope equal to $k_1$. Alternatively, a non-linear least-square method was used to determine the value of $k_1$ from Equation 4 directly. The results obtained using these two approaches were compared.

Figure 14:
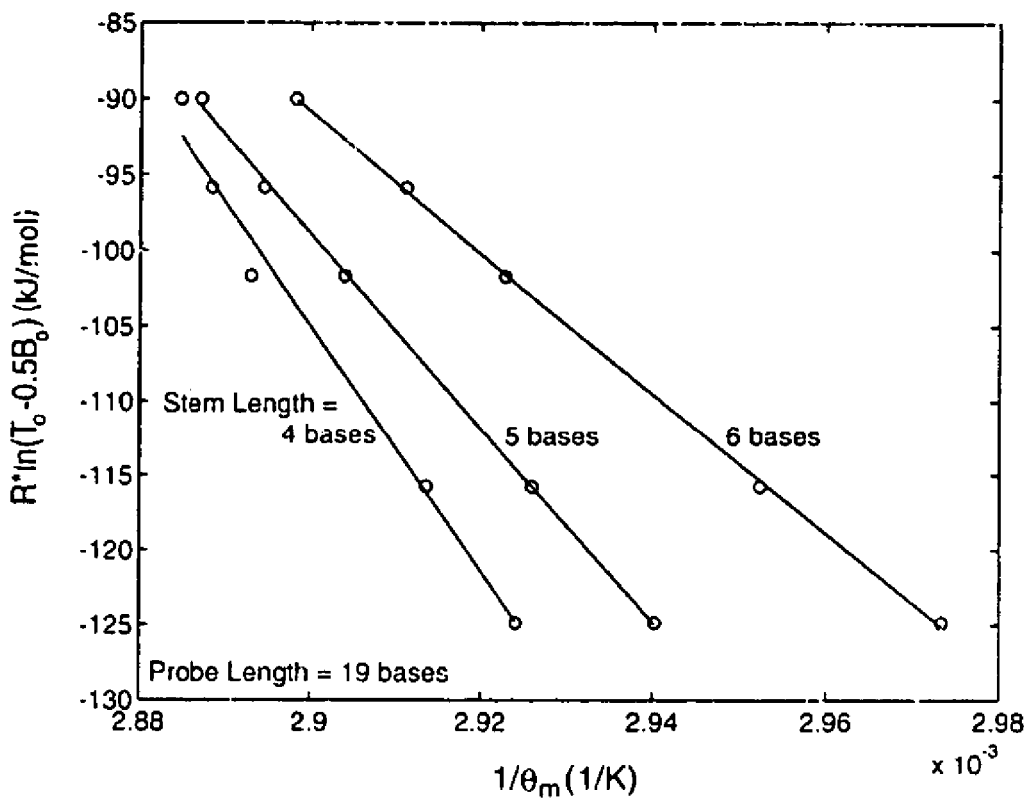
FIG. 14 shows determination of the changes in enthalpy (slope of the fitted line) and entropy (y-intercept) characterizing the phase transition between bound-to-target and stem-loop conformations for conventional molecular beacons. Similar trend was found for shared-stem molecular beacons.

Thermal Analysis. To better understand how the performance of shared-stem molecular beacons differ from that of the conventional molecular beacons, thermodynamic parameters of these two types of molecular beacon were obtained and compared. In particular, the enthalpy and entropy changes $\Delta H_{12}$ and $\Delta S_{12}$ describing the phase transition between bound-to-target and stem-loop conformations were determined for conventional and shared-stem molecular beacons using van't Hoff plots. As demonstrated in FIG. 13, these plots display the inverse of melting temperature $1/\theta_m$ as determined by $R \cdot \ln(T_0 - 0.5B_0)$ shown as the ordinate. Since at melting temperature, $$R \ln(T_0 - 0.5B_0) = -\Delta H_{12} \frac{1}{\theta_m} + \Delta S_{12} \quad (6)$$

the slope of the fitted straight line of each curve in FIG. 13 represents the enthalpy change $-\Delta H_{12}$ and the y-intercept represents the entropy change $\Delta S_{12}$. It was found that in general, the shared-stem molecular beacons have a higher melting temperature, i.e., they form more stable probe/target duplexes than conventional molecular beacons. The changes of enthalpy and entropy for all the molecular beacon-target combinations tested are summarized in Table 4.

conventional molecular beacon do not bind to the target and are thus more likely to interact with each other as driven by thermal energy, increasing the tendency of forming a closed molecular beacon by dissociating from the target. Not surprisingly, the stem length of a molecular beacon influenced the equilibrium state of both the shared-stem and conventional beacons in the presence of target. As shown in FIG. 14, as the stem length was increased from 4 to 6 bases, conventional molecular beacons were found to dissociate from target molecules more readily. A very similar trend was true for shared-stem molecular beacons (data not shown). This indicates that hybridization is less favorable for molecular beacons with longer stems.

Figure 15A:
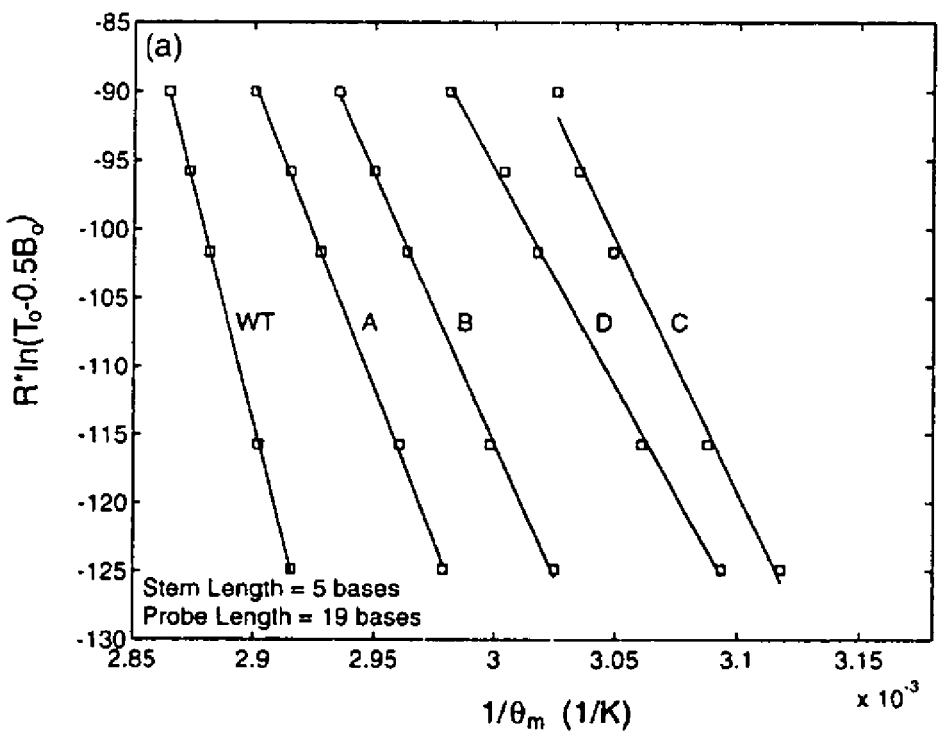
FIGS. 15a and 15b show determination of the changes in enthalpy (slope of the fitted line) and entropy (y-intercept) characterizing the phase transition between bound-to-target and stem-loop conformations for FIG. 15a shared-stem and FIG. 15b conventional molecular beacons interacting with wild-type and mutant targets.

The changes in enthalpy and entropy that control the dissociation of conventional and shared-stem molecular beacons from targets with mismatches were also determined (see Table 4). It was found that shared-stem molecular beacons formed more stable duplexes with each of the target molecules tested. However, as displayed in FIG. 15, when point mutations were present in the target oligonucleotide, both types of molecular beacons dissociated from their targets more readily. The magnitude of change depended on both the number of mismatches and their location. Compared with the wild-type target, a point mutation near the center of the probe-binding domain (Target B) was found to have a larger effect on molecular beacon dissociation than a

TABLE 4

Changes in Enthalpy and Entropy of Conventional and Shared-stem Molecular Beacons in the Presence of Target

| | | | Conventional Molecular Beacons | | Shared-stem Molecular Beacons | | |
|---|---|---|---|---|---|---|---|
| Target | Probe Length | Stem Length | $-\Delta H$ (kJ/mol) | $\Delta S$ (kJ/mol · K) | Stem Length | $-\Delta H$ (kJ/mol) | $\Delta S$ (kJ/mol · K) |
| WT | 19 | 4 | 823 ± 168 | 2281 ± 489 | 4 | 862 ± 116 | 2383 ± 336 |
| A  | 19 | 4 | 577 ± 62  | 1595 ± 184 | 4 | 708 ± 36  | 1967 ± 106 |
| B  | 19 | 4 | 527 ± 27  | 1471 ± 79  | 4 | 586 ± 54  | 1628 ± 161 |
| C  | 19 | 4 | 472 ± 23  | 1336 ± 70  | 4 | 478 ± 49  | 1340 ± 148 |
| D  | 19 | 4 | 480 ± 38  | 1352 ± 115 | 4 | 521 ± 87  | 1461 ± 262 |
| WT | 19 | 5 | 649 ± 28  | 1784 ± 83  | 5 | 690 ± 16  | 1887 ± 46  |
| A  | 19 | 5 | 418 ± 23  | 1133 ± 70  | 5 | 446 ± 20  | 1205 ± 59  |
| B  | 19 | 5 | 385 ± 24  | 1055 ± 73  | 5 | 391 ± 24  | 1057 ± 72  |
| C  | 19 | 5 | 324 ± 17  | 901 ± 54   | 5 | 369 ± 57  | 1025 ± 175 |
| D  | 19 | 5 | 291 ± 25  | 790 ± 76   | 5 | 319 ± 28  | 861 ± 85   |
| WT | 19 | 6 | 467 ± 16  | 1265 ± 48  | 7 | 413 ± 10  | 1096 ± 28  |
| A  | 19 | 6 | 404 ± 25  | 1105 ± 76  | 7 | 370 ± 13  | 998 ± 38   |
| B  | 19 | 6 | 380 ± 26  | 1055 ± 79  | 7 | 351 ± 39  | 956 ± 117  |
| C  | 19 | 6 | 367 ± 19  | 1058 ± 61  | 7 | 260 ± 30  | 707 ± 93   |
| D  | 19 | 6 | 373 ± 29  | 1065 ± 91  | 7 | 245 ± 25  | 653 ± 79   |

To minimize the number of independent variables involved in controlling probe/target hybridization, all the molecular beacons were designed to have identical probe sequences. Further, for molecular beacons with a stem length of 5 bases and a probe length of 19 bases, the stem sequence of the conventional molecular beacons was chosen such that energetically the stem was similar to that of the shared-stem molecular beacons. The free energy changes were calculated using nearest neighbor approximations (Zucker 2000).

The difference in thermodynamic behavior between conventional and shared-stem molecular beacons can be understood in terms of the ability of the flanking arms to interact with each other. With shared-stem molecular beacons, once part of the stem (one arm) is bound to the target, it is less likely to interact with its complementary arm, resulting in a more stable probe/target duplex. In contrast, the arms of a mutation near the end of the probe-binding domain (Target A). As expected, two point mutations (Targets C and D) on a target had a more profound effect on the dissociation of molecular beacons from targets than that with one point mutation.

Melting Temperature. To further elucidate the effect of molecular beacon structure on the stability of the probe-target duplex, the melting temperatures $\theta_m$ for conventional and shared-stem molecular beacons with a probe length of 19 bases and stem lengths ranging from 4 to 7 bases were compared, as shown in FIG. 6. It was found that conventional molecular beacons had lower melting temperatures than shared-stem molecular beacons for each of the stem lengths considered; however, both types of molecular beacons exhibited similar trends. Specifically, the melting temperature progressively decreased as the stem length increased. In fact, it appears that the melting temperature would be quite low for conventional molecular beacons with a probe length of 19 bases and a stem length of 7 bases or greater. This is because that with long free arms of the stem a bound molecular beacon is very easy to dissociate from the target and form a stable hairpin structure even at low temperatures.

Figure 15B:
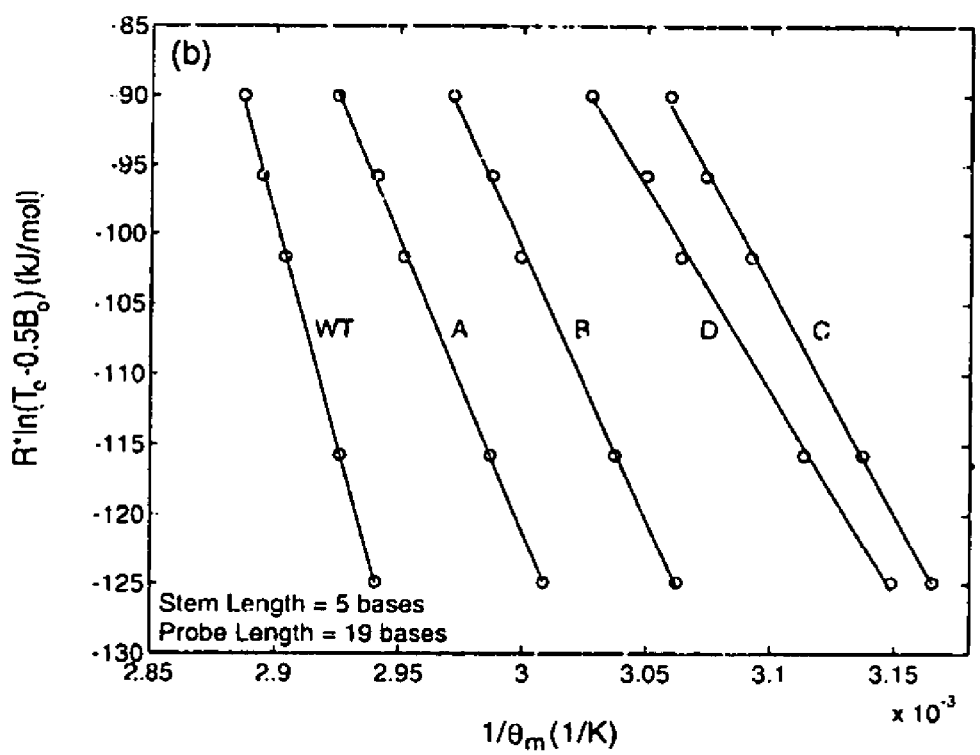
Figure 16:
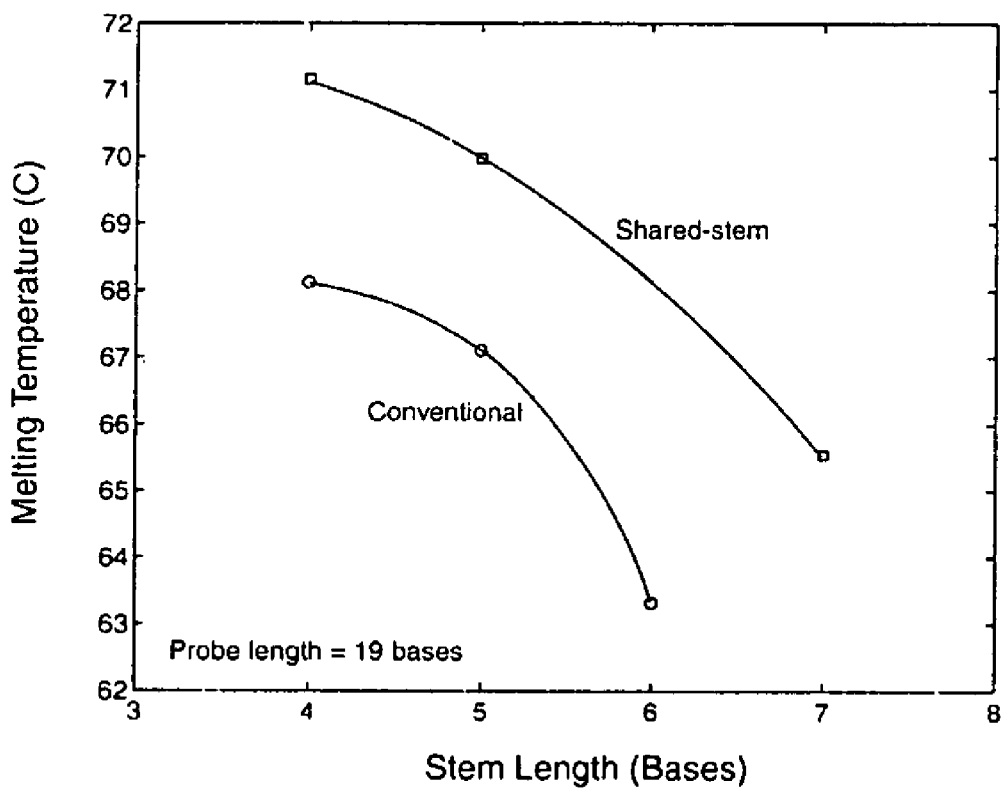
FIG. 16 shows a comparison of melting temperatures as a function of stem length for conventional and hared-stem molecular beacons in the presence of wild-type target.
Figure 17A:
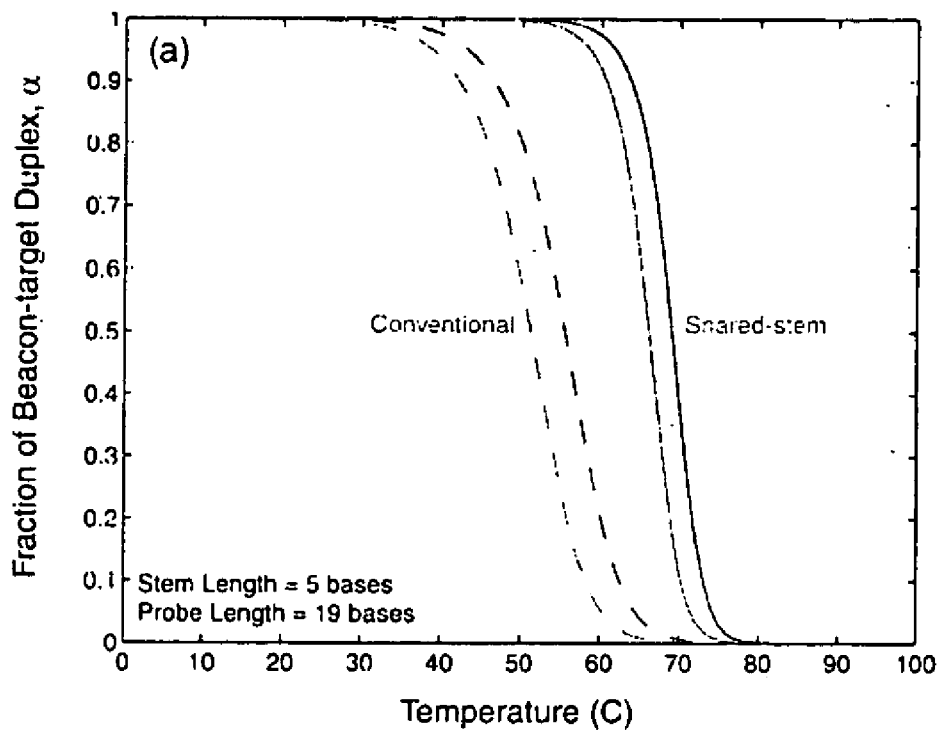
FIGS. 17a and 17b show melting behavior of conventional and shared-stem molecular beacons with a 19-base probe and a 5-base stem.
Figure 17B:
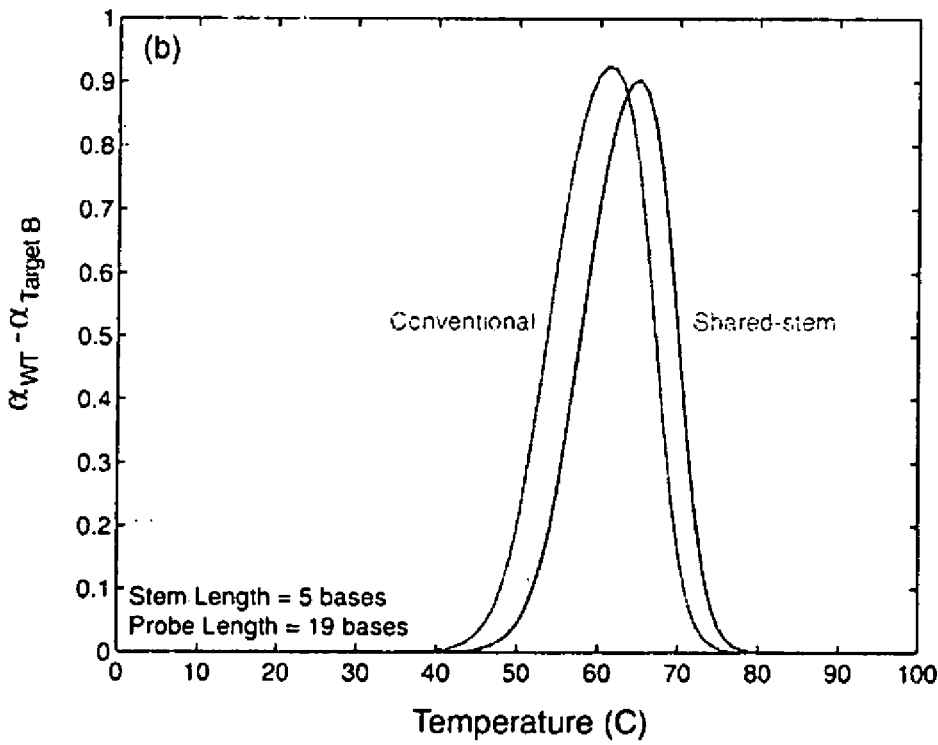

Molecular Beacon Specificity. Melting curves that display the fraction of molecular beacons in duplex form, $\alpha$, as a function of temperature were obtained for each molecular beacon and probe-target pair. As demonstrated in FIG. 17a, the difference in melting temperature $\theta_m$ (i.e., temperature at $\alpha=0.5$) between beacon/wild-type-target and beacon/mutant-target duplexes was found to be slightly larger for conventional molecular beacons compared with corresponding shared-stem molecular beacons. Further, the difference in the fraction of molecular beacons bound to wild-type target and mutant target, $\alpha_{WT}-\alpha_{Target\ B}$, as a function of temperature was found to be similar for conventional and shared-stem molecular beacons, although the maximum value of $\alpha_{WT}-\alpha_{Target\ B}$ is slightly higher for the former, as shown in FIG. 15b. The conventional molecular beacons was also found to maintain a value of $\alpha_{WT}-\alpha_{Target\ B}>0$ over a slightly broader range of temperatures than shared-stem molecular beacons, but again the different is very small. This implies that the conventional molecular beacons may exhibit only a slightly higher specificity than shared-stem molecular beacons.

Figure 18:
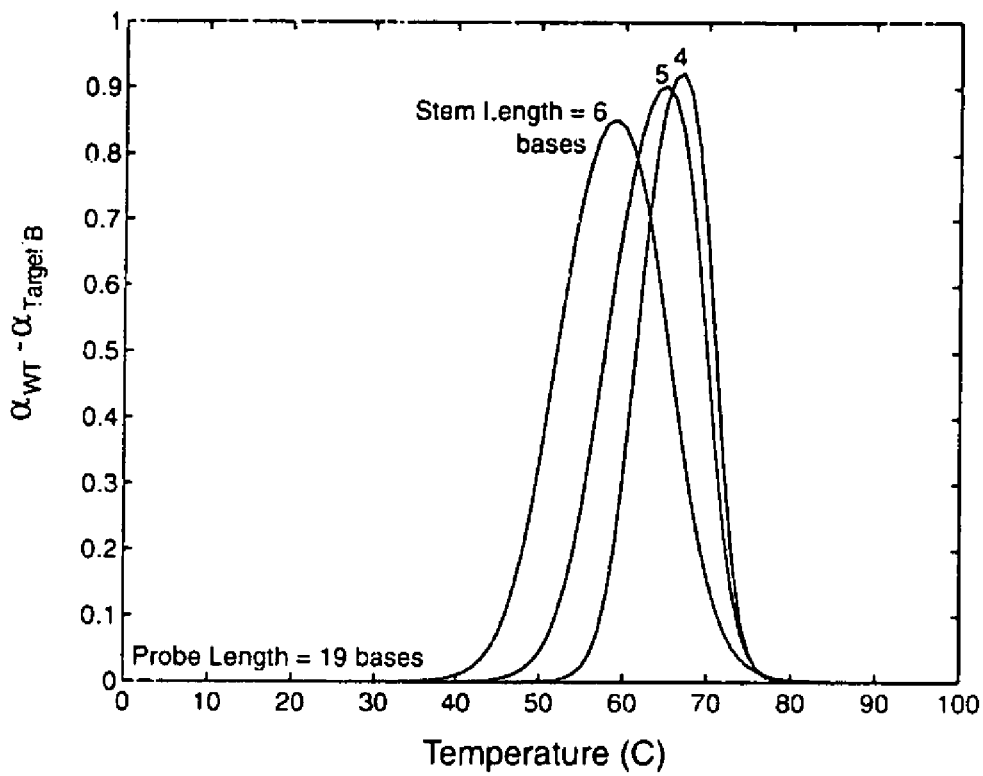
FIG. 18 shows the difference in the fraction of beacons bound to wild-type and mutant targets for shared-stem molecular beacons with stem lengths of 4, 5, and 6 bases. The same trend is true for conventional molecular beacons.

The effect of stem length on molecular beacon specificity was also found to be similar for conventional and shared-stem molecular beacons. Specifically, the curves in FIG. 18 demonstrate that, as the stem length is increased the heightened competition between a unimolecular reaction and bimolecular hybridization broadens the transition between bound and unbound states. This results in an improved ability to discriminate between targets over a wider range of temperature but lowers the maximum difference in the fraction of beacons bound to wild-type and mutant targets.

Figure 19A:
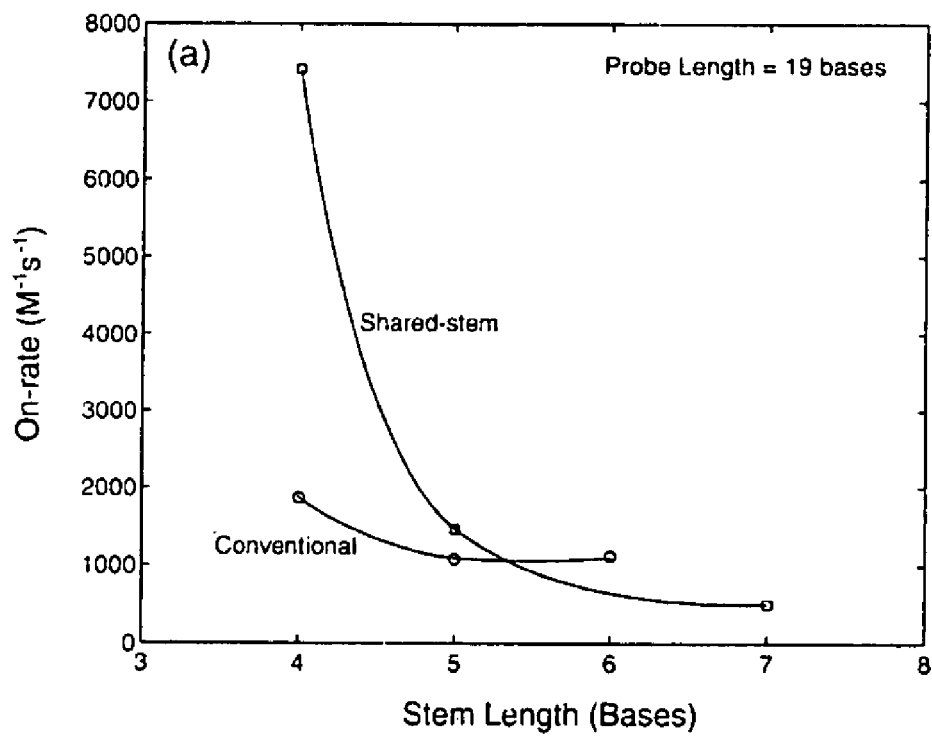
FIGS. 19a and 19b show a comparison between conventional and shared-stem molecular beacons on FIG. 19a the on-rate of hybridization with target and FIG. 19b the dissociation constant without target (i.e., the transition between stem-loop hairpin and random-coiled beacons) for molecular beacons with a 19-base probe length and various stem lengths.
Figure 19B:
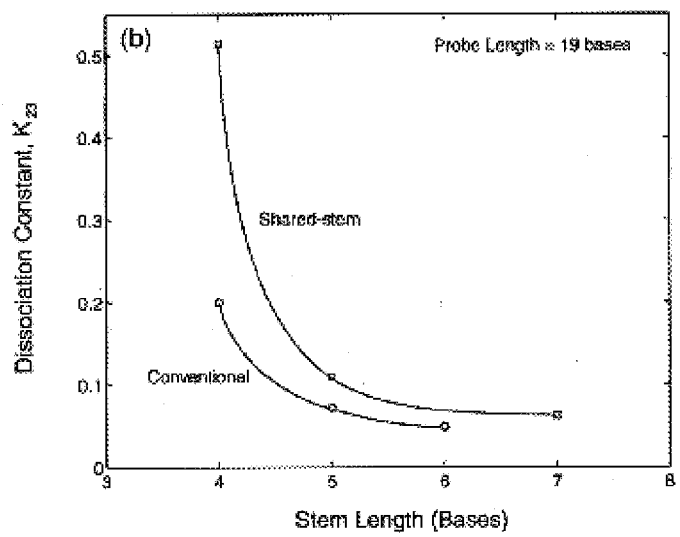

Kinetic Analysis. The on-rate of shared-stem and conventional molecular beacons hybridized to wild-type target as a function of stem length is displayed in FIG. 19a. It is seen that for shared-stem molecular beacons, an increase in stem length from 4 to 5 bases induced a 5-fold reduction in its on-rate, which was further reduced by 3-fold when the stem length was increased from 5 to 7 bases. In contrast, the on-rate of conventional molecular beacons only decreased slightly when the stem length was increased from 4 to 6 bases. It is interesting to note that, with stem lengths of 5 bases or larger, the shared-stem and conventional molecular beacons have on-rates differing only by less than a factor of 2. However, the shared-stem molecular beacons with a 4-base stem hybridized to wild-type targets four times faster than the corresponding conventional molecular beacons. This large difference in the rate of hybridization most likely resulted from the variations in the stability of the hairpin structure. To further illustrate, the dissociation constants $K_{23}$ of the conventional and shared-stem molecular beacons in the absence of target are shown in FIG. 19b. Interestingly, there seems to be a clear correlation between the on-rate of beacon hybridization and the stability of the stem-loop structure. This is understandable since $K_{23}$ represents the transition from hairpin (phase 2) to random coiled (phase 3) conformations of molecular beacons, and a higher $K_{23}$ implies that the molecular beacons are easier to open.

Molecular beacons have become a very useful tool for many homogeneous single-stranded nucleic acid detection assays due to their ability to differentiate between bound and unbound states and their improved specificity over linear probes. However, to optimize the performance of molecular beacons for different applications, it is necessary to understand their structure-function relationships. Here is described a new design of molecular beacons, i.e., the shared-stem molecular beacons, of which the stem-arm nearest the reporter dye participates in both hairpin formation and target hybridization. In contrast to conventional molecular beacons whose stems are independent of the target sequence and thus can freely rotate around the probe-target duplex, this new design helps immobilize the fluorophores of molecular beacons when they hybridize to the target, which is desirable when two molecular beacons are used in a fluorescence energy transfer, for example a fluorescence resonance energy transfer (FRET) assay (Tsourkas and Bao 2001). Specifically, with shared-stem molecular beacons, there is a better control of the distance between the donor dye on one beacon and the acceptor dye on the other beacon, since the rotational motion of the fluorophore-attached stem-arm is constrained, as illustrated in FIG. 11b. To facilitate the design and application of, and to reveal the differences between, shared-stem and conventional molecular beacons, a systematic study of the thermodynamic and kinetic parameters that control the hybridization of these molecular beacons with complementary and mismatched targets was performed.

In general, it was found that compared with shared-stem molecular beacons, conventional molecular beacons form less stable duplexes with single-stranded nucleic acid targets but have a slightly improved ability to discriminate between wild-type and mutant targets. The difference in the duplex stability can be explained by the thermal-driven interactions between the two stem-forming arms after the molecular beacon hybridized to a target molecule. Unlike linear oligonucleotide probes, a molecular beacon can have two stable conformations: bound to target, and as a stem-loop hairpin. These two stable states compete with each other, giving rise to an improved specificity. The additional freedom inherent in both arms of conventional molecular beacon increases the likelihood that, driven by thermal fluctuations, these arms will encounter with each other, allowing the molecular beacon to dissociate from the target with a higher probability. This reduced stability also corresponds to a smaller value in the free energy difference between bound and unbound states of the probe-target duplex. The change in free energy due to any mismatch between the probe and target, therefore, will have a more profound effect on the preference of the stem-loop hairpin conformation of the conventional molecular beacons, leading to an improved ability to differentiate between wild-type and mutated targets. However, this improvement was found to be marginal.

With any given probe length and sequence, the hybridization kinetics of molecular beacons appears to be primarily dependent on the length and sequence of the stem, regardless of whether they are designed in the conventional or shared-stem configuration. Both types of molecular beacons exhibited comparable hybridization rates when the dissociation constants describing the thermal fluctuation induced opening of the stem-loop structure, $K_{23}$, were similar. When the difference in $K_{23}$ for the shared-stem and conventional molecular beacons was increased, so was the difference in the hybridization on-rate.

In addition to the above-mentioned differences in the behavior of shared-stem and conventional molecular beacons, the choice of the stem length is independent of the probe length for conventional molecular beacons, whereas there are certain constraints on the stem-length and probe-length combinations in designing the share-stem molecular beacons. This, together with the dependence of the thermodynamic and kinetic properties on the probe and stem lengths demonstrated in this study, should be considered in the design of molecular beacons for specific applications.

Example 3

K-ras and Survivin Detection

It is well established that cancer cells develop due to genetic alterations in oncogenes and tumor suppressor genes and abnormalities in gene expression that provide growth advantage and metastatic potential to the cells. A critical step in diagnosing and treating cancer in its early stages is to detect cancer cells based on the genetic alterations. An important example is pancreatic cancer, the fifth most fatal cancer in the US. Only 12% of patients diagnosed with pancreatic cancer can survive for one year; the 5-year overall survival rate is approximately 3-5%. The main reason for the poor prognosis of pancreatic cancer is that very few of these cancers can be found early. Current clinical diagnostic procedures such as CT-scan and endoscopic retrograde cholangiopancreatography (ERCP) have a low sensitivity in detecting pancreatic tumors less than 2 cm in size. In spite of the extensive biomedical research efforts during the last few decades, over 90% of the patients with pancreatic cancer have already undergone local and/or distant metastases by the time of diagnosis, often making it too late to cure. Therefore, it is extremely important to detect pancreatic cancer in its early stages based on molecular markers rather than the size of the tumor.

A novel way of achieving early detection of cancer is to identify cancer cells through detection of mRNA transcripts that exist in cancer cells but not in normal cells. Here is demonstrated the dual-FRET molecular beacons of the present disclosure for the early detection of cancer cells.

K-ras is one of the most frequently mutated genes in human cancers. A member of the G-protein family, K-ras is involved in transducing growth-promoting signals from the cell surface. Point mutations of K-ras are found in 80-100% of pancreatic, 40-60% of colon, and 25-50% of lung adenocarcinomas, suggesting that mutant K-ras is a sensitive marker for pancreatic cancer detection. Further, K-ras mutations occur almost exclusively in three hot spots (codons 12, 13 and 61). Most of them are concentrated at codon 12, which facilitates the design of molecular beacons. Since K-ras mutations occur very early in the development of pancreatic cancer, assays targeting K-ras mutations can lead to early detection of pancreatic carcinomas. Other oncogenes and tumor-suppressor genes involved in pancreatic cancer include p53, p16, MADH4, DPC4, BRCA2, MKK4, STK11, TGFBR1 and TGFBR2.

There is increasing evidence recently suggesting that survivin, one of the inhibitor of apoptosis proteins (IAPs), is a good tumor marker for several types of cancers. Survivin is normally expressed during fetal development but not in most normal adult tissues. However, high levels of survivin are detected in many human cancer types and transformed human cells. In particular, a recent study has demonstrated the presence of survivin in 77% (20 out of 26 cases) of pancreatic duct cell adenocarcinomas by immunohistochemistry, immunoblotting and RT-PCR assays. The results from this study also suggested that the expression of survivin is present in early stages of neoplastic transition in pancreatic cancer cells. However, expression of survivin was not detected in pancreatic tissues obtained from 5 normal persons and 12 patients with chronic pancreatitis, nor was it found in inflammatory cells around tumor cells. The absence of survivin expression in normal pancreas, pancreatic tissue of chronic pancreatitis patients and other normal tissues makes it an ideal molecular marker for the detection of pancreatic cancer cells. Although molecular beacons can be designed to target alterations of many oncogenes and tumor-suppressor genes, the detection of K-ras mutations and the expression of survivin in pancreatic cells were investigated.

It has been shown that K-ras mutations can be detected in blood, pancreatic juice and pancreatic tissue samples of pancreatic cancer patients using DNA purification and mutant-enriched PCR followed by single strand conformation polymorphism (SSCP), restriction fragment-length polymorphisms (RELP), or allele-specific oligodeoxynucleotide hybridization (ASOH). Although identification of K-ras mutations by PCR is a fairly sensitive molecular approach, the procedures for PCR and subsequent assays are very time-consuming, making them difficult to become clinical procedures. Furthermore, detection of K-ras mutations in DNA from peripheral blood or pancreatic juice alone is not sufficient for diagnosis of pancreatic cancer since it lacks the specificity for the determination of the cellular origin of the K-ras mutation. A better way to detect pancreatic cancer is to use nucleic acid probes of the present disclosure to detect K-ras mutations in cancer cells directly. Utilization of prior nucleic acid probes to detect K-ras mutations in PCR products of DNA samples isolated from lung cancers has been reported and the specificity has been established. However, to date the use of nucleic acid probes for the detection of mutant K-ras mRNA in intact tumor cells has not been reported. One advantage of using the molecular beacons approach is that a cocktail of multiple such probes can be delivered into cells for different molecular markers of cancer.

An important issue in detecting K-ras mutations in cells is that as a signaling protein the expression level of K-ras mRNA may not be very high (<1,000 copies per cell), even in cancer cells. Further, the secondary structures of K-ras and survivin mRNAs may influence the binding between nucleic acid probes of the present disclosure and the targets. Thus, it is preferred to optimize the design of molecular beacons and the beacon delivery conditions so that high detection specificity and sensitivity can be achieved. By routinely combining the nucleic acid probes of the present disclosure approach with high-sensitivity fluorescence microscopy, it will likely be possible to detect as few as 10 copies of mRNA per cell.

To further examine probe-target hybridization and energy transfer between nucleic acid probes of the present disclosure, dual-FRET molecular beacons were designed and synthesized. Specifically, the molecular beacons were designed to target human GAPDH mRNA. The donor proes were synthesized with a 6-FAM donor fluorophore (D) at the 3' end and a Dabcyl quencher (O) at the 5' end. Similarly, acceptor probes were synthesized with a Cy3 acceptor fluorophore (A) at the 5' end and a Dabcyl quencher (O) at the 3' end (see Table 5 below). The donor and acceptor beacons are chosen such that they are complementary to part of the target sequence. The loop portion, therefore, is 13 bases in length. The synthetic targets mimicking the GAPDH IVT RNA exon 6/exon 7 junction are designed so that the gap between the two beacons hybridizing on the same target is respectively 3, 4, 5 or 6 bases, with 4-base gap being that of the wild-type. All the nucleic acid probes of the present disclosure were synthesized at Integrated DNA Technologies (IDT, Inc).

As illustrated above, thermodynamics and binding kinetics of molecular interactions underlies the design of the nucleic acid probes of the present disclosure. The free energy difference between keeping the stem-loop structure and forming the probe-target duplex is the main driving force for hybridization. The nucleic acid probes of the present disclosure can have three different phases in solution: hairpin, random coil, and probe-target duplex. The relative portions of these phases depend on the structure of the probe, probe and target concentrations, solution chemistry, sequences of the probe and target, and temperature. For example, if the stem length is too large, it will be difficult for the stem-loop probe to open upon hybridization. On the other hand, if the stem length is too small, a large fraction of probes may open due to Brownian forces. Similarly, relative to the stem length, a longer probe may lead to a lower dissociation constant, however, it may also reduce the specificity, since the relative free energy change due to one-base mismatch would be smaller. To further establish the structure-function relationships of probes, one can for example routinely design and synthesize a series of dual-FRET probes for targeting different K-ras codon 12 mutations, such as shown in Table 5. For each pair of donor and acceptor beacons, the donor beacon will contain one of the most common K-ras point mutations in pancreatic cancer such as GGT-GAT transitions (Gly to Asp) or GGT-GTT (Gly to Val), GGT-CGT (Gly to Arg), GGT-TGT (Gly to Cys) transversions. The same acceptor beacon can used with all donor beacons having different mutated sequences. As an example, a specific beacon design for nucleic acid probes of the present disclosure has a probe length of 21 nucleotides, a stem length of 4 nucleotides, and a gap size of 4 nucleotides between the donor and acceptor beacons bound on the same target. One can routinely examine the effect of beacon structure on hybridization rate and specificity by varying: 1) probe length of 17, 19 and 21 bases; 2) stem length of 4 and 5 bases; 3) gap sizes of 4 and 5 bases between donor and acceptor beacons along the target mRNA. For different parameter combinations, kinetic and thermodynamic modeling described above will be performed to build the analysis of the experimental data.

ization studies are carried out by mixing the donor nucleic acid probes of the present disclosure with respectively wild-type K-ras mRNA targets, the corresponding mutated K-ras mRNA targets and survivin targets at different probe/target concentrations. Thermal denaturation profiles are generated and the corresponding transition temperatures obtained. Since the detection specificity depends on the initial concentrations of probes and targets, the results of this study not only demonstrate the detection specificity but also provide guidelines for optimizing beacon delivery conditions. Furthermore, stopped-flow studies of the hybridization kinetic rates are performed with each nucleic acid probe of the present disclosure design and each target type. This helps select the optimal structure of the nucleic acid probes of the present disclosure with the best possible combination of specificity and rate of hybridization.

To address potential issues with secondary structures of the mRNAs, synthetic targets with lengths three to four times the probe length are used in in-solution studies. To further utilize the nucleic acid probes of the present disclosure, total mRNAs of survivin and the mutant K-ras are isolated from pancreatic cancer cells known to carry them, amplified, and in-solution hybridization assays are performed to determine the extent of binding between the nucleic acid probes of the present disclosure and these mRNAs.

As mentioned earlier, in a cellular environment, nucleic acid probes can be degraded by cytoplasmic nucleases. To address this issue, the present disclosure provides probes synthesized with structural modifications such as 2'-O-methyl ODNs. Methylated-probe/target duplexes are more stable than DNA-probe/target duplexes, and methylated nucleic acid probes of the present disclosure hybridize to RNA targets faster than DNA probes. After delivery into primary human dermal fibroblast (HDF) cells, the fluorescence signal of unmodified molecular beacons with a random DNA sequence and methylated nucleic acid probes of the present disclosure with the same sequence are monitored over time to determine how long these probes can survive in a cellular environment.

TABLE 5

Design of Molecular Beacons for K-ras Codon 12 Mutation

```
Wild-type K-ras (Bases 1-78)
  1 ATGACTGAAT ATAAACTTGT GGTAGTTGGA GCTGGTGGCG                           SEQ ID NO:27

41 TAGGcaagAG TGCCTTGACG ATACAGCTAA TTCAGAAT

Dual-FRET Molecular Beacons
Donor Beacon:     5'-Dabcyl-AGTGCGCTGTATCGTCAAGGCACT-6-Fam-3'            SEQ ID NO:28

Acceptor Beacon: 5'-Cy3-CCTACGCCATCAGCTCCGTAGG-Dabcyl-3'    Mut: GGT-GAT  SEQ ID NO:29

Acceptor Beacon: 5'-Cy3-CCTACGCCAACAGCTCCGTAGG-Dabcyl-3'    Mut: GGT-GTT  SEQ ID NO:30

Acceptor Beacon: 5'-Cy3-CCTACGCCACGAGCTCCGTAGG-Dabcyl-3'    Mut: GGT-CGT  SEQ ID NO:31

Acceptor Beacon: 5'-Cy3-CCTACGCCACAAGCTCCGTAGG-Dabcyl-3'    Mut: GGT-TGT  SEQ ID NO:32
```

To further increase the detection sensitivity, for example, one can synthesize nucleic acid probes of the present disclosure to target a second cancer marker, such as survivin, which is expressed in pancreatic carcinomas but not in normal tissues. To demonstrate the specificity of molecular beacons targeting K-ras point mutations, in-solution hybrid- To determine the specificity of the molecular beacons approach for detecting K-ras mutations in pancreatic cancer cells, nucleic acid probes of the present disclosure are synthesized to target four different K-ras codon 12 mutations (GGT-GAT, GGT-GTT, GGT-CGT and GGT-TGT). Delivery, hybridization and imaging assays are carried out using pancreatic cancer cell lines such as Panc-1 (GGT to GAT), Capan-1 (GGT to GTT), PSN-1 (GGT to CGT), and Miapaca-2 (GGT to TGT) with the corresponding mutant K-ras mRNAs. Also used is the pancreatic cell line BXPC-3 as a control which has the 'wild-type' K-ras mRNA.

Preliminary studies have shown that the K-ras codon 12 mutation GGT-GAT in Panc-1 cell lines has been confirmed. Further confirmation of the other three mutations (GGT-GTT, GGT-CGT and GGT-TGT) in the corresponding pancreatic cancer cell lines using PCR amplification of K-ras exon 1 sequence followed by DNA sequencing is routinely performed. The K-ras mRNA concentration in each cell line is also be quantified using real time RT-PCR. During a pilot study, the delivery, hybridization, and buffer conditions for the nucleic acid probes of the present disclosure have been optimized to target mutant K-ras mRNA in Panc-1 cells (with GGT to GAT mutation). As mentioned earlier, the disclosure provides a preferred condition for this type of probe of 150 nM of the probes in Opti-MEM 1 medium (GIBCO) and incubated at 37° C. for 30 to 60 minutes. It is anticipated that the optimal delivery and hybridization conditions for nucleic acid probes of the present disclosure targeting different mutant K-ras mRNAs may vary from those identified. Nucleic acid probes of the present disclosure designed for each specific K-ras mutation are incubated with at least four cell lines with the optimal delivery condition; these cell lines include the cell line containing the specific K-ras mutation, the 'wild-type' K-ras cell line BXPC-3, and two other cell lines with different K-ras mutations. The FRET-induced fluorescence signal in cells can be imaged using a confocal microscope. The specificity of the present probe detection methodology is confirmed when strong fluorescence signal are observed only in the cell line expressing the corresponding K-ras mutation but not in BXPC-3 nor other cell lines.

Similar assays are routinely performed to examine the specificity of survivin-targeting nucleic acid probes of the present disclosure using pancreatic cancer cell lines expressing different levels of survivin gene as well as the normal human fibroblast cells as a control. For example, using RT-PCR and Northern blotting, the level of survivin expression in pancreatic cell line Miapaca-2 has been found to be high, in BXPC-3 it is much lower, while in HDF the expression level is almost zero. The probe sequence of the survivin probes is shown in Table 6 and the steps of the assay are similar to that described above. The tumor cell lines expressing different levels of survivin mRNA and the normal cell line HDF are incubated with the survivin nucleic acid probes of the present disclosure, and the resulting fluorescence are imaged using a confocal microscope.

A critical issue concerning the specificity of detecting pancreatic cancer cells is that both K-ras codon 12 mutations and survivin are being expressed in colorectal and lung cancers as well. To assure high specificity for detecting cancer cells originated from the pancreatic ducts, in addition to using nucleic acid probes of the present disclosure targeting survivin and K-ras mutations, a third probe pair for the chymotrypsinogen gene can be synthesized, which is pancreas-specific. An example of the design of donor and acceptor probes are respectively: donor probe: 5'-AMCA-ACCTGGATGTTGTCCTCGTCAGGT-dabcyl-3' SEQ ID NO:36 and acceptor probe: 5'-dabcyl-AAGATTGAAGACCTTGGCGATCTT-Diakylamino coumarin-3' (underlined bases are complementary bases to form a stem) SEQ ID NO:37. This nucleic acid probe pair of the present disclosure will be delivered into pancreatic, lung and colon cancer cell lines as well as the normal human fibroblast cell line HDF and the resulting fluorescence images recorded. This will assure that only cells originated from pancreatic duct are detected. All the detection assays with cells are performed at 37° C. The assays determining detection specificity with lanthanide-dye based nucleic acid probes of the present disclosure are carried out using a Safire monochromator reader (Tecan).

To determine the sensitivity of the probe-based methodology in detecting pancreatic cancer cells, pancreatic cancer and normal cells are mixed with 1:1,000 (i.e., one cancer cell in 1,000 normal cells), 1:10,000, 1:100,000 and 1:1,000,000 ratios and incubate the mixture with the dual-FRET molecular beacons designed for the specific cancer cell line under optimized conditions (probe concentration and duration). After placing cells on glass coverslips, FRET-induced fluorescence images of the hybridized nucleic acid probes of the present disclosure in cancer cells are obtained using a confocal microscope. Further, a FACS Vantage SE cell sorter (Becton-Dickinson) is used to sort out the cancer cells in the mixture in suspension. The cell sorter, which has a sorting sensitivity of 1:100,000, has three excitation wavelengths: 488 nm, 547 nm, and UV. The fluorescence emission due to dual-FRET probes in cells can be detected by using the proper filter. The dual-FRET probe pairs for detecting survivin, K-ras mutations and chymotrypsinogen are so designed such that the donor dye molecules are respectively excited with laser at 353 nm, 488 nm and 547 nm. A fluorescence intensity threshold in the detection is chosen such that the effect of background due to autofluorescence of cells and digested nucleic acid probes of the present disclosure is minimized. In this study, the pancreatic cell lines Panc-1, Capan-1, PSN-1 and Miapaca-2 are used

TABLE 6

Design of Molecular Beacons for Survivin mRNA

```
Survivin (Bases 1-121)
  1 A TGGGTGCCCC GACGTTGCCC CCTGCCTGGC AGCCCTTTCT            SEQ ID NO:33

42 CAAGGaccaC CGCATCTCTA CATTCAAGAA CTGGCCCTTC

82 TTGGAGGGCT GCGCCTGCAC CCCGGAGCGG ATGGCCGAGG

Dual-FRET Molecular Beacons
  Donor Beacon:    5'-Alexa546-CCTTGAGAAAGGGCTGCCCAAGG-Dabcyl-3'     SEQ ID NO:34

Acceptor Beacon: 5'-Dabcyl-CCGCATTGAATGTAGAGATGCGG-Texas Red-3'    SEQ ID NO:35
``` as cancer cells, and a human dermal fibroblast cell line (HDF) serves as normal cells.

In obtaining images of hybridized molecular beacons in cancer cells, having ultra-sensitive fluorescence measurements is important, since typically only a very small number of cancer cells are present in a sample. The FACS Vantage Flow Cytometer (cell sorter) will be used due to its very high detection sensitivity, capability of 5 color analysis and sorting, wide flexibility of excitation wavelengths, and cross beam laser compensation for separation of overlapping excitation. An imaging analysis will also be carried out to enhance the results of FRET fluorescence measurements. In this example, in carrying out imaging assays of detection sensitivity, only nucleic acid probes of the present disclosure with organic dye pairs for FRET will be used, since currently the Zeiss confocal microscope and the FACS cell sorter do not have an imaging capability with time resolved FRET.

This example is based on the rational that detection of tumor markers including survivin and mutant K-ras mRNAs in pancreatic duct cells using dual-FRET nucleic acid probes of the present disclosure can lead to early diagnosis of pancreatic cancer especially in high-risk patients. It demonstrates that the novel dual-FRET molecular beacons methodology of the present disclosure has the potential to become a simple clinical procedure for early detection of pancreatic cancer with high sensitivity, specificity, signal-to-noise ratio, and efficiency. This is further demonstrated with subsequent translational research using clinical samples. The same methodology can be routinely extended to the early detection and diagnosis of other cancers, and the study of gene expression in live cells relevant to solving other biomedical problems.

Example 4 mRNA Detection in Living Cells

To facilitate subsequent studies of early cancer detection, the K-ras-targeting molecular beacons were designed such that the donor beacon is complementary to a region of the K-ras gene containing codon 12 whose mutations are involved in many cancers. The survivin-targeting molecular beacons were designed such that the target sequence is unique, having no overlap with other genes in the IAP family. As shown in Table 7, a BHQ-2 quencher was attached to the 3'-end and a Cyanine 3 (Cy3) fluorophore was attached to the 5'-end of the random beacon and donor molecular beacons; a BHQ-3 quencher was attached to the 5'-end and a Cyanine 5 (Cy5) fluorophore was attached to the 3'-end of the acceptor molecular beacons. The probe lengths of K-ras-targeting donor and acceptor molecular beacons are respectively 17 and 19 bases; the probe lengths of survivin-targeting donor and acceptor molecular beacons are 15 and 16 bases, respectively. The random beacons have a probe length of 16 bases. All molecular beacons are with the shared-stem design, with a stem length of 5 bases; they have unmodified oligonucleotide backbone. The K-ras and survivin molecular beacons and Cy5 random beacon were synthesized by Biosource International (Camarillo, Calif.) and MWG Biotech (High Point, N.C.). The Cy3 random beacon and all of the synthetic targets were synthesized by Integrated DNA Technologies, Inc. (Coralville, Iowa).

TABLE 7

Target sequences and the design of molecular beacons

| | |
|---|---|
| Wild-type K-ras target (Bases 1-78) | |
| 5'-ATGACTGAATATAAACTTGTGGTAGTT | SEQ ID NO:56 |
| GGAGCTGGTGGCGTAGGcaag | |
| AGTGCCTTGACGATACAGC TAATTCAGAAT-3' | |
| K-ras dual FRET molecular beacons | |
| Donor MB: | |
| 5'-/Cy3/*CCTACGCCACCAGCTCC*GTAGG/ | SEQ ID NO:57 |
| BHQ-2/-3' | |
| Acceptor MB: | |
| 5'-/BHQ-3/AGTGCGCTGTATCGTCAAGGCACT/ | SEQ ID NO:58 |
| Cy5/-3' | |
| Survivin target (Bases 1-78) | |
| 5'-ATGGGTGCCCCGACGTTGCCCCCTGCC | SEQ ID NO:59 |
| TGGCAGCCCTTTCTCaagg | |
| ACCACCGCATCTCTAC ATTCAAGAACTGGCCC-3' | |
| Survivin dual FRET molecular beacons | |
| Donor MB: | |
| 5'-/Cy3/*GAGAAAGGGCTGCCA*TTCTC/ | SEQ ID NO:60 |
| BHQ-2/-3' | |
| Acceptor MB: | |
| 5'-/BHQ-3/ACCACGTAGAGATGCGGTGGT/ | SEQ ID NO:61 |
| Cy5/-3' | |
| 'Random' sequence target | |
| 5'-ATCGGTGCGCTTGTCG-3' | |
| 'Random' sequence molecular beacon | |
| Donor MB: | |
| 5'-/Cy3/CACGTCGACAAGCGCACCGATACGTG/ | SEQ ID NO:62 |
| BHQ-2/-3' | |
| Acceptor MB: | |
| 5'-/BHQ-3/ACGTGCGACAAGCGCACCGATCACGT/ | SEQ ID NO:63 |
| Cy5/-3' | |

Solution Assays of Probe-target Hybridization.

All solution studies of probe-target hybridization were carried out in a 1×PBS buffer without calcium and magnesium using a Safire fluorescent microplate fluorometer (Tecan, Zurich, Switzerland), with 545 nm Cy3 (donor) excitation and 560 nm to 680 nm emission detection. Concentrations of 200 nM donor, 200 nM acceptor molecular beacons and 200 nM target were used in a total volume of 50 µL.

Cell Culture and Stimulation

Normal human dermal fibroblasts (Cambrex, N.J.) were grown in Clonetics fibroblast growth medium supplemented with 2% fetal bovine serum (Cambrex, N.J.), insulin, fibroblast growth factor, Gentamicin Sulfate and Amphotericin-B. HDF cells used for stimulation studies were allowed to grow for 24 h before starved with Clonetics fibroblast growth medium supplemented with 0.1% fetal bovine serum and no other supplements for 24 h. They were then stimulated with typical growth medium containing 20% fetal bovine serum. MIAPaCa-2 (ATCC, VA) pancreatic carcinoma cells were grown in DMEM supplemented with 10% FBS, 2.5% horse serum and 50 U/ml of penicillin and 50 μg/ml of streptomycin.

Molecular beacon delivery using reversible permeabilization. Molecular beacons were delivered into living cells using a reversible permeabilization method with streptolysin O (SLO), which was shown to be rapid, efficient, less damaging, and more versatile (in terms of cell type) compared with conventional transfection methods. Specifically, SLO was activated first by adding 5 mM of TCEP to 2U/ml of SLO for 30 min at 37° C. Cells grown in 24-well plates were incubated for 10 min in 200 μL of serum free medium containing 0.2 U/ml of activated SLO (0.5 U SLO per $10^6$ cells) and 5 μL of each molecular beacon type for cell permeabilization and beacon delivery. Cells were then resealed by adding 0.5 ml of the typical growth medium and incubated for 1 hr at 37° C. before performing fluorescence microscopy imaging.

Fluorescence microscopy imaging. Fluorescence imaging of live cells was performed using a Zeiss Axiovert 100 TV epifluorescence microscope coupled to a Cooke Sensicam SVGA cooled CCD camera. For assays using dual FRET molecular beacons, excitation and emission detection were performed using 545 nm and 665 nm filters, respectively. For single beacon assays using either donor beacon alone, or the random beacons, a filter of 570 nm was used for fluorescence detection. Exposure time of 2 s was used for all imaging assays. Maximum signal to background ratios were calculated based on the maximum signal intensity in cells within the field of view divided by the average background pixel value from a portion of the field of view not containing any cell.

RT-PCR Assay. Total RNA was isolated from HDF cells using a Qiagen RNeasy Mini Kit. The yield was 15 šg/ml for stimulated HDFs and 37 šg/ml for non-stimulated HDFs. The cDNA synthesis was performed using Invitrogen's Thermoscript RT-PCR kit with 150 ng of RNA and priming with random hexamers. The forward primier used for K-ras was GATTCCTACAGGAAGCMGT (SEQ ID NO: 64), and reverse primer was TMTGGTGMTATCTTC (SEQ ID NO: 65). For GAPDH, the forward primer used was CCAC-CCATGGCAAATTCCATGGCA (SEQ ID NO: 66) and the reverse primer was TCTAGACGGCAGGTCAGGTC-CACC (SEQ ID NO: 67). PCR conditions were as follows: 95° C. for 5 mins, followed by 95° C. for 30 sec, 52° C. for 30s, and 720 for 1 min (repeated for each cycle) with tubes removed after 15, 20, 25, 30, 35, and 40 cycles. Samples were run through on a 1% agarose gel and stained with EtBr.

Fluorescence in-situ hybridization. Normal human dermal fibroblast cells were cultured in 8-well chambered coverslides for 24 hours in normal growth medium (FGM-2 Cambrex Co.) and then washed with 1×PBS (without Ca or Mg). The slide was fixed in 100% methanol at −20° C. for 10 minutes. After removing the methanol, the slides were allowed to air dry and stored overnight at −80° C. In-situ hybridization assays were then performed by first washing the slides for 5 minutes in 1×PBS and hybridizing them overnight at 37° C. in 1×PBS (no Ca or Mg) containing 400 nM of fluorescently labeled linear probes targeting wild-type K-ras (5'-Cy5-CCTACGCCACCAGCTCC-3') (SEQ ID NO: 68) or as a control (5'-Cy5-AAAAAAAAAAAAAAAAAA-3') (SEQ ID NO: 69). After removing the hybridization solution with washing and adding 1×PBS, the cells were imaged using an Axiovert 100 epi-fluorescent microscope In this Example, three molecular beacon FRET pairs were designed, synthesized and tested in solution. Each FRET probe pair consisted of two molecular beacons, one labeled with a donor fluorophore (donor beacon) and a second labeled with an acceptor fluorophore (acceptor beacon). These molecular beacons were designed to hybridize to adjacent regions on an mRNA target so that the two fluorophores will lie within the FRET range (~6 nm) when probe/target binding occurs for both beacons. Excitation of the donor fluorophore then results in fluorescence emission at a wavelength characteristic of the acceptor fluorophore, which serves as a positive FRET signal readily differentiable from non-FRET false-positive signals due to probe degradation and non-specific probe opening. As shown in Table 7, dual FRET molecular beacon pairs were designed in a shared-stem fashion, i.e., the sequence of the fluorophore-attached arm of the stem (FIG. 1) is complementary to the target so that it participates in both stem formation and target hybridization. This design was chosen to help fix the relative distance between the donor and acceptor fluorophores and improve energy transfer efficiency. For all FRET molecular beacons pairs, Cy3 (peak excitation at 545 nm) and Cy5 (peak emission at 665 nm) were used as the donor and acceptor fluorophores, respectively, and BHQ-2 and BHQ-3 were used as quenchers for the donor and acceptor molecular beacons, respectively One pair of molecular beacons targets a segment of the wild-type K-ras gene (Table 7) whose codon 12 mutations are involved in the pathogenesis of many cancers. A member of the GTPases family, K-ras is involved in regulating cell growth, proliferation and differentiation. As shown in Table 7, the target sequence for K-ras-targeting donor beacon has 17 bases (red), and that for the acceptor beacon has 19 bases (blue). The other pair of molecular beacons targets the survivin gene, which is a member in the inhibitor of apoptosis protein (IAP) family. The target sequences for survivin-targeting donor and acceptor molecular beacons are respectively 15 bases (red) and 16 bases (blue) long. For both K-ras- and survivin-targeting molecular beacon pairs, the stem size is 5 bases, and the gap size between the donor and acceptor beacons on a target is 4 bases. For use in negative controls, Cy3- and Cy5-labeled 'random'-sequence molecular beacons ('random beacon') whose specific 16-base target sequence does not match with any mammalian gene were designed. Note that both the donor (Cy3-labeled) and acceptor (Cy5-labeled) random beacons have an identical sequence, and the 'random sequence' target is for a signal beacon only (Table 7).

Figure 22:
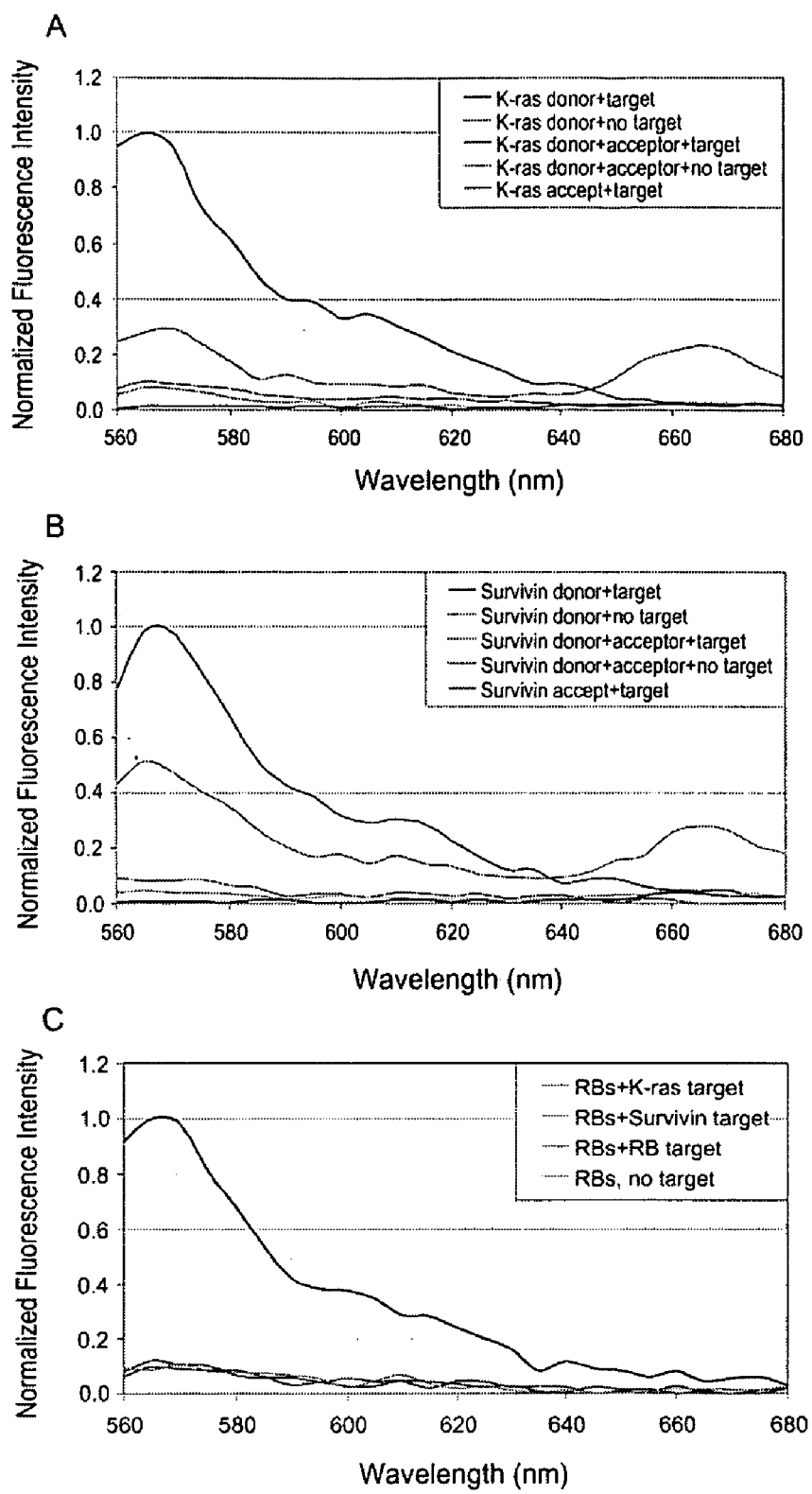
FIGS. 22A-C are line graphs showing results of solution studies of probe-target hybridization of exemplary dual FRET molecular beacons. (a) Fluorescence emission spectra of K-ras targeting molecular beacons under Cy3 excitation (545 nm). (b) Emission spectra for survivin-targeting molecular beacons. (c) Emission spectra for 'random sequence' molecular beacons (RBs) with respectively complementary targets (blue curve), survivin targets (red curve), K-ras targets (green curve) and no target (light blue curve), indicating very high hybridization specificity.

Solution studies of FRET signal and specificity. In-solution probe-target hybridization studies were carried out to determine the extent of energy transfer between, and signal-to-background ratio of, dual FRET molecular beacons, as well as the specificity of the random beacon. Shown in FIG. 22A are five fluorescence emission spectra of molecular beacons targeting wild-type K-ras under Cy3 excitation (545 nm); they were generated by having: (1) donor beacons only in the presence of target (blue curve), representing the signal of a single beacon assay; (2) both donor and acceptor beacons in solution with target (green curve), representing the FRET signal; (3) donor beacons only without target (red curve), representing the background of a single-beacon assay; (4) donor and acceptor beacons in solution without target (light blue curve), representing the background of a FRET assay and (5) acceptor beacons with target (black curve). These results implies that, even when a large amount of single (donor or acceptor) molecular beacons are degraded by nucleases or open due to non-specific interactions, the resulting fluorescence signal at the FRET detection wavelength of 665 nm (dark blue curve) is still much lower than the FRET signal (green curve). The FRET signal-tobackground ratio (green curve vs. light blue curve at 665 nm) is approximately 9.0. The survivin-targeting molecular beacons under Cy3 excitation (545 nm) exhibited essentially the same spectroscopic features, as shown by the five curves in FIG. 22B. When the random beacons were mixed respectively with the complementary random-sequence target, or the wild-type K-ras target, or the survivin target, only targets complementary to the probe sequence of random beacons gave strong fluorescence signal, other targets gave very low background (FIG. 22C), confirming the high specificity of random-sequence molecular beacons.

Figure 23:
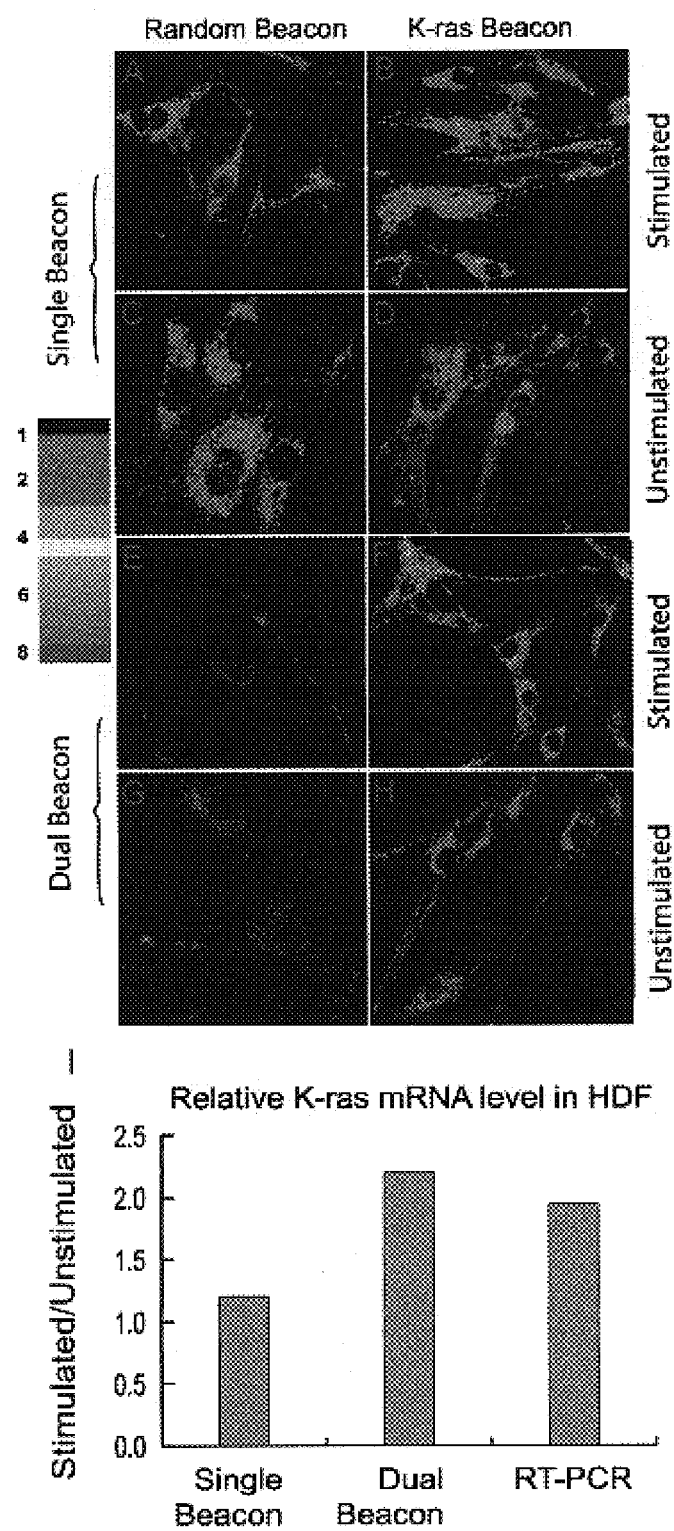
FIGS. 23A-H are fluorescence micrographs showing the detection of K-ras mRNA expression in normally-growing and stimulated HDF cells using single donor molecular beacons only (a-d), or dual FRET molecular beacons (e-h).
FIG. 23I shows a bar graph indicating dual FRET molecular beacons give a much better signal-to-background ratio, and a more quantitative measure of mRNA expression level than single beacons.

K-ras mRNA detection in normally-growing and stimulated HDF cells. In order to demonstrate the advantages of the dual FRET molecular beacons approach, living cell assays were performed with both normally-growing and stimulated HDF cells. To increase the K-ras mRNA expression level, HDF cells were first starved for 24 h and then stimulated with serum for 8 h before molecular beacon delivery. Cells were permeabilized using streptolysin O (SLO) and were exposed to either Cy3-labeled random-sequence or K-ras-targeting single molecular beacons, or Cy3- and Cy5-labeled random-sequence or K-ras-targeting donor and acceptor molecular beacon pairs. The resulting fluorescence signal was observed under Cy3 excitation (545 nm) 1 h after beacon delivery with the Cy3 emission channel (570 nm) for single beacon assays and Cy5 emission channel (665 nm) for dual beacon assays (FIGS. 23A-H). Signals from the single random beacon negative controls (FIGS. 23A and 23C) should be due entirely to beacon degradation, non-specific interactions and possibly other backgrounds such as autofluorescence of the cell. Signals from single Cy3-labeled (i.e., unpaired donor) K-ras-targeting molecular beacons (FIG. 23B) were not appreciably greater than those found with random beacons (FIG. 23A), clearly demonstrating the limitation of using single molecular beacons in RNA detection in living cells, especially when the expression level is relatively low. With stimulated HDF cells, the fluorescence signal level in single beacon K-ras detection increased (FIG. 23D), but it was still not much higher then the corresponding background signal (FIG. 23C).

When random beacon FRET pairs were delivered into either normally-growing or stimulated HDF cells, the resulting FRET signals detected in the Cy5 channel were very low (FIGS. 23E and 23G). The expression levels of K-ras mRNA in normally-growing and stimulated HDF cells were detected using the dual FRET molecular beacons, and the resulting fluorescence signals are shown respectively in FIGS. 23F and 23H, respectively. Even with unstimulated HDF cells, the fluorescence signal as a result of K-ras mRNA detection (FIG. 23F) was much higher than the background (FIG. 23E), indicating that dual FRET molecular beacons are capable of distinguishing true and false-positive signals, which is in sharp contrast with the results of single beacon detection shown in FIGS. 23A and 23B. With stimulated HDF cells, the fluorescence signal level as a result of the dual FRET molecular beacon detection of K-ras mRNA had a significant increase, as shown in FIG. 23H.

Quantitative analysis of the average signal intensities of the images in FIGS. 23F and 23H gave a factor of 2.25 increase in K-ras expression in stimulated HDF comparing with that in normally-growing cells, consistent with the result of the RT-PCR assay, which indicated a factor of 1.95 increase in K-ras expression after stimulation. In contrast, single-beacon detection assays yielded an increase of only a factor of 1.2 (FIG. 23I). This clearly demonstrates that the dual-FRET molecular beacons approach has much better detection sensitivity and allows for a more quantitative measurement of relative changes in mRNA level in living cells upon stimulation. This capability is important for both basic biological studies and drug discovery research in which it is critical to quantify changes of gene expression in living cells in response to stimuli including hormones, growth factors, candidate drug molecules and other chemical/mechanical insults.

In comparing the ratios of K-ras mRNA expression in stimulated and unstimulated HDF cells, it was assumed that the K-ras expression level in different cells imaged simultaneously is roughly the same, which is supported by FIGS. 23B, 23D, 23F and 23H. Consequently, although the quantitative analysis of fluorescence intensity was performed based on, and averaged over, only a few cells, the results should remain valid when a large number of cells are examined. Therefore, the ratios of 1.2 (single-beacon) and 2.25 (dual-beacon) given in FIG. 23I represent fairly accurately the difference in K-ras mRNA detection using single and dual molecular beacon approaches. Further, the result of dual-beacon FRET detection is more accurate than that of the single-beacon approach, since it yielded a much lower background signal as demonstrated by FIGS. 23A, 23C, 23E and 23G. However, when specific mRNA expression has large variations from cell to cell, analyses of fluorescence intensity of only a few cells may not be statistically significant and the results may not be reproducible. In this case the fluorescence intensity of a large number of cells (say, at least a few hundred cells) must be analyzed in order to obtain accurate quantification of mRNA expression.

Figure 24:
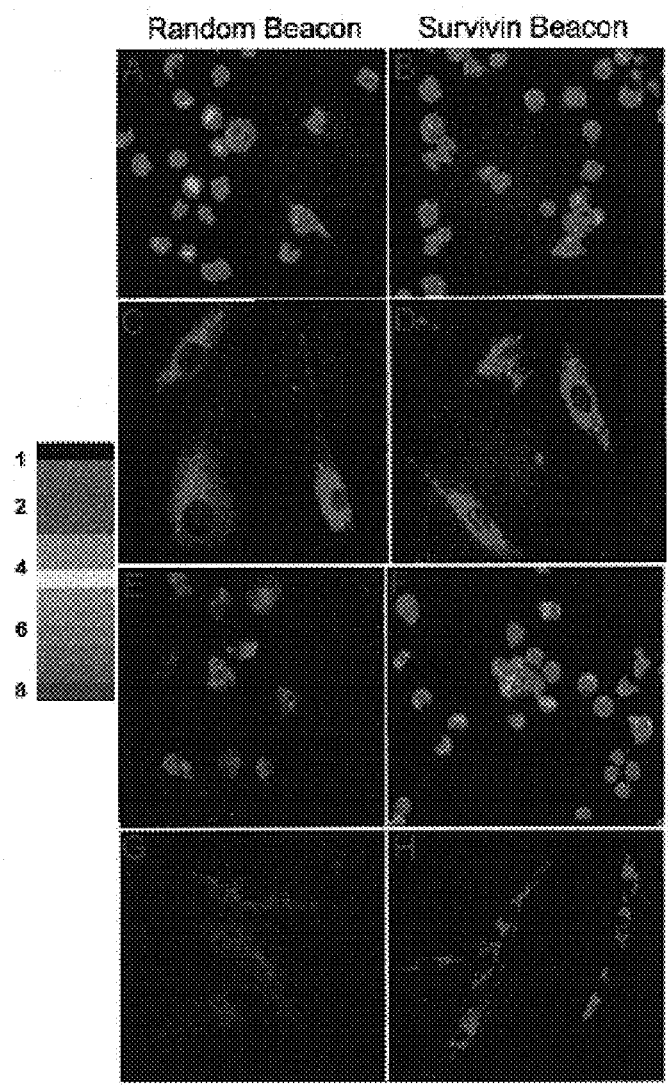
FIGS. 24A-H are fluorescence micrographs showing detection of survivin mRNA expression in MIAPaCa-2 and normal HDF cells using single donor molecular beacons only (a-d), or dual FRET molecular beacons (e-h).

Survivin mRNA expression in normal and cancerous cells. To detect survivin mRNA expression in HDF and MIAPaCa-2 cells, survivin-targeting donor beacon alone, survivin-targeting dual FRET molecular beacons, and the random beacons (Table 7) were delivered respectively into these cells using SLO. The resulting fluorescence signal was visualized 1 h after delivery. FIGS. 24A and 24C display the fluorescence signal of random beacons in HDF and MIA-PaCa-2 cells, respectively, representing the background signal level in each cell type with single beacon detection. When the fluorescence of single (unpaired) survivin-targeting donor beacons were imaged under Cy3 excitation (545 nm) and Cy3 emission detection (570 nm), the signal level in MIAPaCa-2 cells (FIG. 24B) was similar to that of random beacon (FIG. 24A), indicating that the signal was mainly due to false-positive events. The fluorescence signal of single survivin-targeting molecular beacons in HDF cells was essentially the same as that of the random beacon. Therefore, using single beacons, the true signal of survivin mRNA detection cannot be distinguished from false-positive signals.

Using FRET detection, i.e., with Cy3 excitation and Cy5 emission detection, the signal generated by random-beacons was very low in both HDF and MIAPaCa-2 cells, as can be seen from FIGS. 24E and 24G. This implies that the false-positive signals due to beacon degradation and non-specific opening can be dramatically reduced using FRET optics. Using dual FRET molecular beacons targeting survivin (Table 7), and with the FRET optics (i.e., 545 nm excitation and 570 nm emission detection), the fluorescence signal level in MIAPaCa-2 cells (FIG. 4*f*) was much higher than that in HDF cells (FIG. 4*h*), with a 250% increase in average signal intensity. This demonstrates that dual FRET molecular beacons have the ability to quantify specific mRNA expression in different cell populations.

Figure 25:
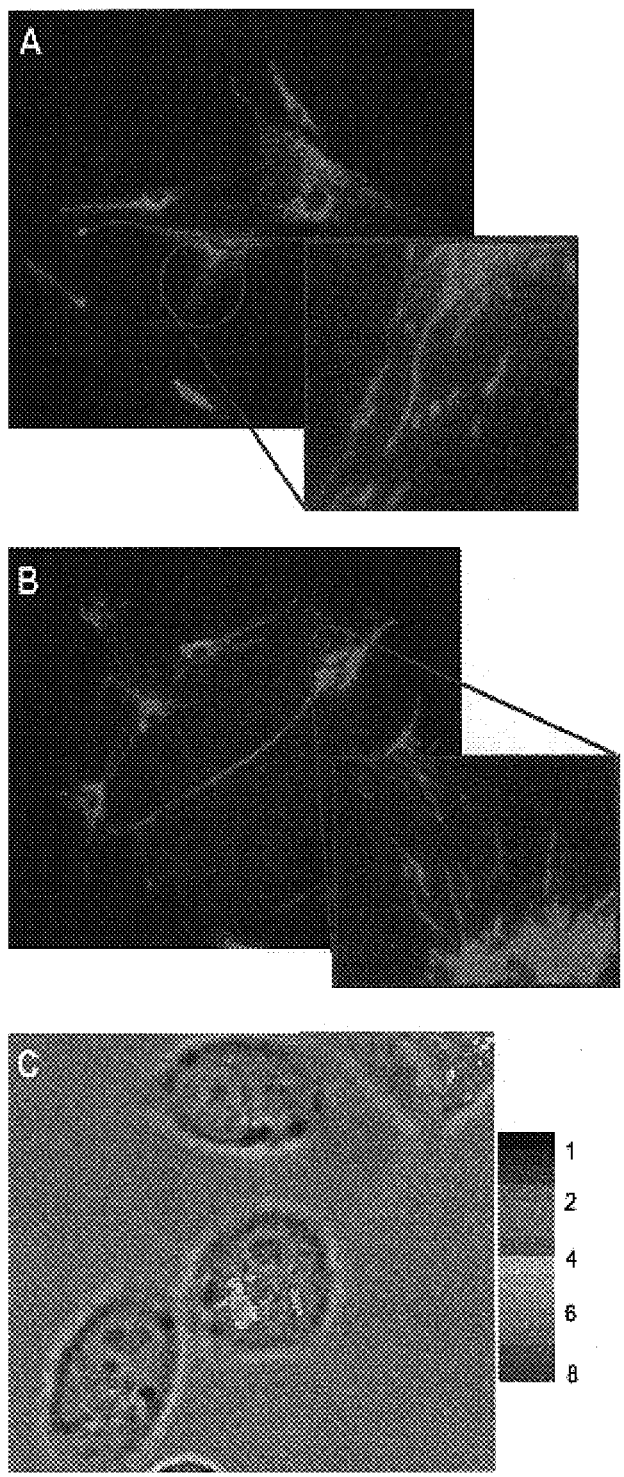
FIGS. 25A-C are fluorescence micrographs showing mRNA localization in HDF and MIAPaCa-2 cells. (a) & (b): Fluorescence images of K-ras mRNA in stimulated HDF cells. Note the filamentous K-ras mRNA localization pattern. (c) A fluorescence image of survivin mRNA localization in MIAPaCa-2 cells.

Localization of K-ras and survivin mRNA in living cells. The dual FRET molecular beacons approach can give a clear and detailed picture of mRNA localization in living cells which may reveal important information on mRNA processing, transport, and protein production. To demonstrate, in FIGS. 25A and 25B, fluorescence images of K-ras mRNA in stimulated HDF cells are shown, indicating an intriguing localization pattern. Evidently, the K-ras mRNA molecules were not randomly distributed but rather well organized and localized in the cytoplasm. It is clear from the fluorescence images that the K-ras mRNA molecules were well distributed in the cytoplasm and followed the cell morphology as indicated by the cable-like portion of an elongated cell in FIG. 25B. When the fluorescence image of a small peripheral region of a cell is expanded, the K-ras mRNAs seem to be localized along a cytoskeletal filament system, possibly the microtubule system. Indeed the co-localization of mRNA with cytoskeletal filaments has been suggested. A similar feature is shown in FIG. 25B in which the image of a small region of a different HDF cell is expanded. This is believed to be the first direct visualization of K-ras mRNA localization in living cells. Surprisingly, survivin mRNA localized in MIAPaCa-2 cell very differently. As shown in FIG. 25C in which the fluorescence image was superimposed with a white-light image of the cells, survivin mRNAs seemed to localize in a non-symmetrical pattern within MIAPaCa-2 cells, often to one side of the nucleus of the cell. The intriguing differences in mRNA localization is likely a consequence of the association of mRNA with the cell cytoskeleton or mitochondria.

Control study using in situ hybridization. As a control, a fluorescence in situ hybridization (FISH) assay detecting K-ras mRNA in fixed HDF cells was performed. A fluorescently labeled linear probe (5'-Cy5-CCTACGCCAC-CAGCTCC-3') (SEQ ID NO: 68) that has the same probe sequence as the K-ras-targeting donor molecular beacon (Table 7) was used. As demonstrated in FIG. 26a, the fluorescence image obtained in the FISH assay of K-ras mRNA detection in HDF cells gave a filamentous localization pattern as well, especially in the cell peripheral region, similar to that shown in FIGS. 25A and 25B, confirming that the mRNA localization revealed in this study is true. However, in the region near cell nucleus, the fluorescence image as a result of FISH has a high background compared with that of living cell assays using dual FRET molecular beacons. Since the probes entered both the cell cytoplasm and nucleus during FISH, a strong and diffused fluorescence signal appeared in the fixed HDF cell nuclei (FIG. 26A). As a negative control, a FISH assay with fluorescently labeled linear Poly-A probes (5'-Cy5-AAAAAAAAAAAAAAAAAA-3') (SEQ ID NO: 69) was performed and the resulting background signal was very low, as can be seen from FIG. 26B. This further confirmed that the fluorescence signal observed in the live cell and fixed cell studies of specific mRNA detection was truly due to probe/target hybridization.

Intracellular distribution of probe/target binding sites. It should be noted that in all of the images shown in FIGS. 23, 24 and 25, very little mRNA expression was detected in the cell nucleus. Although the results seemingly contradict the observation that antisense oligonucleotide probes rapidly accumulate in the nucleus, it remains to be seen if such nuclear localization is due to any fundamental biological reason. In fact, when molecular beacons were microinjected into cells, considerably more fluorescence signal was observed in the cytoplasm than nucleus. It is also possible that the intracellular distribution of signal is related to the specific delivery method used. For example, when delivered via the endocytic pathway (e.g., liposome-based transfection), antisense oligonucleotide probes tend to be trapped inside endocytic vesicles and degraded in the endosomes and lysosomes. In this Example a toxin-based delivery method was used so that the probes do not go through endosomes or lysosomes after entering cells through membrane permeabilization. After internalization the probes bind to their mRNA targets in the cytoplasm before reaching the nucleus. The probe concentrations used are significantly lower (at least a factor of 10 lower) than in most of the antisense work; therefore the probability of driving the probes into the nucleus by a high concentration gradient is much smaller. As a control fluorescently labeled linear oligonucleotides were delivered using SLO and most of the signal observed was in the cytoplasm as well (data not shown).

It has been revealed over the last few years that RNA molecules have a much wider range of functions, from physically conveying and interpreting the genetic information of living cells, to essential catalytic roles, to providing structural support for molecular machines, to gene silencing. These activities are controlled by the dynamics of both the expression levels of specific RNAs and their spatial distributions. Although in vitro assays such as DNA microarrays and Northern blotting can reflect the relative changes in RNA expression level of a cell population, imaging of specific RNA (including mRNA and microRNA) in living cells in real-time can provide essential information on how external stimuli alter the gene expression level in cells, what are the processes of RNA localization, transport, and interference, and how RNAs interact with proteins or protein complexes. As demonstrated here, the dual FRET molecular beacons technique can detect endogenous mRNA in living cells rapidly with high specificity, sensitivity, and signal-to-background ratio, thus providing a powerful tool to address all these issues. For example, in drug discovery, this method can be used in high-throughput assays to quantify and monitor the dose-dependent changes of specific mRNA expression in response to different candidate drug molecules. In basic biological studies, this method will allow researchers to visualize the dynamics and localization of specific RNAs.

A very intriguing observation in this study is the localization of mRNA in living cells. As demonstrated in FIG. 25, K-ras mRNAs displayed an interesting filament-like localization pattern in HDF cells, with a clear indication of spreading out in the cytoplasm and following the cell morphology. On the other hand, survivin mRNA was localized on one side of the cell nucleus. But why are K-ras and survivin mRNAs localized in such a peculiar way? What are the biological implications of such localization? RNA localization is an evolutionarily conserved phenomenon and may be the first step in targeting proteins to specific locations to facilitate protein-protein interactions. For example, mRNA localization and translation has been found in dendrites and axons in neural cells. It has been indicated that intracellular mRNA localization may involve interactions between targeting signals within the RNA, motor molecules, and the cytoskeleton. Although the association of mRNA with microtubules has been suggested based on the results of biochemical assays, there is still a lack of direct confirmation of mRNA localization to cytoskeletal filaments. One difficulty is that the cytoskeleton is a dynamic network and the mechanism of transport for mRNA is largely unknown.

Studies have been performed using either GFP fusion proteins that bind to RNA or by injecting fluorescently labeled mRNAs into cells and tracking them. However, by imaging endogenous mRNAs directly insights into the rates of RNA synthesis and processing, the dynamics of RNA transport and localization, and RNA-protein interactions were gained.

As demonstrated in this study, the dual FRET molecular beacons approach has the advantage that false-positive signals in living cell gene detection due to nucleases and nucleic-acid binding proteins can be significantly reduced or even eliminated, leading to high detection sensitivity. This approach is based on simultaneous hybridization of two probes to the same mRNA target so that a FRET signal can be emitted upon proper excitation. Although dual FRET linear probes have been used for living cell mRNA detection, they typically provide a higher background signal than molecular beacons as a result of the fluorescence emission of unbound probes, including donor emission at the detection wavelength and direct acceptor excitation. Further, hairpin probes can provide better specificity. While the use of dual FRET probes may further increase detection specificity, compared with single molecular beacon assays, the dual-probe approach does require twice as many probes to be delivered into cells and a longer time for probe targeting and hybridization. Therefore, for specific applications where fast detection (~30 min) is crucial, single molecular beacon assays such as that based on peptide-linked molecular beacons may be more suitable.

As demonstrated in previous studies, the use of 2'-O-methyl modified molecular beacons has certain potential advantages including improved intracellular stability and faster probe/target hybridization kinetics. However, there are issues and potential drawbacks as well. One issue is that the 2'-O-methyl modified molecular beacons may be more prone to open in living cells due to nucleic acid binding proteins, therefore generating a higher background. Further, 2'-O-methyl modified beacons are RNA-like, and therefore may form double-stranded RNA upon probe-target binding and trigger unwanted RNAi in living cells. A major advantage of using 2'-O-methyl molecular beacons is their enhanced nuclease resistance. However, most of the nucleases are in the endosomes, lysosomes and nucleus. If the probes are delivered directly into the cytoplasm and the endocytic pathway can be avoided, nuclease resistance may not be an essential issue. It is important to compare the performance of molecular beacons with different backbone modifications in living cell gene detection (Santangelo and Bao, unpublished work).

A critical issue in living cell mRNA detection is target accessibility, which is largely controlled by mRNA secondary and tertiary structures and RNA-binding proteins. Specifically, mRNA in a cell almost always has proteins bound to it, which may alter mRNA structure and prevent probe hybridization. Therefore, in selecting the probe sequences of the dual FRET molecular beacons, it is important to avoid targeting sequences that are 'buried' inside the tertiary structure or where double stranded RNA is formed. Although predictions of mRNA secondary structure can be made using existing software (e.g., mfold), they may not be accurate due to limitations of the biophysical models used. Further, there is only very limited knowledge of the sequences occupied dynamically by RNA-binding proteins. Therefore, for each gene to target, it is often necessary to select multiple unique sequences along the target RNA, and have corresponding molecular beacons designed, synthesized and tested in cells to achieve high signal-to-background ratio.

Another important issue in living cell gene detection is the quantification of mRNA expression in single cells There are many challenges in obtaining an accurate measure of the number of mRNA molecules per cell using molecular beacons (or any imaging method). For example, it is necessary to distinguish true and background signals, determine the fraction of mRNA molecules hybridized with probes, and quantify the possible self-quenching effect of the reporter, especially when mRNA is highly localized. Since the fluorescence intensity of the reporter may be altered by the intracellular environment, it is also necessary to create an internal control by, for example, injecting fluorescently labeled oligonucleotides with known quantity into the same cells and obtaining the corresponding fluorescence intensity.

A related issue in molecular beacon based gene quantification in living cells is the detection sensitivity, which is dictated not only by probe/target hybridization but also by the properties of fluorophore, fluorescence detection method, optical imaging instrumentation (microscope and camera) and background signal. Due to the low background in the dual FRET molecular beacons approach, improved detection sensitivity can be achieved compared with fluorescence in situ hybridization (FISH), as demonstrated by FIGS. 24 and 26. Using microinjection of probe/target duplexes, Sokol et al. found that the molecular beacon based approach could detect 10 mRNA molecules per cell when they are concentrated at the same spot. It is estimated that the current approach can reliably detect a few hundred copies of endogenous mRNA per cell in single cell gene detection. With the use of advanced fluorophores such as quantum dots or lanthanide chelates, fluorescence detection methods such as time-resolved FRET, and more sensitive optical imaging instruments such as that with photon counting, it is possible to detect as low as 1-5 copies of mRNA molecules in a single cell. An alternative approach is to obtain the average mRNA expression over a large number of cells (say one million), similar to that in RT-PCR studies. In this case a FRET-based flow cytometry assay using FACS (Fluorescence Activated Cell Sorter) could be performed to detect the fluorescence signal level in living cells. While single cell mRNA detection can be used to study more accurately the variation of gene expression in a cell population with different stages in the cell cycle or different disease states, the determination of the average mRNA expression level over a large number of cells may be advantageous in that, when the cell-cell variation of mRNA expression is large, it is statistically more significant and thus more reproducible compared with the mRNA level detected using a relatively small number of cells.

Throughout this application, various references are cited. The disclosures of all of these references and those references cited within those references in their entireties are hereby incorporated by reference into this application. It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and Examples be considered as exemplary only. Those skilled in the art will recognize, or will be able to ascertain using no more than routine experimentation, many equivalents to the specific embodiments of the disclosure described herein. Such equivalents are intended to be encompassed by the following claims.

We claim:

1. A probe set comprising:
   (a) a donor polymer comprising
      (i) a first polynucleotide binding domain complementary to a first region of a target polynucleotide flanked by first and second stem regions which hybridize in the absence of the target polynucleotide to form a stem-loop or random-coil structure, and
      (ii) a quantum dot; and
   (b) an acceptor polymer comprising
      (i) a second polynucleotide binding domain complementary to a second region of the target polynucleotide flanked by first and second stem regions which hybridize in the absence of the target polynucleotide to form a stem-loop or random-coil structure, and
      (ii) at least one reporter;
   wherein energy transfer occurs between the donor and the at least one reporter when the donor polymer and the acceptor polymer hybridize to the target polynucleotide and the quantum dot is exposed to an exciting amount of energy.

2. The probe set of claim 1, wherein the reporter does not emit a detectable signal when exposed to an exciting amount of energy sufficient to cause the donor to emit energy.

3. The probe set of claim 1, wherein the acceptor probe comprises at least two reporters.

4. The probe set of claim 1, wherein the polymers specifically hybridize to the target polynucleotide under stringent conditions.

5. The probe set of claim 1, wherein the polymers specifically hybridize to the target polynucleotide in vivo.

6. The probe set of claim 1, wherein the polymers further comprise a protein transduction domain, a targeting signal, a fragment thereof or a combination thereof.

7. The probe set of claim 1, wherein at least one polymer comprises a plurality of natural or non-natural nucleotides.

8. The probe set of claim 1, wherein at least one polymer comprises at least one peptide nucleic acid.

9. The probe set of claim 1, wherein at least one polymer comprises a plurality of quantum dots.

10. The probe set of claim 1, wherein at least one linkage between subunits of at least one of the polymers is modified to resist enzymatic cleavage.

11. The probe set of claim 1, wherein at least one of the polymers further comprises at least one quencher.

12. The probe set of claim 1, wherein the acceptor polymer comprises a quencher that quenches the reporter in the absence of the target polynucleotide.

13. The probe set of claim 1, wherein the quantum dot comprises ZnS, CdS, ZnSe, CdSe, CdTe, $CdSe_xTe_{1-x}$, InAs, InP, PbTe, PbSe, PbS, HgS, HgSe, HgTe, CdHgTe, GaAs, or combinations thereof.

14. The probe set of claim 1, wherein the quantum dot is encapsulated in a micelle or polymer coating, or chemically linked coatings such as silica-based coatings or DHLA (Lipoic Acid) and Mercaptoacetic Acid coatings.

15. The probe set of claim 14, wherein micelle comprises a lipid, phospholipid, or a combination thereof.

16. The probe set of claim 14, wherein the polymer coating comprises polyethylene glycol or derivatives thereof.

17. The probe set of claim 1, wherein the acceptor comprises Cy-3, ROX, Texas Red, Red Phycoerythrin (RPE), Blue Phycoerythrin (BPE), or Allophycocyanin (APC), or a fragment thereof.

18. The probe set of claim 1, further comprises at least a second set of probes specific for a second target polynucleotide.

19. A method for identifying modulators of gene expression comprising:
   (a) contacting a cell with a test compound;
   (b) contacting the cell of step (a) with the probe set of claim 1, wherein each probe is individually, operably linked to a protein transduction domain, a targeting signal, or a combination thereof;
   (c) irradiating the cell with an exciting amount of radiation;
   (d) detecting electromagnetic emissions from the cell; and
   (e) selecting the test compound that induces a change in the electromagnetic emissions of the cell contacted with the test compound compared to a control sample.

20. A method of detecting a target polynucleotide comprising:
   (a) delivering at least one probe pair to cell lysates, tissue extracts or the interior of a cell, wherein the probe pair comprises
      (i) a donor probe comprising a quantum dot and forms a stem-loop (or random coil) structure in the absence of a target polynucleotide and
      (ii) an acceptor probe comprising at least one reporter and forms a stem-loop (or random coil) structure in the absence of the target polynucleotide; and
   (b) exposing the quantum dot to an exciting amount of energy, wherein energy transfer occurs between the quantum dot and the reporter to produce a detectable signal when the donor probe and the acceptor probe hybridize to the target polynucleotide.

* * * * *

SEQUENCE LISTING

<160> NUMBER OF SEQ ID NOS: 69

<210> SEQ ID NO 1
<211> LENGTH: 11
<212> TYPE: PRT
<213> ORGANISM: Artificial Sequence
<220> FEATURE:
<223> OTHER INFORMATION: Protein Transduction Domain

<400> SEQUENCE: 1

Tyr Gly Arg Lys Lys Arg Arg Gln Arg Arg Arg
1               5                   10

<210> SEQ ID NO 2
<211> LENGTH: 9
<212> TYPE: PRT
<213> ORGANISM: Artificial Sequence
<220> FEATURE:
<223> OTHER INFORMATION: Protein Transduction Domain

<400> SEQUENCE: 2

Arg Lys Lys Arg Arg Gln Arg Arg Arg
1               5

<210> SEQ ID NO 3
<211> LENGTH: 23
<212> TYPE: DNA
<213> ORGANISM: Artificial Sequence
<220> FEATURE:
<223> OTHER INFORMATION: molecular probe

<400> SEQUENCE: 3
gagtccttcc acgataccga ctc                                           23

<210> SEQ ID NO 4
<211> LENGTH: 23
<212> TYPE: DNA
<213> ORGANISM: Artificial Sequence
<220> FEATURE:
<223> OTHER INFORMATION: Molecular probe

<400> SEQUENCE: 4
ccacatgatg gcatggactg tgg                                           23

<210> SEQ ID NO 5
<211> LENGTH: 7
<212> TYPE: PRT
<213> ORGANISM: Artificial Sequence
<220> FEATURE:
<223> OTHER INFORMATION: Protein Transduction Domain

<400> SEQUENCE: 5

Arg Arg Arg Arg Arg Arg Arg
1               5

<210> SEQ ID NO 6
<211> LENGTH: 12
<212> TYPE: PRT
<213> ORGANISM: Artificial Sequence
<220> FEATURE:
<223> OTHER INFORMATION: Protein Transduction Domain

<400> SEQUENCE: 6

Arg Arg Gln Arg Arg Thr Ser Lys Leu Met Lys Arg
1               5                   10

```
<210> SEQ ID NO 7
<211> LENGTH: 27
<212> TYPE: PRT
<213> ORGANISM: Artificial Sequence
<220> FEATURE:
<223> OTHER INFORMATION: Protein Transduction Domain

<400> SEQUENCE: 7

Gly Trp Thr Leu Asn Ser Ala Gly Tyr Leu Leu Gly Lys Ile Asn Leu
1               5                  10                  15

Lys Ala Leu Ala Ala Leu Ala Lys Lys Ile Leu
            20                  25

<210> SEQ ID NO 8
<211> LENGTH: 29
<212> TYPE: PRT
<213> ORGANISM: Artificial Sequence
<220> FEATURE:
<223> OTHER INFORMATION: Protein Transduction Domain

<400> SEQUENCE: 8

Trp Glu Ala Lys Leu Ala Lys Ala Leu Ala Lys Ala Leu Ala Lys His
1               5                  10                  15

Leu Ala Lys Ala Leu Ala Lys Ala Leu Lys Cys Glu Ala
            20                  25

<210> SEQ ID NO 9
<211> LENGTH: 34
<212> TYPE: PRT
<213> ORGANISM: Artificial Sequence
<220> FEATURE:
<223> OTHER INFORMATION: Protein Transduction Domain

<400> SEQUENCE: 9

Asp Ala Ala Thr Ala Thr Arg Gly Arg Ser Ala Ala Ser Arg Pro Thr
1               5                  10                  15

Glu Arg Pro Arg Ala Pro Ala Arg Ser Ala Ser Arg Pro Arg Arg Pro
            20                  25                  30

Val Glu

<210> SEQ ID NO 10
<211> LENGTH: 60
<212> TYPE: DNA
<213> ORGANISM: Artificial Sequence
<220> FEATURE:
<223> OTHER INFORMATION: Target sequence

<400> SEQUENCE: 10
tgacaacttt ggtatcgtgg aaggactcat gaccacagtc catgccatca ctgccaccca      60

<210> SEQ ID NO 11
<211> LENGTH: 24
<212> TYPE: DNA
<213> ORGANISM: Artificial Sequence
<220> FEATURE:
<223> OTHER INFORMATION: Acceptor Beacon

<400> SEQUENCE: 11
ctcagaccat agcaccttcc tgag      24

<210> SEQ ID NO 12
<211> LENGTH: 23
<212> TYPE: DNA
```

<210> SEQ ID NO 12
<211> LENGTH: 23
<212> TYPE: DNA
<213> ORGANISM: Artificial Sequence
<220> FEATURE:
<223> OTHER INFORMATION: Donor Beacon

<400> SEQUENCE: 12
ggtgtcaggt acggtagtac acc                                              23

<210> SEQ ID NO 13
<211> LENGTH: 16
<212> TYPE: PRT
<213> ORGANISM: Artificial Sequence
<220> FEATURE:
<223> OTHER INFORMATION: Protein Transduction Domain

<400> SEQUENCE: 13

Arg Gln Ile Lys Ile Trp Phe Gln Asn Arg Arg Met Lys Trp Lys Lys
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Nuclear localization signal

<400> SEQUENCE: 14

Pro Lys Lys Lys Arg Lys Val
1               5

<210> SEQ ID NO 15
<211> LENGTH: 7
<212> TYPE: PRT
<213> ORGANISM: Artificial Sequence
<220> FEATURE:
<223> OTHER INFORMATION: Nuclear localization signal

<400> SEQUENCE: 15

Gly Lys Lys Arg Ser Lys Val
1               5

<210> SEQ ID NO 16
<211> LENGTH: 7
<212> TYPE: PRT
<213> ORGANISM: Artificial Sequence
<220> FEATURE:
<223> OTHER INFORMATION: Nuclear localization signal

<400> SEQUENCE: 16

Lys Ser Arg Lys Arg Lys Leu
1               5

<210> SEQ ID NO 17
<211> LENGTH: 19
<212> TYPE: PRT
<213> ORGANISM: Artificial Sequence
<220> FEATURE:
<223> OTHER INFORMATION: Nuclear localization signal

<400> SEQUENCE: 17

Lys Arg Pro Ala Ala Thr Lys Ala Gly Gln Ala Lys Lys Lys Lys
1               5                   10                  15

Leu Asp Lys

<210> SEQ ID NO 18
<211> LENGTH: 20
<212> TYPE: PRT

<210> SEQ ID NO 18
<211> LENGTH: 20
<212> TYPE: PRT
<213> ORGANISM: Artificial Sequence
<220> FEATURE:
<223> OTHER INFORMATION: Nuclear localization signal

<400> SEQUENCE: 18

Arg Lys Lys Arg Lys Thr Glu Glu Glu Ser Pro Leu Lys Asp Lys Ala
1               5                   10                  15

Lys Lys Ser Lys
            20

<210> SEQ ID NO 19
<211> LENGTH: 20
<212> TYPE: PRT
<213> ORGANISM: Artificial Sequence
<220> FEATURE:
<223> OTHER INFORMATION: Nuclear localization signal

<400> SEQUENCE: 19

Lys Asp Cys Val Met Asn Lys His His Arg Asn Arg Cys Gln Tyr Cys
1               5                   10                  15

Arg Leu Gln Arg
            20

<210> SEQ ID NO 20
<211> LENGTH: 9
<212> TYPE: PRT
<213> ORGANISM: Artificial Sequence
<220> FEATURE:
<223> OTHER INFORMATION: Nuclear localization signal

<400> SEQUENCE: 20

Pro Ala Ala Lys Arg Val Lys Leu Asp
1               5

<210> SEQ ID NO 21
<211> LENGTH: 20
<212> TYPE: PRT
<213> ORGANISM: Artificial Sequence
<220> FEATURE:
<223> OTHER INFORMATION: nuclear localization signal

<400> SEQUENCE: 21

Lys Lys Tyr Glu Asn Val Val Ile Lys Arg Ser Pro Arg Lys Arg Gly
1               5                   10                  15

Arg Pro Arg Lys
            20

<210> SEQ ID NO 22
<211> LENGTH: 23
<212> TYPE: DNA
<213> ORGANISM: Artificial Sequence
<220> FEATURE:
<223> OTHER INFORMATION: Donor probe

<400> SEQUENCE: 22
ccacatgatg gcatggactg tgg                                          23

<210> SEQ ID NO 23
<211> LENGTH: 18
<212> TYPE: DNA
<213> ORGANISM: Artificial Sequence
<220> FEATURE:
<223> OTHER INFORMATION: Donor probe

<400> SEQUENCE: 23

|  |  |
|---|---|
| tgatggcatg gactgtgg | 18 |

<210> SEQ ID NO 24
<211> LENGTH: 25
<212> TYPE: DNA
<213> ORGANISM: Artificial Sequence
<220> FEATURE:
<223> OTHER INFORMATION: Stem-loop probe

<400> SEQUENCE: 24

|  |  |
|---|---|
| gagtccttcc acgtaaccag gactc | 25 |

<210> SEQ ID NO 25
<211> LENGTH: 27
<212> TYPE: DNA
<213> ORGANISM: Artificial Sequence
<220> FEATURE:
<223> OTHER INFORMATION: Target sequence

<400> SEQUENCE: 25

|  |  |
|---|---|
| actttggtat cgtggaagga ctcatga | 27 |

<210> SEQ ID NO 26
<211> LENGTH: 22
<212> TYPE: DNA
<213> ORGANISM: Artificial Sequence
<220> FEATURE:
<223> OTHER INFORMATION: Stem-loop probe

<400> SEQUENCE: 26

|  |  |
|---|---|
| gagtccttcc acgataccac tc | 22 |

<210> SEQ ID NO 27
<211> LENGTH: 23
<212> TYPE: DNA
<213> ORGANISM: Artificial Sequence
<220> FEATURE:
<223> OTHER INFORMATION: Acceptor probe

<400> SEQUENCE: 27

|  |  |
|---|---|
| gagtccttcc acgataccga ctc | 23 |

<210> SEQ ID NO 28
<211> LENGTH: 23
<212> TYPE: DNA
<213> ORGANISM: Artificial Sequence
<220> FEATURE:
<223> OTHER INFORMATION: Acceptor probe

<400> SEQUENCE: 28

|  |  |
|---|---|
| gagtccttcc acgataccga ctc | 23 |

<210> SEQ ID NO 29
<211> LENGTH: 23
<212> TYPE: DNA
<213> ORGANISM: Artificial Sequence
<220> FEATURE:
<223> OTHER INFORMATION: Acceptor probe

<400> SEQUENCE: 29

|  |  |
|---|---|
| gagtccttcc acgataccga ctc | 23 |

<210> SEQ ID NO 30
<211> LENGTH: 49
<212> TYPE: DNA
<213> ORGANISM: Artificial Sequence

```
<220> FEATURE:
<223> OTHER INFORMATION: Target sequence

<400> SEQUENCE: 30
actttggtat cgtggaagga ctcataccac agtccatgcc atcactgcc                    49

<210> SEQ ID NO 31
<211> LENGTH: 50
<212> TYPE: DNA
<213> ORGANISM: Artificial Sequence
<220> FEATURE:
<223> OTHER INFORMATION: Target sequence

<400> SEQUENCE: 31
actttggtat cgtggaagga ctcatgacca cagtccatgc catcactgcc                   50

<210> SEQ ID NO 32
<211> LENGTH: 51
<212> TYPE: DNA
<213> ORGANISM: Artificial Sequence
<220> FEATURE:
<223> OTHER INFORMATION: Target sequence

<400> SEQUENCE: 32
actttggtat cgtggaagga ctcattgacc acagtccatg ccatcactgc c                 51

<210> SEQ ID NO 33
<211> LENGTH: 52
<212> TYPE: DNA
<213> ORGANISM: Artificial Sequence
<220> FEATURE:
<223> OTHER INFORMATION: Target sequence

<400> SEQUENCE: 33
actttggtat cgtggaagga ctcatttgac cacagtccat gccatcactg cc                52

<210> SEQ ID NO 34
<211> LENGTH: 22
<212> TYPE: DNA
<213> ORGANISM: Artificial Sequence
<220> FEATURE:
<223> OTHER INFORMATION: Shared-stem probe

<400> SEQUENCE: 34
gagtccttcc acgataccac tc                                                 22

<210> SEQ ID NO 35
<211> LENGTH: 24
<212> TYPE: DNA
<213> ORGANISM: Artificial Sequence
<220> FEATURE:
<223> OTHER INFORMATION: Shared-stem probe

<400> SEQUENCE: 35
gagtccttcc acgataccag actc                                               24

<210> SEQ ID NO 36
<211> LENGTH: 25
<212> TYPE: DNA
<213> ORGANISM: Artificial Sequence
<220> FEATURE:
<223> OTHER INFORMATION: Shared-stem probe

<400> SEQUENCE: 36
gagtccttcc acgataccag gactc                                              25
```

<210> SEQ ID NO 37
<211> LENGTH: 27
<212> TYPE: DNA
<213> ORGANISM: Artificial Sequence
<220> FEATURE:
<223> OTHER INFORMATION: Conventional probe

<400> SEQUENCE: 37
cctcgagtcc ttccacgata ccagagg                                27

<210> SEQ ID NO 38
<211> LENGTH: 29
<212> TYPE: DNA
<213> ORGANISM: Artificial Sequence
<220> FEATURE:
<223> OTHER INFORMATION: Conventional probe

<400> SEQUENCE: 38
ctgacgagtc cttccacgat accagtcag                              29

<210> SEQ ID NO 39
<211> LENGTH: 30
<212> TYPE: DNA
<213> ORGANISM: Artificial Sequence
<220> FEATURE:
<223> OTHER INFORMATION: Conventional probe

<400> SEQUENCE: 39
ctgagcgagt ccttccacga taccagctca                             30

<210> SEQ ID NO 40
<211> LENGTH: 27
<212> TYPE: DNA
<213> ORGANISM: Artificial Sequence
<220> FEATURE:
<223> OTHER INFORMATION: Target sequence

<400> SEQUENCE: 40
actttggtat cgtggaagga ctcatga                                27

<210> SEQ ID NO 41
<211> LENGTH: 27
<212> TYPE: DNA
<213> ORGANISM: Artificial Sequence
<220> FEATURE:
<223> OTHER INFORMATION: Target sequence

<400> SEQUENCE: 41
actttggtat cgtggaagga atcatga                                27

<210> SEQ ID NO 42
<211> LENGTH: 27
<212> TYPE: DNA
<213> ORGANISM: Artificial Sequence
<220> FEATURE:
<223> OTHER INFORMATION: Target sequence

<400> SEQUENCE: 42
actttggtat cgtagaagga ctcatga                                27

<210> SEQ ID NO 43
<211> LENGTH: 27
<212> TYPE: DNA
<213> ORGANISM: Artificial Sequence
<220> FEATURE:
<223> OTHER INFORMATION: Target sequence

```
<400> SEQUENCE: 43
actttggtat cgtagaagga atcatga                                    27

<210> SEQ ID NO 44
<211> LENGTH: 27
<212> TYPE: DNA
<213> ORGANISM: Artificial Sequence
<220> FEATURE:
<223> OTHER INFORMATION: Target sequence

<400> SEQUENCE: 44
actttggtat cgtaaaagga ctcatga                                    27

<210> SEQ ID NO 45
<211> LENGTH: 78
<212> TYPE: DNA
<213> ORGANISM: Artificial Sequence
<220> FEATURE:
<223> OTHER INFORMATION: Molecular beacon

<400> SEQUENCE: 45
atgactgaat ataaacttgt ggtagttgga gctggtggcg taggcaagag tgccttgacg   60
atacagctaa ttcagaat                                              78

<210> SEQ ID NO 46
<211> LENGTH: 24
<212> TYPE: DNA
<213> ORGANISM: Artificial Sequence
<220> FEATURE:
<223> OTHER INFORMATION: Donor Beacon

<400> SEQUENCE: 46
agtgcgctgt atcgtcaagg cact                                       24

<210> SEQ ID NO 47
<211> LENGTH: 22
<212> TYPE: DNA
<213> ORGANISM: Artificial Sequence
<220> FEATURE:
<223> OTHER INFORMATION: Acceptor Beacon

<400> SEQUENCE: 47
cctacgccat cagctccgta gg                                         22

<210> SEQ ID NO 48
<211> LENGTH: 22
<212> TYPE: DNA
<213> ORGANISM: Artificial Sequence
<220> FEATURE:
<223> OTHER INFORMATION: Acceptor Beacon

<400> SEQUENCE: 48
cctacgccaa cagctccgta gg                                         22

<210> SEQ ID NO 49
<211> LENGTH: 22
<212> TYPE: DNA
<213> ORGANISM: Artificial Sequence
<220> FEATURE:
<223> OTHER INFORMATION: Acceptor Beacon

<400> SEQUENCE: 49
cctacgccac gagctccgta gg                                         22
```

<210> SEQ ID NO 50
<211> LENGTH: 22
<212> TYPE: DNA
<213> ORGANISM: Artificial Sequence
<220> FEATURE:
<223> OTHER INFORMATION: Acceptor Beacon

<400> SEQUENCE: 50
cctacgccac aagctccgta gg                                              22

<210> SEQ ID NO 51
<211> LENGTH: 121
<212> TYPE: DNA
<213> ORGANISM: Artificial Sequence
<220> FEATURE:
<223> OTHER INFORMATION: Molecular Beacon

<400> SEQUENCE: 51
atgggtgccc cgacgttgcc ccctgcctgg cagcccttc tcaaggacca ccgcatctct      60
acattcaaga actggccctt cttggagggc tgcgcctgca ccccggagcg gatggccgag    120
g                                                                    121

<210> SEQ ID NO 52
<211> LENGTH: 23
<212> TYPE: DNA
<213> ORGANISM: Artificial Sequence
<220> FEATURE:
<223> OTHER INFORMATION: Donor Beacon

<400> SEQUENCE: 52
ccttgagaaa gggctgccca agg                                             23

<210> SEQ ID NO 53
<211> LENGTH: 23
<212> TYPE: DNA
<213> ORGANISM: Acceptor Beacon

<400> SEQUENCE: 53
ccgcattgaa tgtagagatg cgg                                             23

<210> SEQ ID NO 54
<211> LENGTH: 24
<212> TYPE: DNA
<213> ORGANISM: Artificial Sequence
<220> FEATURE:
<223> OTHER INFORMATION: Donor probe

<400> SEQUENCE: 54
acctggatgt tgtcctcgtc aggt                                            24

<210> SEQ ID NO 55
<211> LENGTH: 24
<212> TYPE: DNA
<213> ORGANISM: Artificial Sequence
<220> FEATURE:
<223> OTHER INFORMATION: Acceptor probe

<400> SEQUENCE: 55
aagattgaag accttggcga tctt                                            24

<210> SEQ ID NO 56
<211> LENGTH: 78
<212> TYPE: DNA
<213> ORGANISM: Artificial Sequence

```
<220> FEATURE:
<223> OTHER INFORMATION: Target Sequence

<400> SEQUENCE: 56
atgactgaat ataaacttgt ggtagttgga gctggtggcg taggcaagag tgccttgacg      60
atacagctaa ttcagaat                                                    78

<210> SEQ ID NO 57
<211> LENGTH: 22
<212> TYPE: DNA
<213> ORGANISM: Artificial Sequence
<220> FEATURE:
<223> OTHER INFORMATION: Donor probe

<400> SEQUENCE: 57
cctacgccac cagctccgta gg                                               22

<210> SEQ ID NO 58
<211> LENGTH: 24
<212> TYPE: DNA
<213> ORGANISM: Artificial Sequence
<220> FEATURE:
<223> OTHER INFORMATION: acceptor probe

<400> SEQUENCE: 58
agtgcgctgt atcgtcaagg cact                                             24

<210> SEQ ID NO 59
<211> LENGTH: 78
<212> TYPE: DNA
<213> ORGANISM: Artificial Sequence
<220> FEATURE:
<223> OTHER INFORMATION: Target Sequence

<400> SEQUENCE: 59
atgggtgccc cgacgttgcc ccctgcctgg cagcccttc tcaaggacca ccgcatctct       60
acattcaaga actggccc                                                    78

<210> SEQ ID NO 60
<211> LENGTH: 20
<212> TYPE: DNA
<213> ORGANISM: Artificial Sequence
<220> FEATURE:
<223> OTHER INFORMATION: Donor probe

<400> SEQUENCE: 60
gagaaagggc tgccattctc                                                  20

<210> SEQ ID NO 61
<211> LENGTH: 21
<212> TYPE: DNA
<213> ORGANISM: Artificial Sequence
<220> FEATURE:
<223> OTHER INFORMATION: Acceptor probe

<400> SEQUENCE: 61
accacgtaga gatgcggtgg t                                                21

<210> SEQ ID NO 62
<211> LENGTH: 26
<212> TYPE: DNA
<213> ORGANISM: Artificial Sequence
<220> FEATURE:
<223> OTHER INFORMATION: Donor probe
```

-continued

```
<400> SEQUENCE: 62
cacgtcgaca agcgcaccga tacgtg                                        26

<210> SEQ ID NO 63
<211> LENGTH: 26
<212> TYPE: DNA
<213> ORGANISM: Artificial Sequence
<220> FEATURE:
<223> OTHER INFORMATION: Acceptor probe

<400> SEQUENCE: 63
acgtgcgaca agcgcaccga tcacgt                                        26

<210> SEQ ID NO 64
<211> LENGTH: 20
<212> TYPE: DNA
<213> ORGANISM: Artificial Sequence
<220> FEATURE:
<223> OTHER INFORMATION: Primer

<400> SEQUENCE: 64
gattcctaca ggaagcaagt                                               20

<210> SEQ ID NO 65
<211> LENGTH: 17
<212> TYPE: DNA
<213> ORGANISM: Artificial Sequence
<220> FEATURE:
<223> OTHER INFORMATION: Primer

<400> SEQUENCE: 65
taatggtgaa tatcttc                                                  17

<210> SEQ ID NO 66
<211> LENGTH: 24
<212> TYPE: DNA
<213> ORGANISM: Artificial Sequence
<220> FEATURE:
<223> OTHER INFORMATION: Forward primer

<400> SEQUENCE: 66
ccacccatgg caaattccat ggca                                          24

<210> SEQ ID NO 67
<211> LENGTH: 24
<212> TYPE: DNA
<213> ORGANISM: Artificial Sequence
<220> FEATURE:
<223> OTHER INFORMATION: Reverse primer

<400> SEQUENCE: 67
tctagacggc aggtcaggtc cacc                                          24

<210> SEQ ID NO 68
<211> LENGTH: 17
<212> TYPE: DNA
<213> ORGANISM: Artificial Sequence
<220> FEATURE:
<223> OTHER INFORMATION: Linear probe

<400> SEQUENCE: 68
cctacgccac cagctcc                                                  17

<210> SEQ ID NO 69
<211> LENGTH: 18
```

```
<212> TYPE: DNA
<213> ORGANISM: Artificial Sequence
<220> FEATURE:
<223> OTHER INFORMATION: Control

<400> SEQUENCE: 69
aaaaaaaaaa aaaaaaaa                                              18
```